(12) United States Patent
Aboshyan-Sorgho et al.

(10) Patent No.: US 12,201,956 B2
(45) Date of Patent: Jan. 21, 2025

(54) TUNABLE PROCESS FOR SILICA CAPSULES/SPHERES PREPARATION AND THEIR USE

(71) Applicant: Silicycle Inc., Québec (CA)

(72) Inventors: Lilit Aboshyan-Sorgho, Québec (CA); François Beland, L'Ancienne-Lorette (CA); Delphine Desplantier-Giscard, Québec (CA); Michel Morin, Québec (CA); Valerica Pandarus, Québec (CA)

(73) Assignee: PHARMA IN SILICA LABORATORIES INC., Quebec (CA)

( * ) Notice: Subject to any disclaimer, the term of this patent is extended or adjusted under 35 U.S.C. 154(b) by 682 days.

(21) Appl. No.: 17/284,841

(22) PCT Filed: Oct. 16, 2019

(86) PCT No.: PCT/CA2019/051465
§ 371 (c)(1),
(2) Date: Apr. 13, 2021

(87) PCT Pub. No.: WO2020/077451
PCT Pub. Date: Apr. 23, 2020

(65) Prior Publication Data
US 2021/0387155 A1   Dec. 16, 2021

Related U.S. Application Data

(60) Provisional application No. 62/746,444, filed on Oct. 16, 2018.

(51) Int. Cl.
| | |
|---|---|
| *B01J 13/14* | (2006.01) |
| *A61K 8/11* | (2006.01) |
| *A61K 8/31* | (2006.01) |
| *A61K 8/34* | (2006.01) |
| *A61K 8/37* | (2006.01) |
| *A61K 8/67* | (2006.01) |
| *A61K 8/89* | (2006.01) |
| *A61K 8/9767* | (2017.01) |
| *A61K 8/9789* | (2017.01) |
| *A61K 9/50* | (2006.01) |
| *A61K 31/122* | (2006.01) |
| *A61K 47/44* | (2017.01) |
| *A61Q 13/00* | (2006.01) |
| *A61Q 19/08* | (2006.01) |
| *C08L 83/04* | (2006.01) |

(52) U.S. Cl.
CPC ............. *B01J 13/14* (2013.01); *A61K 8/11* (2013.01); *A61K 8/31* (2013.01); *A61K 8/34* (2013.01); *A61K 8/342* (2013.01); *A61K 8/37* (2013.01); *A61K 8/671* (2013.01); *A61K 8/89* (2013.01); *A61K 8/9767* (2017.08); *A61K 8/9789* (2017.08); *A61K 9/50* (2013.01); *A61K 31/122* (2013.01); *A61K 47/44* (2013.01); *A61Q 13/00* (2013.01); *A61Q 19/08* (2013.01); *C08L 83/04* (2013.01); *C08L 2205/20* (2013.01)

(58) Field of Classification Search
CPC ...... B01J 13/14; A61K 8/9767; A61K 8/9789; A61K 8/11; A61K 8/31; A61K 8/34; A61K 8/342; A61K 8/37; A61K 8/671; A61K 8/89; A61K 9/50; A61K 31/122; A61K 47/44; A61Q 13/00; A61Q 19/08; C08L 83/04; C08L 2205/20
See application file for complete search history.

(56) References Cited

U.S. PATENT DOCUMENTS

| | | |
|---|---|---|
| 5,028,653 A | 7/1991 | Desmonceau et al. |
| 7,754,646 B2 | 7/2010 | Trau et al. |
| 7,758,888 B2 | 7/2010 | Lapidot et al. |
| 8,084,001 B2 | 12/2011 | Burns et al. |
| 8,110,284 B2 | 2/2012 | Naigertsik et al. |
| 8,465,769 B2 | 6/2013 | Petereit et al. |
| 8,617,580 B2 | 12/2013 | Toledano et al. |
| 8,962,138 B2 | 2/2015 | Bauer et al. |
| 9,199,211 B2 | 12/2015 | Tschernjaew et al. |
| 9,561,485 B2 | 2/2017 | Yan et al. |
| 9,730,899 B2 | 8/2017 | Bär et al. |
| 9,868,103 B2 | 1/2018 | Toledano et al. |
| 10,343,903 B2 | 7/2019 | Zink et al. |
| 10,485,881 B2 | 11/2019 | Bradbury et al. |
| 10,525,433 B2 | 1/2020 | Toledano et al. |
| 10,548,989 B2 | 2/2020 | Bradbury et al. |

(Continued)

FOREIGN PATENT DOCUMENTS

| | | |
|---|---|---|
| CA | 2985083 A1 | 11/2016 |
| CA | 3010711 | 1/2017 |

(Continued)

OTHER PUBLICATIONS http://www.news-medical.net:80/health/What-are-Cannabinoids.aspx; accessed Nov. 2023 (Year: 2014).*

(Continued)

*Primary Examiner* — Robert A Wax
*Assistant Examiner* — John W Lippert, III
(74) *Attorney, Agent, or Firm* — CANTOR COLBURN LLP

(57) ABSTRACT

The disclosure relates to porous and non-porous silica capsules (capsules in capsule or core-shell capsules), porous microspheres, as well as their direct phase emulsification process without surfactant and their use, wherein the particles comprise a liposoluble active/payload.

11 Claims, 20 Drawing Sheets

(56) References Cited

U.S. PATENT DOCUMENTS

| | | | |
|---|---|---|---|
| 10,548,997 | B2 | 2/2020 | Bradbury et al. |
| 10,548,998 | B2 | 2/2020 | Bradbury et al. |
| 10,660,856 | B2 | 5/2020 | Monsuur |
| 10,668,024 | B2 | 6/2020 | Liong et al. |
| 10,688,462 | B2 | 6/2020 | Toledano et al. |
| 10,732,115 | B2 | 8/2020 | Wiesner et al. |
| 10,780,046 | B2 | 9/2020 | Shevachman et al. |
| 10,828,255 | B2 | 11/2020 | Nel et al. |
| 10,835,495 | B2 | 11/2020 | Libanati et al. |
| 10,940,216 | B2 | 3/2021 | Bradbury et al. |
| 10,986,997 | B2 | 4/2021 | Bradbury et al. |
| 11,031,591 | B2 | 6/2021 | Takano et al. |
| 11,071,878 | B2 | 7/2021 | Toledano et al. |
| 11,160,761 | B2 | 11/2021 | Brahms et al. |
| 11,246,946 | B2 | 2/2022 | Bradbury et al. |
| 2003/0124564 | A1 | 7/2003 | Trau et al. |
| 2005/0037087 | A1 | 2/2005 | Lapidot et al. |
| 2010/0174045 | A1 | 7/2010 | Thierauf |
| 2012/0104639 | A1 | 5/2012 | Traynor et al. |
| 2014/0162872 | A1* | 6/2014 | Bohringer ........ B01J 31/06 502/402 |
| 2016/0158121 | A1* | 6/2016 | Lei ............ C11D 17/0039 424/70.17 |
| 2016/0214075 | A1 | 7/2016 | Suslick et al. |
| 2016/0316806 | A1 | 11/2016 | Gehin-Delval et al. |
| 2018/0133346 | A1 | 5/2018 | Wiesner et al. |
| 2018/0200689 | A1 | 7/2018 | Zhao et al. |
| 2019/0282712 | A1 | 9/2019 | Bradbury et al. |
| 2019/0282990 | A1 | 9/2019 | Dreher et al. |
| 2020/0139332 | A1 | 5/2020 | Marques et al. |
| 2020/0179538 | A1 | 6/2020 | Ma et al. |
| 2020/0330948 | A1 | 10/2020 | Cardoso et al. |
| 2021/0007996 | A1 | 1/2021 | Toledano et al. |

FOREIGN PATENT DOCUMENTS

| | | | | |
|---|---|---|---|---|
| CN | 1311266 | A | 5/2001 | |
| CN | 102186462 | A | 9/2011 | |
| CN | 102604100 | A | 7/2012 | |
| CN | 105118598 | A | 12/2015 | |
| CN | 105344334 | A | 2/2016 | |
| CN | 112969526 | A | 6/2021 | |
| CN | 113195090 | A | 7/2021 | |
| EP | 0934773 | A2 | 8/1999 | |
| EP | 2335818 | A1 | 6/2011 | |
| JP | 2000225332 | A | 8/2000 | |
| JP | 2001106612 | A | 4/2001 | |
| JP | 2009196829 | A | 9/2009 | |
| KR | 20190069573 | A | 6/2019 | |
| WO | 03002633 | A1 | 1/2003 | |
| WO | 2008045427 | A1 | 4/2008 | |
| WO | 2008072239 | A2 | 6/2008 | |
| WO | WO-2011131644 | A1 * | 10/2011 | ............ A01N 25/28 |
| WO | 201209448 | | 1/2012 | |
| WO | 2012110995 | | 8/2012 | |
| WO | WO-2015188215 | A1 * | 12/2015 | ......... G01N 21/6428 |
| WO | WO-2016049456 | A1 * | 3/2016 | ............ A01N 25/28 |
| WO | 2017150423 | A1 | 9/2017 | |
| WO | WO-2017161364 | A1 * | 9/2017 | ............ A21D 2/02 |
| WO | 2017201528 | A1 | 11/2017 | |
| WO | WO-2018055126 | A1 * | 3/2018 | ............ A01N 25/28 |
| WO | 2020077451 | A1 | 4/2020 | |
| WO | 2020097717 | A1 | 5/2020 | |

OTHER PUBLICATIONS https://www.chemicool.com/definition/mineral_oils.html#:~:text=In%20general%2C%20highly%20refined%20pharmaceutical,aromatics%20may%20also%20be%20present.; accessed Nov. 2023 (Year: 2020).* http://sites.science.oregonstate.edu/chemistry/courses/ch130/old/VITCTEXT.htm#:~:text=Pure%20vitamin%20C%20is%20a,rapidly%20oxidized%20by%20dissolved%20oxygen.; accessed Nov. 2023 (Year: 2020).*

Shivakumar et al. Microencapsulation: A promising technique for controlled drug delivery; Res Pharm Sci. Jul.-Dec. 2010; 5(2): 65-77. (Year: 2010).*

Chen et al. "One-pot synthesis of polyvinyl alcohol/silica composite microspheres in a surfactant-free system for biomedical applications"; J Sol-Gel Science Technology, vol. 79, 2016, pp. 525-529.

Devi et al. "A Review on Synthesis, Characterization and Applications of Silica Particles"; International Journal of Advanced Engineering Research and Technology (IJAERT), 2016, vol. 4, Issue 7, pp. 249-255.

Effati et al. "One-pot synthesis of sub-50 nm vinyl- and acrylate-modified silica nanoparticles"; Powder Technology, 2012, vol. 219, pp. 276-283.

International Search Report; International Application No. PCT/CA2019/051605; International Filing Date: Nov. 12, 2019; Date of Mailing: Jan. 31, 2020; 5 pages.

International Search Report; International Application No. PCT/CA2020/050215; International Filing Date: Feb. 19, 2020; Date of Mailing: Apr. 24, 2020; 3 pages.

Kumar et al. "CPMV-induced synthesis of hollow mesoporous SiO2 nanocapsules with excellent performance in drug delivery"; J Sol-Gel Science Technology, vol. 44, 2015, pp. 4308-4317.

Lazareva et al. "Synthesis of High-Purity Silica Nanoparticles by Sol-Gel Method"; Eurasian Chemico-Technological Journal; Eurasian Chemico-Technological Journal, 2017, vol. 19, pp. 295-302.

Ma, et al., "Multifunctional Nano-Architecture for Biomedical Applications" Chem. Mater. 2006, vol. 18 (pp. 1920-1927).

Sadek et al. "Preparation and Characterization of Silica and Clay-Silica Core-Shell Nanoparticles Using Sol=Gel Method"; Advances in Nanoparticles, 2013, vol. 2, pp. 165-175.

Written Opinion; International Application No. PCT/CA2019/051605; International Filing Date: Nov. 12, 2019; Date of Mailing: Jan. 31, 2020; 6 pages.

Written Opinion; International Application No. PCT/CA2020/050215; International Filing Date: Feb. 19, 2020; Date of Mailing: Apr. 24, 2020; 5 pages.

Zhang et al. "Surfactant-free synthesis of silica aerogel microspheres with hierarchically porous structure" Journal of Colloid and Interface Science, vol. 515, 2018, pp. 1-9.

Cai, Q. et al.; "Dilute Solution Routes to Various Controllable Morphologies of MCM-41 Silica with a Basic Medium"; Chemistry of Materials, vol. 13, Issue No. 2; 2001; pp. 258-263.

Olejniczak, Z. et al.; "29Si MAS NMR and FTIR study of inorganic-organic hybrid gels"; Journal of Molecular Structure, vol. 744; 2005; pp. 465-471.

Chen, Z. et al.; "Inclusion of Phase-Change Materials in Submicron Silica Capsules Using a Surfactant-Free Emulsion Approach"; Langmuir, vol. 34, Issue No. 35; 2018; pp. 10397-10406; doi: 10.1021/acs.langmuir.8b02435.

International Search Report and Written Opinion for International Application PCT/CA2019/051465; International Filing Date: Oct. 16, 2019; Date of Mailing: Jan. 10, 2020; 11 pages.

O'Sullivan, M. et al.; "Silica-Shell/Oil-Core Microcapsules with Controlled Shell Thickness and Their Breakage Stress"; Langmuir, vol. 25, Issue No. 14; 2009; pp. 7962-7966; doi: 10.1021/la9006229.

Fortuniak, W. et al., "Route to hydrophilic, hydrophobic and functionalized cross-linked polysiloxane microspheres" Polymer 54 (2013) 3156-3165.

Bernardos, et al. Enzyme Responsive intracellular Controlled Release Using Nanometric Silica Mesoporous Supports Capped with Saccharides. ACS Nano vol. 4, No. 11, 6353-6368, Year: 2010.

Chen, et al. Overcoming acquired drug resistance in colorectal cancer cells by targeted delivery of 5-FU with EGF grafted hollow mesoporous silica nanoparticles. Nanoscale, vol. 7, 14080. Year: 2015.

Law, Kock-Yee. Definitions for Hydrophilicity, Hydrophobicity, and Superhydrophobicity: Getting the Basics Right. J. Phys. Chem. Lett., vol. 5, 686-688. Year: 2014.

USPTO Non-Final Rejection (Office Action) mailed Dec. 5, 2023 for U.S. Appl. No. 17/290,052, filed Apr. 29, 2021.

(56) References Cited

OTHER PUBLICATIONS

USPTO Non-Final Rejection (Office Action) mailed Sep. 14, 2023 for U.S. Appl. No. 17/431,934, filed Aug. 18, 2021.
Walton, et al. Applicability of the BET Method for Determining Surface Areas of Microporous Metal-Organic Frameworks. J. Am. Chem. Soc. 2007, vol. 129, 8552-8556.
Jones et al., Periodic Mesoporous Organosilicas with Domain Functionality; Synthesis and Advanced Characterization; Chem. Mater. 2008, 20, 3385-3397.
Tuulli et al., Deposition of aminosilane coatings on porous A1203 microspheres by means of dielectric barrier discharges; Plasma Process Polym, 2017; 14:e1600211.
Xia et al., Synthesis chemistry and application development of periodic mesoporous Organosilicas; J. Porous Mater (2010) 17:225-252.
Narayan et al., Review Mesoporous Silica Nanaparticles: A Comprehensive Review on Synthesis and Recent Advances, Pharmaceutics 2018, 10, 118.
She et al., Functionalization of Hollow Mesopouous Silica Nanoparticles for Improved 5-FU Loading, Journal of Nanomaterials vol. 2015, Article ID 872035, 9 page (Year 2015).

* cited by examiner

TUNABLE PROCESS FOR SILICA CAPSULES/SPHERES PREPARATION AND THEIR USE

CROSS REFERENCE TO RELATED APPLICATIONS

This application is a National Stage application of PCT/CA2019/051465, filed Oct. 16, 2019, which claims the benefit of U.S. Provisional Application 62/746,444, filed Oct. 16, 2018, both of which are incorporated by reference in their entirety herein.

FIELD OF DISCLOSURE

The disclosure relates to porous and non-porous silica capsules (capsules in capsule or core-shell capsules), porous microspheres, as well as their direct phase emulsification process without surfactant and their use.

BACKGROUND

The encapsulation of oil and liposoluble actives in submicron/microparticles is considered a high-potential technology for many applications. These actives are added to consumer products in the cosmetic, cosmeceutical, dermatological, pharmaceutical, food, and chemical industry to produce high added value materials. Various oils and numerous liposoluble compounds are promising candidates to be sequestered, such as vitamins, drugs, essential oils, fragrance, perfumes, flavor, aroma, dyes, sunscreen, and natural oils extracted from vegetal or animal grease. Silica based sub-micron/microparticles offer high surface area, suitable cost, versatile compositions, thermal/chemical stability, inertness, and desirable innocuousness. Amorphous silica is also Generally Recognized As Safe (GRAS) by the Food and Drug Administration (FDA).

Therefore, it is highly demanded to develop an efficient process, which can produce different types of silica sub-micron/microparticles loaded with liposoluble actives.

SUMMARY OF THE DISCLOSURE

One aspect relates to a process of preparation of spheroidal organosiloxane particle comprising the steps as defined herein.

A further aspect relates to a spheroidal organosiloxane particle as defined herein.

A further aspect relates to a method for applying and/or releasing a liposoluble active/payload comprising the steps as defined herein.

BRIEF DESCRIPTION OF THE FIGURES

The illustrations of the examples corresponding figures are listed as bellow.

DETAILED DESCRIPTION

Figure 1:
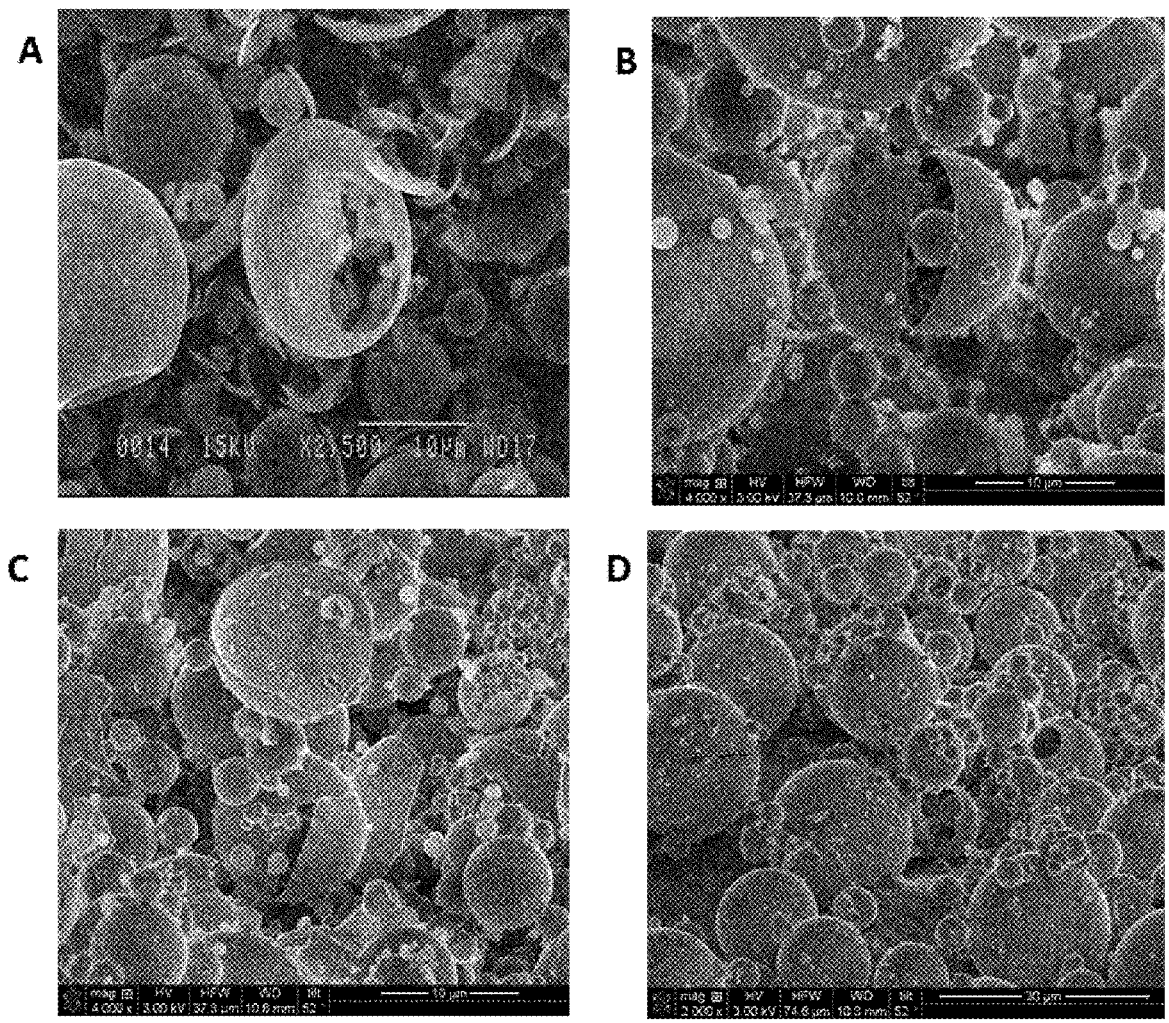
FIG. 1. SEM images of the examples of core-shell sub-micron/microcapsules in microcapsules containing different molar ratio of C1-TES and TEOS. A) Example 1-1 (scale bar=10 μm), B) Example 1-2 (scale bar=10 μm) and C) Example 1-3 (scale bar=10 μm), D) Example 1-4 (scale bar=30 μm).

The morphology of the developed silica particles varies from non-porous spheroidal microcapsules to highly porous network assembled microspheres. The structure and the porosity of the particles can be tailored by controlling the silica precursors as well as the nature of the encapsulated oil. The non-porous spheroidal microcapsules are characterized by their surprising ability to prevent leaking of an encapsulated oil and/or payload within as well as their protective effect on the entrapped actives against premature leaching, while the porous microspheres have the ability to ensure the progressive leaching of the entrapped actives.

This invention can also be used to entrap a variety of compounds, such as vitamin A or cannabinoids without using the harmful/toxic preservatives. It can also be used for sequestering other liposoluble cosmetic actives, such as essential oil, fragrances, perfumes, as well as cosmeceutical, pharmaceutical, and other liposoluble chemical actives.

The physiochemistry and morphology of silica particles (e.g. porous or non-porous, capsules or spheres) play a crucial role in determining their use in the field of actives encapsulation and liberation. For example, non-porous capsules are dedicated to applications where the actives are released under mechanical pressure. In another hand, porous particles are generally designed to ensure the release of entrapped actives in a controlled and progressive manner (i.e. according to certain kinetic parameters).

Furthermore, encapsulation of actives in silica particles is very advantageous in simplifying formulation process, protecting unstable actives, limiting actives premature release, or achieving better liberation rate. For instance, this technology can be applied to protect vitamin A (retinol) from degradation and/or oxidation from light, air humidity etc., without using the harmful preservative (such as butylated hydroxytoluene-BHT or butylated hydroxyanisole-BHA) and toxic ingredients.

The present invention describes an emulsion process to encapsulate the actives into 5 types of spheroidal silica particles by varying the nature and the content of either the silica precursors and/or the encapsulated oil in a one pot process without the use of surfactant. These 5 types of spheroidal silica particles are: A) non-porous core-shell spheroidal sub-micron/microcapsules in spheroidal microcapsules, B) non-porous core-shell spheroidal sub-micron/microcapsules, C) porous core-shell spheroidal sub-micron/microcapsules in spheroidal microcapsules, D) porous core-shell sub-micron/microcapsules, and E) porous sub-micron/microspheres.

As used herein, "non-porous" refers to a material not substantially porous showing a BET surface area less than 100 m$^2$·g$^{-1}$ evaluated by N$_2$-physisorption. The N$_2$-physiorptions were done with Autosorb Quantachrome® ASiQwin™ Instruments iQ2 v3.01 at 77 K. The collected data were analyzed using the multi-point Micropore BET iQ2 to get the surface area. The pore size was obtained from the maxima of the pore size distribution curve calculated by non-local density functional theory (NLDFT). The pore volume data were obtained from NLDFT method cumulative pore volume.

The non-porous capsules are also considered as "leakless particles" characterized by their leakproofness and their protective effect on the entrapped actives against premature leaching. During the storage period, these particles protect the encapsulated active from oxidation and/or release in a formulation or in slurry. Moreover, these particles allow the liberation of the active when appropriate strengths are applied.

As used herein, "porous" refers to a material substantially porous showing a BET surface area more than 100 m2·g-1 evaluated by N2-physisorption. The N2-physiorptions were done with a Micrometrics TriStar™ 3000 V4.01 and Micrometrics TriStar™ 3020 V3.02 at 77 K. The collected data were analyzed using the standard Brunauer-Emmett-Teller (BET) to get the surface area. The pore size was obtained from the maxima of the pore size distribution curve calculated by Barrett-Joyner-Halenda (BJH) method using the desorption branch of the isotherm.

The porous microparticles (microcapsules and microspheres) are also considered as "controlled-release particles" characterized by their ability to liberate the entrapped active in a controlled manner. The liberation of the active can be controlled by varying the surface area, pore volume, pore diameter, and/or the polarity of the particles.

The expression oil-in-water emulsion (O/W) is well known to the skilled practitioners and refers to a mixture of at least two immiscible fluids (oil(s) and water), wherein the particles of the oil phase (the dispersed phase) are dispersed as small spheroidal droplets within the water phase (the dispersant phase).

As used herein, the "spheroidal silica particle" refer to spheroidal silica-based particle, which has a sub-micron-size of 100 nm to 1 µm and/or micron-sized of 1 µm to 200 µm.

As used herein, the "non-porous core-shell spheroidal sub-micron/microcapsules in spheroidal microcapsule" refers to a spheroidal particle characterized by one or more small non-porous core-shell spheroidal sub-micron/microcapsules which are surrounded by a non-porous solid layer, named shell (i.e. one or more non-porous core-shell spheroidal sub-micron/microcapsules are encapsulated in one microcapsule). In one embodiment, the "non-porous core-shell spheroidal sub-micron/microcapsule" is a spheroidal particle characterized by a core which comprises a liposoluble payload encapsulated by a non-porous shell. This particle is named "Type A particle".

As used herein, the "non-porous core-shell spheroidal sub-micron/microcapsule" refers to a spheroidal particle characterized by a core which comprises a liposoluble payload encapsulated by a non-porous shell. This particle is named "Type B particle".

As used herein, the "porous core-shell spheroidal sub-micron/microcapsules in spheroidal microcapsule" refers to a spheroidal particle characterized by one or more small porous core-shell spheroidal sub-micron/microcapsules which are surrounded by a porous solid layer, named shell (i.e. one or more porous core-shell spheroidal sub-micron/microcapsules are encapsulated in one microcapsule). In one embodiment, the "porous core-shell spheroidal sub-micron/microcapsule" is a spheroidal particle characterized by a core which comprises a liposoluble payload encapsulated by a porous shell. This particle is named "Type C particle".

As used herein, the "porous core-shell spheroidal sub-micron/microcapsule" refers to a spheroidal particle characterized by a core which comprises a liposoluble payload encapsulated by a porous shell. This particle is named "Type D particle".

As used herein, the "porous sub-micron/microsphere" refers to a spheroidal porous solid characterized by the encapsulation of a liposoluble payload throughout the porosity of the sub-micro/microsphere. This particle is named "Type E particle".

As used herein, the "silica precursors" refer to either a mono(silane) compound containing one silicon atom of formula $R_{4-x}Si(L)_x$ or to a dipodal silanes compound containing two silicon atoms of formula $(L)_3Si—R'—Si(L)_3$, wherein:

R: is an organic residue of mono(silane) compound selected from the alkyl, alkenyl, alkynyl, alicyclic, aryl, and alkyl-aryl groups, wherein each of said residues can be optionally and independently substituted by one or more halogen atoms, glycidyloxy-, —OH, —SH, polyethylene glycol (PEG), —N$(R_a)_2$, —N$^+(R_a)_3$;

L: is a halogen atom, or an acetoxide group (—O—C(O)$R_a$), or an alkoxide group (O$R_a$);

R': is an organic residue linking the two silane units of a dipodal silanes compound. This organic residue is selected from the alkyl, alkenyl, alkynyl, alicyclic, aryl, and alkyl-aryl groups. Each of said residues is optionally and independently substituted by a halogen atom, —OH, —SH, —N(Ra)$_2$, —N$^+$(Ra)$_3$; $R_a$ can be hydrogen, alkyl, alkenyl, alkynyl, alicyclic, aryl and alkyl-aryl;

X: is an integer of 1 to 4 or alternatively x is an integer of 1 to 3.

The silica precursors are selected so as to be able to form a network of Si—O—Si bonds. The silica precursors include one or more of said compounds of formula $R_{4-x}Si(L)_x$ or of formula $(L)_3Si—R'—Si(L)_3$.

As used herein, the "organosiloxane" refers to an ORganic MOdified SILica network (ORMOSil).

In one embodiment, the silica precursor is a silicon alkoxide such as tetra-alkoxysilane, monoalkyl-trialkoxysilane, dialkyl-dialkoxysilane, or bis(trialkoxysilyl)bridged silane. In a further embodiment the silica precursor is a mixture of silicon alkoxides, such as tetra-alkoxysilane and/or monoalkyl-trialkoxysilane, and/or dialkyl-dialkoxysilane and/or a bis-(trialkoxysilyl) bridged silane.

In one embodiment, the silica precursor is a mixture of silicon alkoxide comprised of two or more monoalkyl-trialkoxysilanes, dialkyl-dialkoxysilanes, trialkyl-alkoxysilanes, bis(trialkoxysilyl)bridged silanes and tetra-alkoxysilanes.

In one embodiment, the alkyl and alkoxy residues of the silicon alkoxide are independently straight, cyclic or branched alkyls that may or may not contain unsaturation or substituted groups and comprise from 1 to 18 carbon atoms, alternatively from 1 to 10 carbon atoms, alternatively from 1 to 8 carbon atoms, alternatively from 1 to 2 carbon atoms and alternatively 1 carbon atom.

In one embodiment, the monoalkyl-trialkoxysilanes RSi$(L)_3$ comprise one alkyl, and the trialkoxy can be a triethoxy or a trimethoxy group.

In one embodiment, the dialkyl-dialkoxysilanes $R_2Si(L)_2$ comprise two alkyls, and the dialkoxy can be a diethoxy or a dimethoxy group.

In one embodiment, the trialkyl-alkoxysilanes $R_3SiL$ comprise three alkyls, and the alkoxy can be an ethoxy or a methoxy group.

In one embodiment, the bis(trialkoxysilyl)bridged silanes $(L)_3Si—R'—Si(L)_3$ comprise R' organic moiety which is straight, cyclic, branched alkyl or alkenyl groups of 2 to 18 carbon atoms, or aryl, or substituted aryl group, and the trialkoxy can be a triethoxy or a trimethoxy group.

As used herein, the "hydrolytic media" refers to the media, which favor the formation of silanol function Si—OH produced from the hydrolysis of the silica precursors. Examples of such media include aqueous media, such as water, optionally mixed with a water miscible organic solvent, such as ethanol or THF and an inorganic acid such as HCl, $H_3PO_4$, $H_2SO_4$, $HNO_3$. Preferably the concentration of the hydrolytic media is form 0.01 mol·L$^{-1}$ to 0.05 mol·L$^{-1}$ and preferentially, the inorganic acid is HCl.

As used herein, the "condensation catalyst" refers to any reagent known in the art of favoring the polycondensation of forming siloxane Si—O—Si bonds.

In one embodiment, the condensation catalyst was added to achieve the final pH in the suspension at about 9.0 to 11.5. The condensation catalyst can be, but not limited to, $NH_4OH$, NaOH, KOH, LiOH, Ca(OH)$_2$, NaF, KF, TBAF, TBAOH, TMAOH, triethanol amine (TEA), triethyl amine, primene, L-lysine, aminopropylsilane.

In one embodiment, the condensation catalyst is concentrated $NH_4OH$. In one embodiment, the condensation catalyst is NaOH.

As used herein, the expression "dispersed phase" refers to the mixture of the pre-condensed silica precursors with the actives/payloads. Pre-condensed silica precursors are obtained by the partial condensation of the pre-hydrolyzed silica precursors by evaporating the volatile solvents present in the hydrolytic media. Pre-hydrolyzed silica precursors are obtained by the partial hydrolysis or by the complete hydrolysis of the L group of $R_{4-x}Si(L)_x$ or $(L)_3Si—R'—Si(L)_3$ in the hydrolytic media.

As used herein, the expression "surfactant" refers to any known surfactant other than amphiphilic silanes. Alternative names used in the art for surfactant may also be surface-active agent, wetting agent, emulsifier, detergent.

As used herein, the expression "continuous phase" refers to the solvents known in the art of having opposite polarity compared to pre-condensed silica precursors to produce direct phase emulsion (oil in water).

In one embodiment, the continuous phase is water.

In one embodiment, the weight ratio of the continuous phase to the dispersed phase containing the pre-condensed silica precursors is from 2.5 to 15, preferably from 3.35 to 6.70.

As used herein, the expression "emulsion process" refers to a process that involves a piece of laboratory or industrial equipment used to mix two or more liquids that are normally immiscible, resulting in a dispersion of droplets (dispersed phase) in a volume of continuous phase.

As used herein, the expression "active" refers to cosmetic, cosmeceutical, dermatological, pharmaceutical, perfume, or flavoring ingredients. The actives are preferably insoluble in the continuous phase. The actives can be used in both, solid and liquid form.

As used herein, the expression "payload" refers to a composition which comprises one or more actives. The payload is designed to stabilize the sensitive active(s) and/or dissolve the active(s) and/or optimize the active(s) release and/or influence the surface area and the porosity, as well as to control the type of spheroidal silica particles. The payloads are preferably insoluble in the continuous phase. The payloads can be in both solid and liquid forms. They can be incorporated by solubilization, dispersion or emulsification in the pre-hydrolyzed or pre-condensed silica precursors.

In one embodiment, the payload's compositions can consist of oil, of a mixture of different oils, of a hydrophobic/liposoluble compound or of a mixture of hydrophobic/liposoluble compounds; the payload can be an active used in its pure form or an active which is dissolved/diluted/dispersed/mixed in oil (i.e. the adequate oil used to the active to sequester).

In one embodiment, the oil is a triglyceride type oil which refers to a substance composed of molecules with hydrophobic properties. These molecules are mainly composed of triglycerides which are esters derived from a molecule of glycerol and three long-chain fatty acids. The long-chain fatty acids can be poly-unsaturated $C_{12}$-$C_{22}$ acids which may be monounsaturated (e.g. oleic), diunsaturated (e.g. linoleic) or polyunsaturated (with three or more double bonds) such as linolenic acid, eicosapentaenoic acid (EPA) or docosahexaenoic acid (DHA). The long-chain fatty acids can be saturated $C_8$-$C_{20}$ acids (e.g. caprylic acid or capric acid).

In one embodiment, the oil is a mixture of unsaponifiable saturated compounds comprising or consisting essentially of alkanes, iso-alkanes, or cycloalkanes, such as alkanes, iso-alkanes, or cycloalkanes from 8 to 50 carbon atoms.

In one embodiment, the oil is the squalene, an unsaturated triterpene hydrocarbon compound comprising 30 carbon atoms.

In one embodiment, the oil is caprylic capric triglyceride, sunflower oil, coconut oil, olive oil, soybean oil, cashew oil, peanut oil, pine nut oil, argan oil, sunflower oil, avocado oil, beeswax, castor wax, wool wax, carnauba wax, soy wax, mineral waxes, shea butter, cocoa butter, silicon oil, mineral oil or any other dispersant meeting the criteria of this invention or mixture thereof. In one embodiment, the payload is a mixture of two or more oil.

In one embodiment, the active is vitamin A in the form of all-trans-retinol (retinol), retinol derivatives such as retinyl acetate, propionate, and palmitate esters (vitamin A esters), and extracts containing retinol. The active can be in solid state or solubilised in oil.

Harmful/toxic preservatives are generally used for Vitamin A formulation, such as butylated hydroxytoluene (BHT, butylated hydroxyanisole (BHA), or tertiary butylhydroquinone (TBHQ) which are known for their high antioxidant property. In one embodiment, the present disclosure provides a process and entrapment in porous and non-porous silica capsules in a non-toxic way (i.e. without the above harmful/toxic preservatives). This refers to the entrapment of vitamin A without using harmful/toxic preservatives. Representative non-toxic preservatives used are tocopherol (alpha-tocopherol, beta-tocopherol, gamma-tocopherol, delta-tocopherol and mixture thereof) and its derivatives (tocopheryl acetate), ascorbic acid, ascorbyl plamitate, citric acid, coenzyme Q10 (ubiquinol), hesperetin, beta-glucan, carotenes, lycopene, and the like.

In one embodiment, the payload is all-trans-retinol mixture oil which refers to all-trans-retinol solid (active) dissolved in adequate oil and stabilised by one or more antioxidants under inert conditions.

In one embodiment, the weight concentration of all-trans-retinol in payload (all-trans-retinol mixture oil) is from 0% to 50% (preferably, 5-30%). In the same embodiment, the weight concentration of the antioxidant in payload is from 0.1% to 50% (preferably, 2-40%) In the same embodiment, the weight concentration of oil is from 0% to 99% (preferably, 35-90%).

In one embodiment, the encapsulated retinol can be a commercially available retinol containing oil. For example, it is Retinol 15D or Retinol 10S of BASF.

In one embodiment, the weight concentration of all-trans-retinol in payload (all-trans-retinol mixture oil) is from 5% to 50% (based on the weight of the payload). The payload is then combined with pre-condensed silica precursors at a weight ratio from 25% to 80%. The weight concentration of all-trans-retinol in the final spheroidal particles is from 1% to 40% (based on the total mass of the spheroidal microparticles excluding the water content).

In one embodiment, the active is a cannabinoid, a mixture of cannabinoids or extract of Cannabaceae biomass, wherein said cannabinoids are but not limited to tetrahydrocannabinol, cannabidiol, cannabigerol, iso-tetrahydrocannabinol, cannabinol. The active cannabinoid can be in solid state or solubilised in oil.

In one embodiment, the payload is cannabinoid, a mixture of cannabinoids or extract of Cannabaceae biomass, mixed with adequate oil and stabilised by one or more antioxidants under inert conditions.

In one embodiment, the payload is cannabinoid, a mixture of cannabinoids or extract of Cannabaceae biomass, mixed with all-trans-retinol solid dissolved in adequate oil and stabilised by one or more antioxidants under inert conditions. In the same embodiment, the weight concentration of cannabinoid, a mixture of cannabinoids or extract of Cannabaceae biomass, in payload is from 0% to 99%. In the same embodiment, the weight concentration of the all-trans-retinol mixture oil) is from 0% to 50%. In the same embodiment, the weight concentration of the antioxidant in payload is from 0.1% to 50%. In the same embodiment, the weight concentration of oil is from 0% to 99% (preferably, 35-90%).

In one embodiment, the payload is then combined with pre-condensed silica precursors at a weight ratio from 25% to 80%. The weight concentration of cannabinoid, a mixture of cannabinoids or extract of Cannabaceae biomass in the final spheroidal particles is from 1% to 40% (based on the total mass of the spheroidal microparticles excluding the water content).

In one embodiment, the payload is an essential oil and/or a perfume and/or a fragrance used in its pure form or diluted/mixed with at least one oil. These actives, encapsulated in the spheroidal particles, are hydrophobic molecules or mixture of molecules forming an oily liquid with a scent. The fragrance contained in the spheroidal particles can be a synthetic perfume or a fragrance extracted from flowers or mixture thereof. For example, the active can be α-pinene, D-limonene, geraniol, bornyl acetate, black spruce, grapefruit seed extract, and the like.

In one embodiment, the payload is a flavor and/or aroma active used in its pure form or dissolved/diluted/dispersed/mixed with at least one oil. For example, the active is menthol, isoamyl acetate, and the like.

In one embodiment, the active is a cooling or heating agent used in its pure form or dissolved/diluted/dispersed/mixed with at least one oil. The quantity of said cooling or heating agents depends of legal limit of each ingredient. For example, the cooling agent is the menthol or menthyl lactate, and the heating agent is the capsaicin, and the like.

In one embodiment, the active is a sunscreen compound used in its pure form or dissolved/dispersed/mixed with at least one oil. Sunscreen active compounds can perform their function of screening out harmful UV radiations between about 290 and about 400 nm while they are encapsulated. For example, the active is an inorganic compound such as the titanium dioxide nanoparticles (1-5 nm). In another embodiment, the active is 2-ethylhexyl methoxycinnamate, generally known as octyl methoxycinnamate.

In one embodiment, the weight concentration of active in the final product is from 1% to 95%, preferably from 20% to 70% (based on the total weight of the spheroidal particles excluding the water content).

In one embodiment, when the active is dissolved/diluted/mixed in oil(s) the weight concentration of active in payload before encapsulation is from 5% to 50%. The payload is then combined with pre-condensed silica precursors at the weight ratio from 25% to 70%. The weight concentration of active in the final spheroidal particles is from 1.25% to 35% (based on the total mass of the spheroidal particles excluding the water content).

The trapped actives/payloads quantity is determined by analytical methods, such as high-performance liquid chromatography (HPLC), (GC-FID), or thermogravimetric analysis (TGA). The loading capacity is actives/payloads-dependent.

The loading capacity is up to 15 wt %, with a sequestration yield up to 100%. In one embodiment, the loading capacity is up to 50 wt %, with a sequestration yield up to 100%. In one embodiment, the loading capacity is up to 95 wt %, with a sequestration yield up to 100%.

The general process of preparation of organosiloxane spheroidal particles comprises: 1) preparing pre-hydrolyzed silica precursors by separately hydrolyzing at least one silica precursor in the hydrolytic media. In one embodiment, all the pre-hydrolyzed silica precursors are combined into one container; 2) preparing pre-condensed silica precursors, optionally by removing a part or totality of the volatile solvents, such as from the hydrolytic media; 3) preparing and/or adding the actives/payloads to the mixture of the step 2; 4) emulsifying, in absence of a surfactant, the dispersed phase of the step 3) in a continuous phase; 5) adding to the emulsion of the step (4) a condensation catalyst; 6) optinally aging the suspension obtained from step 5; 7) Optionally, adding an additional layer of silica on the particles to increase even more the resistance of the spheroidal particles and/or to add an additional function to the external surface of the particles; and 8) optionally isolating, washing, drying, and/or storing the final spheroidal silica particles.

In the same embodiment, at room temperature, all the silica precursors are hydrolyzed independently with vigorous agitation in the hydrolytic media at a stirring rate of 500 rpm at least for minimum 1 hour and then combined into one container. (step 1)

Pre-hydrolyzed silica precursors are obtained by the partial hydrolysis (about 0.5 water mol equivalent to about 2.0 water mol equivalent) or by the complete hydrolysis of the L group of $R_{4-x}Si(L)_x$ or $(L)_3Si—R'—Si(L)_3$ in the hydrolytic media. (step 1)

In the same embodiment, to prepare the pre-condensed silica precursors, the desired quantity of volatile solvents in the hydrolytic media can be removed by: i) evaporation under reduced pressure with rotary evaporator from room temperature to ° C. or ii) distillation at the preferred temperature from 80 to 120° C. Lower and higher temperature can be applied if it is needed. (step 2)

In the same embodiment, the active/payload is incorporated by solubilization, dispersion or emulsification in the pre-hydrolyzed or pre-condensed silica precursors. In another embodiment, the active/payload or mixture of thereof is mixed in an oily solvent under inert atmosphere (e.g. argon) before adding to the pre-condensed silica precursors. (step 3)

In the same embodiment, the emulsification of the dispersed phase in the continuous phase can be realized with a rotor-stator homogenizer which generates stable microdroplets. Typically, the homogenizer speed is about 1500 rpm to 5000 rpm. Preferably, from 3000 to 3500 rpm. (step 4)

The size of the spheroidal particles is tailored by the emulsification method. The rotor-stator homogenizer induces the formation of particles with an average diameter generally between 100 nm and 200 μm. The size of the spheroidal particles can be also be tailored by selecting other parameters, such as, the ratio of continuous phase to dispersed phase. The higher the ratio is, the smaller the spheroidal particles are. The speed of the rotor-stator homogenizer is important to consider regarding the size of spheroidal particles. The higher the speed is, the smaller the spheroidal particles are.

In the same embodiment, during the emulsification, the condensation catalyst is added to the suspension and the emulsification process is maintained from 30 seconds to 30 minutes, preferably 45 seconds. The condensation catalyst is added to reach pH of the suspension at the range of 7.0-12.0, preferably, at the range of 9.0-11.5. (step 5)

In the same embodiment, the obtained suspension is aged at room temperature or at temperatures from 40° C. to 90° C., and/or under inert atmosphere (e.g. nitrogen or argon), and/or in the absence of light, with stirring or shaking to maintain the stable suspension and avoid aggregation for 12 to 24 h. (step 6)

In the same embodiment, after the formation of spheroidal silica particles, extra silica precursors (e.g. TEOS, organosilanes) can be added to form an additional layer of silica on the particles to increase even more the resistance of the spheroidal particles and/or to add an additional function to the external surface of the spheroidal silica particles. (step 7)

In one embodiment, the spheroidal organosiloxane particles can be isolated by vacuum filtration. The spheroidal particles can be washed using a solvent with the least solubility for the actives/payloads to avoid leaching (e.g., water, diluted ascorbic acid solution or diluted sodium ascorbate solution (1 g·L$^{-1}$)). Finally, the resulting material can be dried at room temperature or up to 70° C., under air atmosphere or under inert atmosphere e.g. nitrogen or argon depending on the properties of the actives/payloads, at atmospheric pressure or under reduced pressure for 30 minutes at least. (step 8)

The polarity of the obtained spheroidal particles depends on the composition/nature of the silica precursors and the composition/nature of the payload. In one embodiment, spheroidal particles with both an inner and an external hydrophilic surface are obtained. In another embodiment, spheroidal particles with a hydrophilic external surface and an hydrophobic internal surface are obtained. In further embodiment, spheroidal particles with both an inner and an external hydrophobic surface are obtained. As consequence, the water-dispersible or oil-dispersible spheroidal particles can be obtained.

As used herein, the "water-dispersible" characteristic of particles refers to particles that can be dispersed in aqueous solution even if they are obtained from silica precursors with hydrophobic organic group. This suggests that the hydrophobic organic functional groups in silica precursors tend to be localized more on the inner surface of the particles than on the external surface.

In one embodiment, the polarity of the spheroidal particles can be controlled by the composition of the silica precursors, such as the tetramethoxysilane (TMOS), tetraethoxysilane (TEOS), methyltriethoxysilane (C1-TES), ethyltriethoxysilane (C2-TES), octyltriethoxysilane (C8-TES), the octadecyltriethoxysilane (C18-TES).

In one embodiment, when only TEOS is used as silica precursor the contact angle of the corresponding spheroidal particles is of 0°-40° which indicates the fully hydrophilic outer surface property. In another embodiments, when only C1-TES is used as silica precursor the contact angle of the corresponding spheroidal microspheres is of 135°-140° which indicates the fully hydrophobic outer surface property. In another embodiment, when C1-TES and TEOS are used as silica precursor, the contact angle of the corresponding spheroidal particles is of 40°-90°. In another embodiment, when TEOS and C1-TES and/or C8-TES and/or C18-TES are used as silica precursor, the contact angle of the corresponding spheroidal particles is of 40°-150°. In further embodiments, when C1-TES and C18-TES and TEOS are used as silica precursor with different payload compositions, the contact angle of the corresponding spheroidal particles is of 40°-150°. These results confirm the tunable external surface polarity of these matrices from hydrophilic to hydrophobic (cf. Example 25-1, FIG. 19 and FIG. 20).

To further approve above conclusion, the elemental composition (% Si(2s), % C(1s), % O(1s)) of the outer surface of the spheroidal particles in the first 5 nm in depth was analyzed by X-ray photoelectron spectroscopy (XPS). Indeed, the obtained data (cf. Example 25-2) shown the presence of higher C/Si ratio ($\geq 1.00$) for spheroidal particles with hydrophobic external surface (having a contact angle value more than 100°), compared to the C/Si ratio ($<1.00$) obtained for spheroidal particles with hydrophilic external surface (having a contact angle value less than 90°).

In one embodiment, depending on the nature and the relative content of the sequestered oil, the nature and the relative content of silica precursors, the general process described above leads to the formation of 3 families of spheroidal silica particles: 1) non-porous microcapsules including non-porous core-shell spheroidal sub-micron/microcapsules in spheroidal microcapsules (Type A) and non-porous core-shell spheroidal sub-micron/microcapsules (Type B); 2) porous microcapsules including porous core-shell spheroidal sub-micron/microcapsules in spheroidal microcapsules (Type C) and porous core-shell spheroidal sub-micron/microcapsules (Type D); 3) porous microspheres including porous spheroidal sub-micron/microspheres (Type E).

1) Non-Porous Microcapsules Including Non-Porous Core-Shell Spheroidal Sub-Micron/Microcapsules in Spheroidal Microcapsules (Type A) and Non-Porous Core-Shell Spheroidal Sub-Micron/Microcapsules (Type B)

In one embodiment, non-porous microcapsules have been prepared by using the chemical reagents and procedure as described in the general process.

In one embodiment, the process of preparing non-porous microcapsules is comprised of adding one or more silica precursors, preferably one or two silica precursors.

In one embodiment, the process of preparing non-porous microcapsules is comprised of adding only one silica precursor such as monoalkyl-trialkoxysilane. The monoalkyl-trialkoxysilane is preferentially methyltriethoxysilane (C1-TES) or methyltrimethoxysilane (C1-TMS).

In one embodiment, the process of preparing non-porous microcapsules is comprised of adding a silica precursor that is a mixture of two silicon alkoxides such as tetra-alkoxysilane silane and monoalkyl-trialkoxysilane. The monoalkyl-trialkoxysilane is preferentially C1-TES, ethyltriethoxysilane (C2-TES) and octadecyltriethoxysilane (C18-TES). The molar ratio of monoalkyl-trialkoxysilane/TEOS is 2.5-30.0%/97.5-70.0%.

In one embodiment, the silica precursor is a mixture of C1-TES and TEOS at molar ratio of 5-20%/95-80%.

In one embodiment, the silica precursor is a mixture of C2-TES and TEOS at molar ratio of 5-20%/95-80%, preferably 10%/90%.

In one embodiment, the silica precursor is a mixture of C18-TES and TEOS at molar ratio of 5-20%/95-80%, preferably 10%/90%.

In one embodiment, in the process of preparing non-porous microcapsules the pre-condensed silica precursor is obtained by distillation at 95-105° C. In other embodiment, when the silica precursor is only monoalkyl-trialkoxysilane the pre-condensed silica precursor is obtained by evaporation under reduced pressure with rotary evaporator at 35° C.

In one embodiment, the payload loaded in non-porous microcapsules is vitamin A (active) dissolved in different oils and stabilised by different non-toxic antioxidants, such as tocopherol and its derivatives, ascorbyl palmitate, hesperetin, coenzyme Q10, and the like. The concentration of vitamin A in the payload (all-trans-retinol mixture oil) is from 0 wt % to 50 wt %, preferably from 5% to 30%. The payload is then combined with pre-condensed silica precursors at a weight ratio from 25% to 80%, preferably from 40% to 70%. The weight percent of active in the final non-porous microcapsules obtained is from 0% to 40%, preferably from 2% to 21% (based on the total mass of the non-porous microcapsules excluding the water content).

In one embodiment, the weight concentration of all-trans-retinol in payload (all-trans-retinol mixture oil) is from 0% to 50%, preferably from 5% to 30%). In the same embodiment, the weight concentration of the antioxidant in payload is from 0.1% to 50%, preferably from 2% to 40%) In the same embodiment, the concentration of oil is from 0% to 99%, preferably from 35% to 90%).

In one embodiment, the payload loaded in non-porous microcapsules is cannabinoid, a mixture of cannabinoids or extract of Cannabaceae biomass (actives) mixed or dissolved in different oils. In the same embodiment, the all-trans-retinol can be added in the mixture.

In one embodiment, the payload loaded in non-porous microcapsules is essential oil and/or perfume and/or fragrance (active) used in its pure form. In the final non-porous microcapsules obtained, the weight percent of the active is from 1% to 95%, preferably from 20% to 70% (based on the total mass of the microcapsules excluding the water content). For example, the active is geraniol.

In one embodiment, the payload loaded in non-porous microcapsules is essential oil and/or perfume and/or fragrance (active) dissolved/diluted/mixed with at least one oil, preferably a triglyceride such as caprylic capric triglyceride, sunflower oil, and the like. The active weigh ratio in the payload is from 4% to 50%, preferably 15%. The payload is then combined with pre-condensed silica precursor at a weight ratio from 25% to 70%, preferably 50%. The weight percent of the active in the final non-porous microcapsules is from 1% to 35%, preferably 7.5% (based on the total mass of the non-porous microcapsules excluding the water content).

In one embodiment, the active is α-pinene. In another embodiment, the active is bornyl acetate. In another embodiment, the active is black spruce.

In one embodiment, the payload is a flavor and/or aroma (active) dissolved/diluted/mixed with at least one oil, preferably a triglyceride such as caprylic capric triglyceride, sunflower oil, and the like. The active weigh ratio in the payload is from 5% to 50% before encapsulation, preferably 15%. The payload is then combined with the pre-condensed silica precursors at a weight ratio from 25% to 70%, preferably 50%. The weight percent of the active in the final non-porous microcapsules is from 1.25% to 35%, preferably 7.5% (based on the total mass of the non-porous microcapsules excluding the water content).

In one embodiment, the active is menthol. In another embodiment, the active is isoamyl acetate.

To obtain Type A non-porous core-shell spheroidal sub-micron/microcapsules in spheroidal microcapsules, the active was dissolved/diluted/mixed in triglyceride oil (such as: caprylic capric oil, corn oil, sunflower oil or mixture thereof).

To obtain Type B non-porous core-shell spheroidal microcapsules, the active was dissolved/diluted/mixed in a mixture of saturated compound with high levels of unsaponifiable matter, containing mainly of alkanes and cycloalkanes comprising 18 to 50 carbon atoms such as mineral oil, mineral wax.

The specific BET surface of the non-porous spheroidal microcapsules (Type A and Type B) varies from 0.1 to 100 $m^2 \cdot g^{-1}$, preferably from 0.1 to 20 $m^2 \cdot g^{-1}$.

2) Porous Microcapsules Including Porous Core-Shell Spheroidal Sub-Micron/Microcapsules in Spheroidal Microcapsules (Type C) and Porous Core-Shell Spheroidal Sub-Micron/Microcapsules (Type D)

In one embodiment, porous microcapsules have been prepared by using the chemical reagents and procedure as described the general process.

In one embodiment, the process of preparing porous microcapsules is comprised of adding one or more silica precursors, preferably two silica precursors or three silica precursors.

In one embodiment, the process of preparing porous microcapsules is comprised of adding a silica precursor that is a mixture of two silicon alkoxides such as tetra-alkoxysilane and monoalkyl-trialkoxysilane, or tetra-alkoxysilane and dialkyl-dialkoxysilane, or tetra-alkoxysilane and trialkyl-alkoxysilane, or tetra-alkoxysilane and bis(trialkoxysilyl)bridged silane.

In one embodiment, in the process of preparing porous microcapsules with the mixture of two silica precursors, such as TEOS and monoalkyl-trialkoxysilane. The monoalkyl-trialkoxysilane is preferentially C1-TES, vinyltriethoxysilane (Vy-TES), 3-mercaptopropyl trimethoxysilane (SH-TMS), (3-glycidyloxypropyl)-trimethoxysilane (GP-TMS), phenyltriethoxysilane (Ph-TES), 2-[methoxy(polyethyleneoxy)6,9-propyl]trimethoxysilane (PEG-TMS), 3-(trimethoxysilyl)propyl-N,N,N-trimethylammonium chloride (TMPAS). The molar ratio of monoalkyl-trialkoxysilane/TEOS is 2.5-30%/97.5-70%, preferably 10%/90%.

In one embodiment, in the process of preparing porous microcapsules, the silica precursor is a mixture of TEOS and dialkyl-dialkoxysilanes such as diethyldiethoxysilane (C2-DES). The molar ratio of C2-DES/TEOS is 5-20%/95-80%, preferably 10%/90%.

In one embodiment, in the process of preparing porous microcapsules, the silica precursor is a mixture of TEOS and trialkyl-alkoxysilane such as triethylethoxysilane (C3-ES). The molar ratio of C3-ES/TEOS is 5-20%/95-80%, preferably 10%/90%.

In one embodiment, in the process to prepare porous microcapsules, the silica precursor is a mixture of TEOS and bis(trialkoxysilyl)bridged silane such as 1,2-bis(triethoxysilyl)ethane (BTEE). The molar ratio of BTEE/TEOS is 5-20%/95-80%, preferably 5%/95%.

In one embodiment, the process to prepare porous microcapsules is comprising a mixture of three silica precursors, such as tetra-alkoxysilane and two different monoalkyl-trialkoxysilanes, or tetra-alkoxysilane and one monoalkyl-trialkoxysilanes and one dialkyl-dialkoxysilane, or one tetra-alkoxysilane and one monoalkyl-trialkoxysilanes and one trialkyl-alkoxysilane, or tetra-alkoxysilane and one monoalkyl-trialkoxysilanes and one bis-(trialkoxysilyl)bridged silane, preferably one tetra-alkoxysilane and two different monoalkyl-trialkoxysilanes.

In one embodiment, in the process of preparing porous microcapsules, the silica precursor is a mixture of C1-TEOS with C8-TES and TEOS. The molar ratio of C1-TES/C8-TES/TEOS is 10.0-22.5%/5.0-7.5%/85-70%, preferably 22.5%/7.5%/70%.

In one embodiment, in the process of preparing porous microcapsules, the pre-condensed silica precursor is obtained by distillation at 85-100° C. In another embodiment, when the silica precursor is a mixture of BTEE and TEOS the pre-condensed silica precursor is obtained by evaporation under reduced pressure with rotary evaporator at 35° C.

In one embodiment, the payload loaded in porous microcapsules is vitamin A (active) dissolved in different oils and stabilised by non-toxic antioxidants, such as tocopherol and its derivatives, ascorbyl palmitate, hesperetin and coenzyme Q10. The concentration of vitamin A in payload is from 0 wt % to 50 wt %, preferably from 5 wt % to 30 wt %. The payload is then combined with the pre-condensed silica precursors preferably at a weight ratio from 25% to 80%, preferably from 40% to 70%. The weight percent of active in the final porous microcapsules is from 0 wt % to 40 wt %, preferably from 2% to 20% (based on the total mass of the porous microcapsules excluding the water content).

In one embodiment, the weight concentration of all-trans-retinol in payload (all-trans-retinol mixture oil) is from 0% to 50%, preferably from 5% to 30%. In the same embodiment, the weight concentration of the antioxidant in payload is from 0.1% to 50%, preferably from 2% to 40%. In the same embodiment, the concentration of oil is from 0% to 99%, preferably from 35% to 90%.

In one embodiment, the payload loaded in porous microcapsules is vitamin A (active) dissolved in different oils and stabilised by more toxic antioxidants, such as BHT or BHA.

In one embodiment, the payload loaded in porous microcapsules is cannabinoid, a mixture of cannabinoids or extract of Cannabaceae biomass (actives) mixed or dissolved in different oils. In the same embodiment, the all-trans-retinol can be added in the mixture.

In one embodiment, the payload loaded in porous microcapsules is essential oil and/or perfume and/or fragrance (active) used in pure form. The weight percent of the active in the final porous microcapsules is from 1% to 95%, preferably from 20% to 70% (based on the total mass of the porous microcapsules excluding the water content).

In other embodiment, the payload loaded in porous microcapsules is essential oil and/or perfume and/or fragrance (active) dissolved/diluted/mixed with at least one oil. The concentration of the active weigh ratio in the payload is from 5% to 50%, preferably from 15% to 50%. The payload is then combined with pre-condensed silica precursors, preferably at a weight ratio of 50%. The weight percent of the active in the final porous microcapsules is from 2.5% to 25%, preferably from 7.5% to 25% (based on the total mass of the porous microcapsules excluting the water content).

In one embodiment, the active is black spruce. In other embodiment, the active is orange essential oil. In another embodiment, the active is grapefruit seed extract.

In one embodiment, the payload loaded in porous microcapsules is flavor and/or aroma (active) dissolved/diluted/mixed with at least one oil. The concentration of the active weigh ratio in the payload is from 5% to 50%, preferably from 15% to 50%. The payload is then combined with pre-condensed silica precursors, preferably at a weight ratio of 50%. The weight percent of the active in the final porous microcapsules is from 2.5% to 25%, preferably from 7.5% to 25% (based on the total mass of the porous microcapsules excluding the water content).

In one embodiment, the payload loaded in porous microcapsules is a sunscreen compound used as dissolved/dispersed/mixed with at least one oil. The weight percent of the active in the final porous microcapsules is from 0.5% to 5%, preferably 2% (based on the total mass of the porous microcapsules excluding the water content). For example, the active is titanium dioxide nanoparticles (1-5 nm).

To obtain Type C porous core-shell spheroidal sub-micron/microcapsules in spheroidal microcapsules, the active was dissolved in triglyceride oil (such as: caprylic capric oil, corn oil, sunflower oil or mixture thereof).

To obtain type D porous core-shell microcapsules the active was dissolved/diluted/mixed in squalene or in a mixture of saturated compound with high levels of unsaponifiable matter, containing mainly of alkanes and cycloalkanes comprising 18 to 50 carbon atoms such as mineral oil or mineral wax.

In one embodiment, the specific BET surface of the porous spheroidal microcapsules (Type C and Type D) varies from 100 to 1500 $m^2 \cdot g^{-1}$ preferably from 150 $m^2 \cdot g^{-1}$ to 1000 $m^2 \cdot g^{-1}$ 3) Porous Microspheres Including Porous Spheroidal Sub-Micron/Microspheres (Type E)

In one embodiment, porous microspheres have been prepared by using the chemical reagents and procedure as described in the general process.

In one embodiment, the process of preparing porous microspheres is comprised of adding one silica precursor or more than one silica precursors, preferably one silica precursor, or two silica precursors, or three silica precursors.

In one embodiment, the process of preparing porous microspheres is comprised of adding only one silica precursor that is tetra-alkoxysilane or monoalkyl-trialkoxysilane.

In one embodiment, the process of preparing porous microspheres is comprised of adding a silica precursor that is a mixture of two silicon alkoxides, such as tetra-alkoxysilane and monoalkyl-trialkoxysilane, or tetra-alkoxysilane and dialkyl-dialkoxysilane, or tetra-alkoxysilane and trialkyl-alkoxysilane, or tetra-alkoxysilane and bis(trialkoxysilyl)bridged silane.

In one embodiment, in the process of preparing porous microspheres, the silica precursor is a mixture of TEOS and monoalkyl-trialkoxysilane, such as C1-TES, C2-TES, Vy-TES, SH-TMS, GP-TMS, Ph-TES, PEG-TMS, TMPAS. The molar ratio of monoalkyl-trialkoxysilane/TEOS is 5-60%/95-40%.

In one embodiment, the silica precursor is a mixture of octyltriethoxysilane (C8-TES) and TEOS. The molar ratio of C8-TES/TEOS is 5-60%/95-40%, preferably 10%/90%.

In one embodiment, in the process to prepare porous microspheres, the silica precursor is a mixture of TEOS and dialkyl-dialkoxysilane such as dimethyldiethoxysilane (C2-DES). The molar ratio of C2-DES/TEOS is 5-60%/95-40%, preferably 30%/70%.

In one embodiment, in the process to prepare porous microspheres, the silica precursor is a mixture of TEOS and trialkyl-alkoxysilane such as triethylethoxysilane (C3-ES). The molar ratio of C3-ES/TEOS is 5-60%/95-40%, preferably 30%/70%.

In one embodiment, in the process to prepare porous microspheres, the silica precursor is a mixture of TEOS and bis(trialkoxysilyl)bridged silane (BTEE). The molar ratio of BTEE/TEOS is 5-60%/95-40%, preferably 15%/70%.

In one embodiment, the process to prepare porous microspheres is comprising adding a silica precursors that is a mixture of three silicon alkoxides, such as one tetra-alkoxysilane and two different monoalkyl-trialkoxysilanes; or one tetra-alkoxysilane and one monoalkyl-trialkoxysilanes and one dialkyl-dialkoxysilane; or tetra-alkoxysilane and one monoalkyl-trialkoxysilanes and one trialkyl-alkoxysilane; or tetra-alkoxysilane and one monoalkyl-trialkoxysilanes and one bis(trialkoxysilyl)bridged silane; preferably, one tetra-alkoxysilane and two different monoalkyl-trialkoxysilanes.

In one embodiment, in the process of preparing porous microspheres, the silica precursor is a mixture of C1-TES with C8-TES and TEOS. The molar ratio of C1-TES/C8-TES/TEOS is 5.0-30%/2.5-10.0%/92.5-60%, preferably 10.0-22.5%/5.0-7.5%/85.0-70.0%.

In one embodiment, the silica precursor is a mixture of C1-TES with C18-TES and TEOS. The molar ratio of C1-TES/C18-TES/TEOS is 5.0-30%/2.5-10.0%/92.5-60%, preferably 10.0-20%/2.5-5.0%/87.5-75%.

In one embodiment, in the process of preparing porous microspheres, the pre-condensed silica precursor is obtained by distillation at 85-100° C. In other embodiment, in the process of preparing porous microspheres with BTEE and TEOS the pre-condensed silica precursor is obtained by evaporation under reduced pressure with rotary evaporator at 35° C.

In one embodiment, the payload loaded in porous microspheres is vitamin A (active) dissolved in different oils and stabilised by non-toxic antioxidants, such as tocopherol and its derivatives, ascorbyl palmitate, hesperetin, coenzyme Q10, and the like. Preferably, the weight concentration of vitamin A in the payload (all-trans-retinol mixture oil) is 0-50%, preferably 5-30%. The payload is then combined with pre-condensed silica precursors preferably at a molar ratio of 25-80%, preferably 40-70%. The weight percent of active in the final porous microspheres is from 0% to 40%, preferably from 1.25% to 21% (based on the total mass of the porous microspheres excluding the water content). In one embodiment, the weight concentration of all-trans-retinol in payload (all-trans-retinol mixture oil) is from 0% to 50%, preferably from 5% to 30%. In the same embodiment, the weight concentration of the antioxidant in payload is from 0.1% to 50%, preferably from 2% to 40%. In the same embodiment, the concentration of oil is from 0% to 99%, preferably from 35% to 90%.

In one embodiment, the payload loaded in porous microcapsules is vitamin A (active) dissolved in different oils and stabilised by more toxic antioxidants, such as BHT or BHA.

In one embodiment, the payload loaded in porous microspheres is cannabinoid, a mixture of cannabinoids or extract of Cannabaceae biomass (actives) mixed or dissolved in different oils. In the same embodiment, the all-trans-retinol can be added in the mixture.

In one embodiment, the payload loaded in porous microspheres is essential oil and/or perfume and/or fragrance (active) used in its pure form. In the final porous microspheres obtained, the weight percent of the active is from 1% to 95%, preferably from 20% to 70% (based on the total mass of the porous microspheres excluding the water content).

In one embodiment, the payload loaded in porous microspheres is essential oil and/or perfume and/or fragrance (active) dissolved/diluted/mixed with at least one oil. Preferably, the active weigh ratio in the payload is 5-50% before encapsulation. The payload is then combined with pre-condensed silica precursors preferably at a weight ratio of 50%. The weight percent of the active in the final porous microspheres obtained is from 2.5% to 25% (based on the total mass of the porous microspheres excluding the water content).

In one embodiment, the active is D-limonene. In another embodiment, the active is geraniol. In another embodiment, the active is black spruce. In another embodiment, the active is gray pine essential. In another embodiment, the active is balsam popular essential oil. In another embodiment, the active is orange essential oil. In another embodiment, the active is grapefruit seed extract.

In one embodiment, the payload loaded in porous microspheres is flavor and/or aroma (active) used in its pure form. In the final porous microspheres obtained, the weight percent of the active is from 20% to 70% (based on the total mass of the porous microcapsules excluding the water content). In another embodiment, the payload loaded in porous microspheres is flavor and/or aroma (active) dissolved/diluted/mixed with at least one oil. Preferably, the active weigh ratio in the payload is 5-50% before encapsulation. The payload is then combined with pre-condensed silica precursors preferably at a weight ratio of 50%. The weight percent of the active in the final porous microspheres obtained is from 2.5% to 25% (based on the total mass of the porous microspheres excluding the water content). For example, the active is menthol. In one embodiment, the active loaded in porous microspheres is a cooling agent. For example, the cooling agent is menthol or menthyl lactate. In another embodiment, the active loaded in porous microspheres is a heating agent. For example, the heating agent is capsaicin. The quantity of the active depends of legal limit of each ingredient.

In one embodiment, the payload loaded in porous microspheres is a sunscreen compound used as dissolved/dispersed/mixed with at least one oil. The weight percent of the active in the final porous microcapsules is from 0.5% to 5%, preferably 2% (based on the total mass of the porous microcapsules excluding the water content). For example, the active is titanium dioxide nanoparticles (1-5 nm).

To obtain Type E porous microspheres, the active was used pure or dissolved/diluted in triglyceride oil (such as: caprylic capric oil, corn oil, sunflower oil or mixture thereof), in squalene, or mixture thereof.

In one embodiment, the specific BET surface of the porous microspheres varies from about 100 to about 1500 $m^2 \cdot g^{-1}$, preferably from about 150 $m^2 \cdot g^{-1}$ to about 1000 $m^2 \cdot g^{-1}$.

Non-Porous Microcapsules Including Non-Porous Core-Shell Spheroidal Sub-Micron/Microcapsules in Spheroidal Microcapsules (Type A) and Non-Porous Core-Shell Spheroidal Sub-Micron/Microcapsules (Type B)

In one embodiment, the payload loaded in non-porous microcapsules is vitamin A in the form of all-trans-retinol (active) dissolved in different oils preferably a triglyceride such as caprylic capric triglyceride, and stabilised by non-toxic antioxidants, such as tocopherol. The payload is preferably all-trans-retinol and tocopherol and caprylic capric triglyceride at a weight ratio of 5-30%/10-40%/85-30%, preferably 10-20%/20-40%/70-40%. The pre-condensed silica precursors are preferably pre-condensed C1-TES and TEOS, and preferably at a molar ratio of 5-20%/95-80%, preferably 10%/90%. The payload is then combined with pre-condensed silica precursors at a weight ratio from 25% to 80%, preferably from 40% to 70%. The weight percent of active in the final non-porous microcapsules is from 1.25% to 24%, preferably 2.5-14% (based on the total mass of the non-porous microcapsules excluding the water content).

In one embodiment, the payload loaded in non-porous microcapsules is vitamin A in the form of all-trans-retinol (active) dissolved in different oils preferably a mineral oil, and stabilised by non-toxic antioxidants, such as tocopherol. The payload is preferably all-trans-retinol and tocopherol and mineral oil at a weight ratio of 5-30%/10-40%/85-30%, preferably 10-20%/20-40%/70-40%. The pre-condensed silica precursors are preferably pre-condensed C1-TES and TEOS, and preferably at a molar ratio of 5-20%/95-80%, preferably 10%/90%. The payload is then combined with pre-condensed silica precursors at a weight ratio from 25% to 80%, preferably from 40% to 70%. The weight percent of active in the final non-porous microcapsules is from 1.25% to 24%, preferably from 2.5% to 14% (based on the total mass of the non-porous microcapsules excluding the water content).

In one embodiment, the payload loaded in non-porous microcapsules is cannabinoid in the form of cannabidiol (active) dissolved in different oils preferably a coconut oil. The payload is preferably cannabidiol and coconut oil at a weight ratio of 5-90%/95-10%, preferably 25%-75%/75%-25%. The pre-condensed silica precursors are preferably pre-condensed C1-TES and TEOS, and preferably at a molar ratio of 5-20%/95-80%, preferably 10%/90%. The payload is then combined with pre-condensed silica precursors at a weight ratio from 25% to 80%, preferably from 40% to 70%. The weight percent of active in the final non-porous microcapsules is from 1.2% to 75%, preferably from 10% to 50% (based on the total mass of the non-porous microcapsules excluding the water content).

In one embodiment, the payload loaded in non-porous microcapsules is cannabinoid in the form of Tetrahydrocannabinol (active) dissolved in different oils preferably a coconut oil. The payload is preferably cannabidiol and coconut oil at a weight ratio of 5-100%/95-0%, preferably 25%-75%/75%-25%. The pre-condensed silica precursors are preferably pre-condensed C1-TES and TEOS, and preferably at a molar ratio of 5-20%/95-80%, preferably 10%/90%. The payload is then combined with pre-condensed silica precursors at a weight ratio from 25% to 80%, preferably from 40% to 70%. The weight percent of active in the final non-porous microcapsules is from 1.2% to 80%, preferably from 10% to 50% (based on the total mass of the non-porous microcapsules excluding the water content).

In one embodiment, the payload loaded in non-porous microcapsules is vitamin A in the form of all-trans-retinol (active), mixed with cannabinoid in the form of cannabidiol (active) dissolved in different oils preferably a mineral oil, and stabilised by non-toxic antioxidants, such as tocopherol. The payload is preferably all-trans-retinol, cannabidiol, tocopherol and mineral oil at a weight ratio of 5-30%/0-15%/45-25%/50-30%, preferably 10-20%/10%/40-20%/40-50%. The pre-condensed silica precursors are preferably pre-condensed C1-TES and TEOS, and preferably at a molar ratio of 5-20%/95-80%, preferably 10%/90%. The payload is then combined with pre-condensed silica precursors at a weight ratio from 25% to 80%, preferably from 40% to 70%. The weight percent of all-trans-retinol in the final non-porous microcapsules is from 1.25% to 24%, preferably from 2.5% to 14% (based on the total mass of the non-porous microcapsules excluding the water content). The weight percent of cannabidiol in the final non-porous microcapsules is from 6.25% to 36%, preferably from 2.5% to 14% (based on the total mass of the non-porous microcapsules excluding the water content).

In one embodiment, the payload loaded in non-porous microcapsules is vitamin A in the form of all-trans-retinol (active) dissolved in different oils preferably a triglyceride such as caprylic capric triglyceride and stabilised by non-toxic antioxidants, such as tocopherol. The payload is preferably all-trans-retinol and tocopherol and caprylic capric triglyceride at a weight ratio of 5-30%/10-40%/85-30%, preferably 10-20%/20-40%/70-40%. The pre-condensed silica precursors are preferably pre-condensed C18-TES and TEOS, and preferably at a molar ratio of 5-20%/95-80%, preferably 10%/90%. The payload is then combined with pre-condensed silica precursors at a weight ratio from 25% to 80%, preferably from 40% to 70%. The weight percent of active in the final non-porous microcapsules is from 1.25% to 24%, preferably 2.5-14% (based on the total mass of the non-porous microcapsules excluding the water content).

In one embodiment, the payload loaded in non-porous microcapsules is essential oil and/or perfume and/or fragrance (active) used in its pure form. The payload is preferably the geraniol. The pre-condensed silica precursors are preferably pre-condensed C1-TES and TEOS, and preferably at a molar ratio of 5-20/95-80%, preferably 10/90%. In the final non-porous microcapsules obtained, the weight percent of the active is from 1% to 95%, preferably from 20% to 70% (based on the total mass of the microcapsules excluding the water content).

In one embodiment, the payload loaded in non-porous microcapsules is essential oil and/or perfume and/or fragrance (active) used in its pure form. The payload is preferably the geraniol. The pre-condensed silica precursors are preferably pre-condensed C18-TES and TEOS, and preferably at a molar ratio of 5-20%/95-80%, preferably 10%/90%. In the final non-porous microcapsules obtained, the weight percent of the active is from 1% to 95%, preferably from 20% to 70% (based on the total mass of the microcapsules excluding the water content).

In one embodiment, the payload loaded in non-porous microcapsules is essential oil and/or perfume and/or fragrance (active) used in its pure form. The payload is preferably the geraniol. The pre-condensed silica precursor is preferably pre-condensed 100% C1-TES. In the final non-porous microcapsules obtained, the weight percent of the active is from 1% to 95%, preferably from 20% to 70% (based on the total mass of the microcapsules excluding the water content).

In one embodiment, the payload loaded in non-porous microcapsules is essential oil and/or perfume and/or fragrance (active) dissolved/diluted/mixed with at least one oil, preferably a triglyceride such as caprylic capric triglyceride. The payload is preferably black spruce active and caprylic capric oil, and preferably at a weight ratio of 5-50%/95-50%, preferably 15%/85%. The pre-condensed silica precursors are preferably pre-condensed C1-TES and TEOS, and preferably at a molar ratio of 5-20%/95-80%, preferably 10/90%. The payload is combined with pre-condensed silica precursor at a weight ratio from 25% to 70%, preferably 50%. The weight percent of the active in the final non-porous microcapsules is from 1.25% to 35%, preferably 7.5% (based on the total mass of the non-porous microcapsules excluding the water content).

In one embodiment, the payload loaded in non-porous microcapsules is essential oil and/or perfume and/or fragrance (active) dissolved/diluted/mixed with at least one oil, preferably a triglyceride such as caprylic capric triglyceride. The payload is preferably α-pinene active and caprylic capric oil, and preferably at a weight ratio of 5-50%/95-50%, preferably 15%/85%. The pre-condensed silica precursors are preferably pre-condensed C1-TES and TEOS, and preferably at a molar ratio of 5-20%/95-80%, preferably 10/90%. The payload is combined with pre-condensed silica precursor at a weight ratio from 25% to 70%, preferably 50%. The weight percent of the active in the final non-porous microcapsules is from 1.25% to 35%, preferably 7.5% (based on the total mass of the non-porous microcapsules excluding the water content).

In one embodiment, the payload loaded in non-porous microcapsules is essential oil and/or perfume and/or fragrance (active) dissolved/diluted/mixed with at least one oil, preferably the mineral oil. The payload is preferably bornyl acetate active and mineral oil, and preferably at a weight ratio of 5-50%/95-50%, preferably 15%/85%. The pre-condensed silica precursors are preferably pre-condensed C1-TES and TEOS, and preferably at a molar ratio of 5-20%/95-80%, preferably 10/90%. The payload is combined with pre-condensed silica precursor at a weight ratio from 25% to 70%, preferably 50%. The weight percent of the active in the final non-porous microcapsules is from 1.25% to 35%, preferably 7.5% (based on the total mass of the non-porous microcapsules excluding the water content).

In one embodiment, the payload loaded in non-porous microcapsules is essential oil and/or perfume and/or fragrance (active) dissolved/diluted/mixed with at least one oil, preferably a triglyceride such as caprylic capric triglyceride. The payload is preferably bornyl acetate active and caprylic capric triglyceride, and preferably at a weight ratio of 5-50%/95-50%, preferably 15%/85%. The pre-condensed silica precursors are preferably pre-condensed C18-TES and TEOS, and preferably at a molar ratio of 5-20%/95-80%, preferably 10/90%. The payload is combined with pre-condensed silica precursor at a weight ratio from 25% to 70%, preferably 50%. The weight percent of the active in the final non-porous microcapsules is from 1.25% to 35%, preferably 7.5% (based on the total mass of the non-porous microcapsules excluding the water content).

In one embodiment, the payload is a flavor and/or aroma (active) dissolved/diluted/mixed with at least one oil, preferably a triglyceride such as caprylic capric triglyceride. The payload is preferably menthol active and caprylic capric triglyceride, and preferably at a weight ratio of 5-50%/95-50%, preferably 15%/85%. The pre-condensed silica precursors are preferably pre-condensed C1-TES and TEOS, and preferably at a molar ratio of 5-20%/95-80%, preferably 10/90%. The payload is combined with pre-condensed silica precursor at a weight ratio from 25% to 70%, preferably 50%. The weight percent of the active in the final non-porous microcapsules is from 1.25% to 35%, preferably 7.5% (based on the total mass of the non-porous microcapsules excluding the water content).

In one embodiment, the payload is a flavor and/or aroma (active) dissolved/diluted/mixed with at least one oil, preferably a triglyceride such as caprylic capric triglyceride. The payload is preferably menthol active and caprylic capric triglyceride, and preferably at a weight ratio of 5-50%/95-50%, preferably 15%/85%. The pre-condensed silica precursors are preferably pre-condensed C18-TES and TEOS, and preferably at a molar ratio of 5-20%/95-80%, preferably 10/90%. The payload is combined with pre-condensed silica precursor at a weight ratio from 25% to 70%, preferably 50%. The weight percent of the active in the final non-porous microcapsules is from 1.25% to 35%, preferably 7.5% (based on the total mass of the non-porous microcapsules excluding the water content).

Porous Microcapsules Including Porous Core-Shell Spheroidal Sub-Micron/Microcapsules in Spheroidal Microcapsules (Type C) and Porous Core-Shell Spheroidal Sub-Micron/Microcapsules (Type D)

In one embodiment, the payload loaded in porous microcapsules is vitamin A in the form of all-trans-retinol (active) dissolved in different oils preferably a triglyceride such as caprylic capric triglyceride, and stabilised by non-toxic antioxidants, such as tocopherol. The payload is preferably all-trans-retinol and tocopherol and caprylic capric triglyceride at a weight ratio of 5-30%/10-40%/85-30%, preferably 10-20%/20-40%/70-40%. The pre-condensed silica precursors are preferably pre-condensed Vy-TES and TEOS, and preferably at a molar ratio of 5-20%/95-80%, preferably 10%/90%. The payload is then combined with pre-condensed silica precursors at a weight ratio from 25% to 80%, preferably from 40% to 70%. The weight percent of active in the final porous microcapsules is from 1.25% to 24%, preferably 2.5-14% (based on the total mass of the non-porous microcapsules excluding the water content).

In one embodiment, the payload loaded in porous microcapsules is vitamin A in the form of all-trans-retinol (active) dissolved in different oils preferably a mineral oil, and stabilised by non-toxic antioxidants, such as tocopherol. The payload is preferably all-trans-retinol and tocopherol and mineral oil at a weight ratio of 5-30%/10-40%/85-30%, preferably 10-20%/20-40%/70-40%. The pre-condensed silica precursors are preferably pre-condensed Vy-TES and TEOS, and preferably at a molar ratio of 5-20%/95-80%, preferably 10%/90%. The payload is then combined with pre-condensed silica precursors at a weight ratio from 25% to 80%, preferably 70%. The weight percent of active in the final porous microcapsules is from 3.5% to 21%, preferably from 7% to 14% (based on the total mass of the porous microcapsules excluding the water content).

In one embodiment, the payload loaded in non-porous microcapsules is vitamin A in the form of all-trans-retinol (active) dissolved in different oils preferably a triglyceride such as caprylic capric triglyceride, and stabilised by non-toxic antioxidants, such as coenzyme Q10. The payload is preferably all-trans-retinol and coenzyme Q10 and caprylic capric triglyceride at a weight ratio of 0-50%/1-20%/99-30%, preferably 10-20%/2-4%/88-76%. The pre-condensed silica precursors are preferably pre-condensed C1-TES and TEOS, and preferably at a molar ratio of 5-20%/95-80%, preferably 10%/90%. The payload is then combined with pre-condensed silica precursors at a weight ratio from 25% to 80%, preferably from 40% to 70%. The weight percent of active in the final porous microcapsules is from 0% to 40%, preferably from 4% to 14% (based on the total mass of the porous microcapsules excluding the water content).

In one embodiment, the payload loaded in porous microcapsules is vitamin A in the form of all-trans-retinol (active) dissolved in different oils preferably a triglyceride such as caprylic capric triglyceride, and stabilised by non-toxic antioxidants, such as hesperetin. The payload is preferably all-trans-retinol and hesperetin and caprylic capric triglyceride at a weight ratio of 0-50%/1-20%/99-30%, preferably 10-20%/2-4%/88-76%. The pre-condensed silica precursors are preferably pre-condensed C1-TES and TEOS, and preferably at a molar ratio of 5-20%/95-80%, preferably 10%/90%. The payload is then combined with pre-condensed silica precursors at a weight ratio from 25% to 80%, preferably from 40% to 70%. The weight percent of active in the final porous microcapsules is from 0% to 40%, preferably from 4% to 14% (based on the total mass of the porous microcapsules excluding the water content).

In one embodiment, the payload loaded in porous microcapsules is cannabinoid in the form of cannabidiol (active) dissolved in different oils preferably a coconut oil. The payload is preferably cannabidiol and coconut oil at a weight ratio of 5-90%/95-10%, preferably 25%-75%/75%-25%. The pre-condensed silica precursors are preferably pre-condensed C10-TES and C8-TES and TEOS, and preferably at a molar ratio of 10.0-22.5%/5.0-7.5%/85-70% preferably 22.5%/7.5%/70%. The payload is then combined with pre-condensed silica precursors at a weight ratio from 25% to 80%, preferably from 40% to 70%. The weight percent of active in the final non-porous microcapsules is from 1.2% to 75%, preferably from 10% to 50% (based on the total mass of the non-porous microcapsules excluding the water content).

In one embodiment, the payload loaded in porous microcapsules is cannabinoid in the form of Tetrahydrocannabinol (active) dissolved in different oils preferably a coconut oil. The payload is preferably cannabidiol and coconut oil at a weight ratio of 5-100%/95-0%, preferably 25%-75%/75%-25%. The pre-condensed silica precursors are preferably pre-condensed C10-TES and C8-TES and TEOS, and preferably at a molar ratio of 10.0-22.5%/5.0-7.5%/85-70% preferably 22.5%/7.5%/70%. The payload is then combined with pre-condensed silica precursors at a weight ratio from 25% to 80%, preferably from 40% to 70%. The weight percent of active in the final non-porous microcapsules is from 1.2% to 80%, preferably from 10% to 50% (based on the total mass of the non-porous microcapsules excluding the water content).

In one embodiment, the payload loaded in porous microcapsules is vitamin A in the form of all-trans-retinol (active), mixed with cannabinoid in the form of cannabidiol (active) dissolved in different oils preferably a mineral oil, and stabilised by non-toxic antioxidants, such as tocopherol. The payload is preferably all-trans-retinol, cannabidiol, tocopherol and mineral oil at a weight ratio of 5-30%/0-15%/45-

25%/50-30%, preferably 10-20%/10%/40-20%/40-50%. The pre-condensed silica precursors are preferably pre-condensed C10-TES and C8-TES and TEOS, and preferably at a molar ratio of 10.0-22.5%/5.0-7.5%/85-70% preferably 22.5%/7.5%/70%. The payload is then combined with pre-condensed silica precursors at a weight ratio from 25% to 80%, preferably from 40% to 70%. The weight percent of all-trans-retinol in the final non-porous microcapsules is from 1.25% to 24%, preferably from 2.5% to 14% (based on the total mass of the non-porous microcapsules excluding the water content). The weight percent of cannabidiol in the final non-porous microcapsules is from 6.25% to 36%, preferably from 2.5% to 14% (based on the total mass of the non-porous microcapsules excluding the water content).

In one embodiment, the payload loaded in porous microcapsules is vitamin A in the form of all-trans-retinol (active) dissolved in different oils preferably a triglyceride such as caprylic capric triglyceride and stabilised by non-toxic antioxidants, such as tocopherol. The payload is preferably all-trans-retinol and tocopherol and caprylic capric triglyceride at a weight ratio of 5-30%/10-40%/85-30%, preferably 10-20%/20-40%/70-40%. The pre-condensed silica precursors are preferably pre-condensed C10-TES and C8-TES and TEOS, and preferably at a molar ratio of 10.0-22.5%/5.0-7.5%/85-70% preferably 22.5%/7.5%/70%. The payload is then combined with pre-condensed silica precursors at a weight ratio from 25% to 80%, preferably from 40% to 70%. The weight percent of active in the final porous microcapsules is from 1.25% to 24%, preferably 2.5-14% (based on the total mass of the non-porous microcapsules excluding the water content).

In one embodiment, the payload loaded in porous microcapsules is essential oil and/or perfume and/or fragrance (active) used in its pure form. The payload is preferably the black spruce. The pre-condensed silica precursors are preferably pre-condensed C10-TES and C8-TES and TEOS, and preferably at a molar ratio of 10.0-22.5%/5.0-7.5%/85-70% preferably 22.5%/7.5%/70%. In the final non-porous microcapsules obtained, the weight percent of the active is from 1% to 95%, preferably from 20% to 70% (based on the total mass of the microcapsules excluding the water content).

Porous Microspheres Including Porous Spheroidal Sub-Micron/Microspheres (Type E)

In one embodiment, the payload loaded in porous microspheres is vitamin A in the form of all-trans-retinol (active) dissolved in different oils preferably a triglyceride such as caprylic capric triglyceride, and stabilised by non-toxic antioxidants, such as tocopherol. The payload is preferably all-trans-retinol and tocopherol and caprylic capric triglyceride at a weight ratio of 5-30%/10-40%/85-30%, preferably 10-20%/20-40%/70-40%. The pre-condensed silica precursors are preferably pre-condensed C8-TES and TEOS, and preferably at a molar ratio of 5-60%/95-40%, preferably 10%/90%. The payload is then combined with pre-condensed silica precursors at a weight ratio from 25% to 80%, preferably from 40% to 70%. The weight percent of active in the final porous microspheres is from 1.25% to 24%, preferably 2.5-14% (based on the total mass of the porous microspheres excluding the water content).

In one embodiment, the payload loaded in porous microspheres is vitamin A in the form of all-trans-retinol (active) dissolved in different oils preferably a triglyceride such as caprylic capric triglyceride, and stabilised by non-toxic antioxidants, such as tocopherol. The payload is preferably all-trans-retinol and tocopherol and caprylic capric triglyceride at a weight ratio of 5-30%/10-40%/85-30%, preferably 10-20%/20-40%/70-40%. The pre-condensed silica precursors are preferably pre-condensed C1-TES and C18-TES and TEOS, and preferably at a molar ratio of 10.0-20%/2.5-5.0%/87.5-75%, preferably 10%/2.5%/87.5%. The payload is then combined with pre-condensed silica precursors at a weight ratio from 25% to 80%, preferably from 40% to 70%. The weight percent of active in the final porous microspheres is from 1.25% to 24%, preferably 2.5-14% (based on the total mass of the porous microspheres excluding the water content).

In one embodiment, the payload loaded in porous microspheres is vitamin A in the form of all-trans-retinol (active) dissolved in different oils preferably a triglyceride such as caprylic capric triglyceride, and stabilised by non-toxic antioxidants, such as tocopherol and ascorbyl palmitate. The payload is preferably all-trans-retinol and tocopherol and ascorbyl palmitate and caprylic capric triglyceride at a weight ratio of 5-30%/10-40%/2-10%/85-20%, preferably 10-20%/20-40%/2-4%/68-36%, and more preferably 10%/20%/2%/68%. The pre-condensed silica precursors are preferably pre-condensed C1-TES and C18-TES and TEOS, and preferably at a molar ratio of 10.0-20%/2.5-5.0%/87.5-75%, preferably 10%/2.5%/87.5%. The payload is then combined with pre-condensed silica precursors at a weight ratio from 25% to 80%, preferably from 40% to 70%. The weight percent of active in the final porous microspheres is from 1.25% to 24%, preferably 2.5-14%, and more preferably 5% (based on the total mass of the porous microspheres excluding the water content).

In one embodiment, the payload loaded in porous microspheres is vitamin A in the form of all-trans-retinol (active) dissolved in different oils preferably a triglyceride such as caprylic capric triglyceride, and stabilised by non-toxic antioxidants, such as tocopherol and hesperetin. The payload is preferably all-trans-retinol and tocopherol and hesperetin and caprylic capric triglyceride at a weight ratio of 5-30%/10-40%/2-10%/85-20%, preferably 10-20%/20-40%/2-4%/68-36%. The pre-condensed silica precursors are preferably pre-condensed C1-TES and C18-TES and TEOS, and preferably at a molar ratio of 10.0-20%/2.5-5.0%/87.5-75%, preferably 10%/2.5%/87.5%. The payload is then combined with pre-condensed silica precursors at a weight ratio from 25% to 80%, preferably from 40% to 70%. The weight percent of active in the final porous microspheres is from 1.25% to 24%, preferably 2.5-14% (based on the total mass of the porous microspheres excluding the water content).

In one embodiment, the payload loaded in porous microspheres is vitamin A in the form of all-trans-retinol (active) dissolved in different oils preferably a triglyceride such as caprylic capric triglyceride, and stabilised by non-toxic antioxidants, such as tocopherol. The payload is preferably all-trans-retinol and coenzyme Q10 and caprylic capric triglyceride at a weight ratio of 5-30%/2-10%/93-60%, preferably 10-20%/2-4%/88-76%. The pre-condensed silica precursors are preferably pre-condensed C1-TES and C18-TES and TEOS, and preferably at a molar ratio of 10.0-20.0%/2.5-5.0%/87.5-75.0%, preferably 10.0%/2.5%/87.5%. The payload is then combined with pre-condensed silica precursors at a weight ratio from 25% to 80%, preferably from 40% to 70%. The weight percent of active in the final porous microspheres is from 1.25% to 24%, preferably 2.5-14% (based on the total mass of the porous microspheres excluding the water content).

In one embodiment, the payload loaded in porous microspheres is vitamin A in the form of all-trans-retinol (active) dissolved in different oils preferably a triglyceride such as caprylic capric triglyceride, and stabilised by non-toxic antioxidants, such as tocopherol. The payload is preferably all-trans-retinol and tocopherol and caprylic capric triglyceride at a weight ratio of 5-30%/10-40%/85-30%, preferably 10-20%/20-40%/70-40%. The pre-condensed silica precursors are preferably pre-condensed C1-TES and C18-TES and TEOS, and preferably at a molar ratio of 10.0-20%/2.5-5.0%/87.5-75%, preferably 10%/5%/85%. The payload is then combined with pre-condensed silica precursors at a weight ratio from 25% to 80%, preferably from 40% to 70%. The weight percent of active in the final porous microspheres is from 1.25% to 24%, preferably 2.5-14% (based on the total mass of the porous microspheres excluding the water content).

In one embodiment, the payload loaded in porous microspheres is cannabinoid in the form of cannabidiol (active) dissolved in different oils preferably a coconut oil. The payload is preferably cannabidiol and coconut oil at a weight ratio of 5-90%/95-10%, preferably 25%-75%/75%-25%. The pre-condensed silica precursors are preferably pre-condensed C1-TES and C18-TES and TEOS, and preferably at a molar ratio of 10.0-20%/2.5-5.0%/87.5-75%, preferably 10%/5%/85%. The payload is then combined with pre-condensed silica precursors at a weight ratio from 25% to 80%, preferably from 40% to 70%. The weight percent of active in the final porous microspheres is from 1.2% to 75%, preferably from 10% to 50% (based on the total mass of the porous microspheres excluding the water content).

In one embodiment, the payload loaded in porous microspheres is cannabinoid in the form of Tetrahydrocannabinol (active) dissolved in different oils preferably a coconut oil. The payload is preferably cannabidiol and coconut oil at a weight ratio of 5-100%/95-0%, preferably 25%-75%/75%-25%. The pre-condensed silica precursors are preferably pre-condensed C1-TES and C18-TES and TEOS, and preferably at a molar ratio of 10.0-20%/2.5-5.0%/87.5-75%, preferably 10%/5%/85%. The payload is then combined with pre-condensed silica precursors at a weight ratio from 25% to 80%, preferably from 40% to 70%. The weight percent of active in the final porous microspheres is from 1.2% to 80%, preferably from 10% to 50% (based on the total mass of the porous microspheres excluding the water content).

In one embodiment, the payload loaded in porous microspheres is vitamin A in the form of all-trans-retinol (active), mixed with cannabinoid in the form of cannabidiol (active) dissolved in different oils preferably a mineral oil, and stabilised by non-toxic antioxidants, such as tocopherol. The payload is preferably all-trans-retinol, cannabidiol, tocopherol and mineral oil at a weight ratio of 5-30%/0-15%/45-25%/50-30%, preferably 10-20%/10%/40-20%/40-50%. The pre-condensed silica precursors are preferably pre-condensed C1-TES and C18-TES and TEOS, and preferably at a molar ratio of 10.0-20%/2.5-5.0%/87.5-75%, preferably 10%/5%/85%. The payload is then combined with pre-condensed silica precursors at a weight ratio from 25% to 80%, preferably from 40% to 70%. The weight percent of all-trans-retinol in the final porous microspheres is from 1.25% to 24%, preferably from 2.5% to 14% (based on the total mass of the non-porous microcapsules excluding the water content). The weight percent of cannabidiol in the final porous microspheres is from 6.25% to 36%, preferably from 2.5% to 14% (based on the total mass of the porous microspheres excluding the water content).

In one embodiment, the payload loaded in porous microspheres is essential oil and/or perfume and/or fragrance (active) used in its pure form. The payload is preferably the black spruce essential oil. The pre-condensed silica precursors are preferably pre-condensed C1-TES and TEOS, and preferably at a molar ratio of 10-50%/90-50% preferably 30%/70%. In the final porous microspheres obtained, the weight percent of the active is from 1% to 95%, preferably from 20% to 70% (based on the total mass of the microspheres excluding the water content).

In one embodiment, the payload loaded in porous microspheres is essential oil and/or perfume and/or fragrance (active) used in its pure form. The payload is preferably the black spruce essential oil. The pre-condensed silica precursors are preferably pre-condensed C1-TES and TEOS, and preferably at a molar ratio of 10-50%/90-50% preferably 50%/50%. In the final porous microspheres obtained, the weight percent of the active is from 1% to 95%, preferably from 20% to 70% (based on the total mass of the microspheres excluding the water content).

In one embodiment, the payload loaded in porous microspheres is essential oil and/or perfume and/or fragrance (active) used in its pure form. The payload is preferably the pure gray pine essential oil. The pre-condensed silica precursors are preferably pre-condensed C10-TES and C8-TES and TEOS, and preferably at a molar ratio of 10.0-22.5%/5.0-7.5%/85-70% preferably 22.5%/7.5%/70%. The payload is then combined with pre-condensed silica precursors at a weight ratio from 25% to 80%, preferably from 40% to 70%. In the final porous microspheres obtained, the weight percent of the active is from 1% to 95%, preferably from 20% to 70% (based on the total mass of the microspheres excluding the water content)

In one embodiment, the payload loaded in porous microspheres is essential oil and/or perfume and/or fragrance (active) used in its pure form. The payload is preferably the pure black spruce essential oil. The pre-condensed silica precursors are preferably pre-condensed C10-TES and C8-TES and TEOS, and preferably at a molar ratio of 10.0-22.5%/5.0-7.5%/85-70% preferably 22.5%/7.5%/70%. The payload is then combined with pre-condensed silica precursors at a weight ratio from 25% to 80%, preferably from 40% to 70%. In the final porous microspheres obtained, the weight percent of the active is from 1% to 95%, preferably from 20% to 70% (based on the total mass of the microspheres excluding the water content).

In one embodiment, the payload loaded in porous microspheres is flavor and/or aroma (active) used in its pure form. The payload is preferably the menthol. The pre-condensed silica precursors are preferably pre-condensed C1-TES and TEOS, and preferably at a molar ratio of 10-50%/90-50%, preferably 30%/70%. In the final porous microspheres obtained, the weight percent of the active is from 1% to 95%, preferably from 20% to 70% (based on the total mass of the microspheres excluding the water content).

Example of Spheroidal Particles

General Procedure: Preparation of spheroidal silica particles with fully hydrolyzed and pre-condensed C1-TES and partially hydrolysed and pre-condensed TEOS with presence of payloads and without surfactants.

Spheroidal silica particles with C1-TES/TEOS molar ratio 10%/90%. Typically, 44.061 g (211.5 mmol) of TEOS was partially pre-hydrolyzed (1.1 $H_2O$ molar eq) in acidic conditions of 4.19 g of 0.01 N HCl and 19.29 g EtOH (HPLC grade) for 1 hour under stirring. Meanwhile, the fully pre-hydrolyzation of 4.19 g of C1-TES (3.3 $H_2O$ molar eq) was carried out in another vial in acidic conditions of 1.41 g of 0.01 N HCl under stirring for 1 hour. The fully pre-hydrolyzed C1-TES silica precursor was then added to the partially pre-hydrolyzed TEOS leading to the formation of fully/partially hydrolysed 10%/90% C1-TES/TEOS silica precursors. The mixture obtained was distilled at 100° C.

under an inert gas until complete solvents removal. This obtained pre-polymer was cooled to room temperature. Then, 15 g of payload (50 wt % payloads loading) was added to the pre-polymer prepared as described. The resulted dispersed oil phase was added to 328 g of water as continuous phase, under mixing using a high-shear mixer at 3200 rpm. The mixture was stirred for 5 min to generate a homogeneous emulsion. Then, 11.5 g of concentrated $NH_4OH$ was added as condensation catalyst. After 45 seconds the high-shear mixer was stopped, and the suspension was kept under gentle agitation for at least overnight under inert conditions and protected from light. After that, the suspension spheroidal particles was filtered and washed with 1.5-2.0 L ascorbic acid solution (1.0 mg/mL) until neutral pH. The spheroidal particles obtained were dried at room temperature for h, transferred in a dark glasses bottle, and stored under argon at 5° C.

Examples of Core-Shell Sub-Micron/Microcapsules in Microcapsules

EXAMPLE 1: Core-shell sub-micron/microcapsules in microcapsules with different molar ratio of C1-TES and TEOS and with the presence of 50 wt % payload (all-trans-retinol mixture oils) loading (15 g mixture containing 1.50 g of all-trans-retinol, 3.0 g of tocopherols mixture and 10.5 g of caprylic capric oil triglyceride, respectively 10, 20, and 70 wt % composition).

EXAMPLE 1-1: Core-shell sub-micron/microcapsules in microcapsules containing 5% C1-TES and 95% TEOS were prepared using the general procedure. The main characteristics of the obtained core-shell sub-micron/microcapsules in microcapsules are summarised in FIG. 1 and Table 1.

EXAMPLE 1-2: Core-shell sub-micron/microcapsules in microcapsules containing 10% C1-TES and 90% TEOS were prepared using the general procedure. The main characteristics of the obtained core-shell sub-micron/microcapsules in microcapsules are summarised in FIG. 1 and Table 1.

EXAMPLE 1-3: Core-shell sub-micron/microcapsules in microcapsules containing 15% C1-TES and 85% TEOS were prepared using the general procedure. The main characteristics of the obtained core-shell sub-micron/microcapsules in microcapsules are summarised in FIG. 1 and Table 1.

EXAMPLE 1-4: Core-shell sub-micron/microcapsules in microcapsules containing 20% C1-TES and 80% TEOS were prepared using the general procedure. The main characteristics of the obtained core-shell sub-micron/microcapsules in microcapsules are summarised in FIG. 1 and Table 1.

Thus, obtained core-shell sub-micron/microcapsules in microcapsules contain around 5 wt % of retinol active based on the total mass of the product excluding the water content.

TABLE 1

Size and porosity data of examples of core-shell sub-micron/microcapsules in microcapsules with different molar ratio of C1-TES and TEOS:

| Examples | Yield retinol (%) | Particle size | | $N_2$ isotherm analysis | |
|---|---|---|---|---|---|
| | | d50 (μm) | d90/d10 | Surface area ($m^2 \cdot g^{-1}$) | Pore volume ($cm^3 \cdot g^{-1}$) |
| Example 1-1 | 70 | 11.0 | 3.3 | 11.0 | 0.0 |
| Example 1-2 | 98 | 14.0 | 3.0 | 0.0 | 0.0 |
| Example 1-3 | 99 | 12.0 | 2.9 | 2.0 | 0.0 |
| Example 1-4 | 100 | 10.0 | 4.0 | 0.0 | 0.0 |

EXAMPLE 2: Core-shell sub-micron/microcapsules in microcapsules with 10% C1-TES and 90% TEOS and with the presence of 50 wt % payload (all-trans-retinol mixture oils) loading. The pre-hydrolysed silica precursor was distilled at 85° C. under inert conditions until complete solvents removal.

Figure 2:
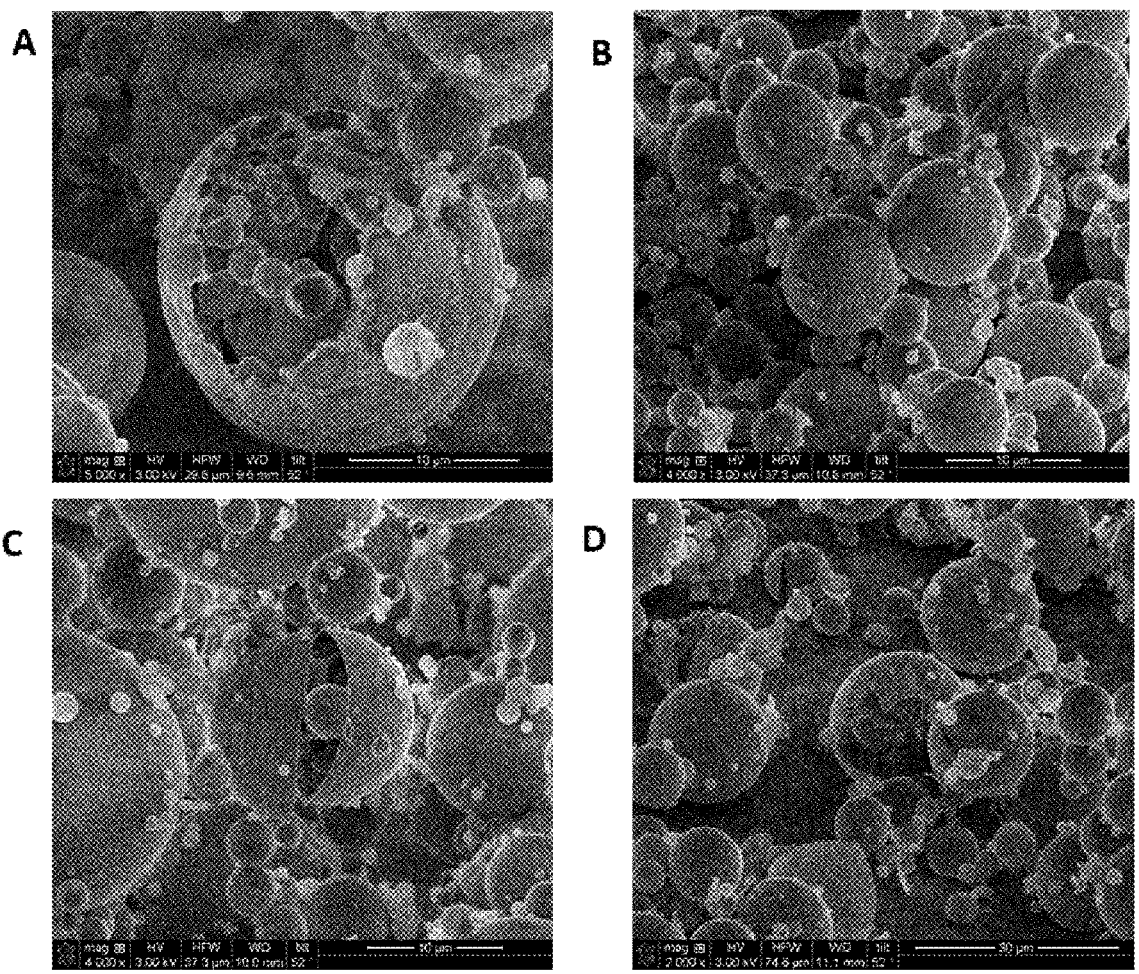
FIG. 2. A) Example 2: SEM image of core-shell sub-micron/microcapsules in microcapsules, the pre-hydrolysed silica precursor was distilled at 85° C. (scale bar=10 μm). B-D) Examples 3-1, 3-2, and 3-3: SEM images of core-shell sub-micron/microcapsules in microcapsules containing different payload loadings B) Example 3-1 (scale bar=10 μm), C) Example 3-2 (scale bar=10 μm), and C) Example 3-3 (scale bar=30 μm).

Core-shell sub-micron/microcapsules in microcapsules containing 10% C1-TES and 90% TEOS and 50 wt % payload loading (15 g mixture containing 1.50 g of all-trans-retinol, 3.0 g of tocopherols mixture and 10.5 g of caprylic capric oil triglyceride, respectively 10, 20, and 70 wt % composition) were prepared using the general procedure, except the pre-hydrolysed silica precursor distillation step that was realised at 85° C. The main characteristics of the obtained core-shell sub-micron/microcapsules in microcapsules are summarised in FIG. 2 and Table 2.

EXAMPLE 3: Core-shell sub-micron/microcapsules in microcapsules with 10% C1-TES and 90% TEOS and with different wt % payload (all-trans-retinol mixture oils) loading.

EXAMPLE 3-1: Core-shell sub-micron/microcapsules in microcapsules with 40 wt % payload loading (9 g mixture containing 0.9 g of all-trans-retinol, 1.8 g of tocopherols mixture and 6.3 g of caprylic capric oil triglyceride, respectively 10, 20, and 70 wt % composition) were prepared using the general procedure. The main characteristics of the obtained core-shell sub-micron/microcapsules in microcapsules are summarised in FIG. 2 and Table 2.

EXAMPLE 3-2: Non-porous Core-shell sub-micron/microcapsules in microcapsules with 50 wt % payload loading (15 g mixture containing 1.50 g of all-trans-retinol, 3.0 g of tocopherols mixture and 10.5 g of caprylic capric oil triglyceride, respectively 10, 20, and 70 wt % composition). See Example 1.2. The main characteristics of the obtained core-shell sub-micron/microcapsules in microcapsules are summarised in FIG. 2 and Table 2.

EXAMPLE 3-3: Core-shell sub-micron/microcapsules in microcapsules with 64 wt % payload loading (25 g mixture containing 2.50 g of all-trans-retinol, 5.0 g of tocopherols mixture and 17.5 g of caprylic capric oil triglyceride, respectively 10, 20, and 70 wt % composition) were prepared using the general procedure. The main characteristics of the obtained core-shell sub-micron/microcapsules in microcapsules are summarised in FIG. 2 and Table 2.

Thus, obtained core-shell sub-micron/microcapsules in microcapsules contain from 4 wt % to 7 wt % of retinol active based on the total mass of the product excluding the water content.

TABLE 2

Size and porosity data of examples of core-shell sub-micron/microcapsules in microcapsules where the pre-hydrolysed silica precursor was distilled at 85° C. (Example 2) and with different payload loading (Examples 3):

| Examples | Yield Retinol (%) | Particle size d50 (μm) | d90/d10 | N$_2$ isotherm analysis Surface area (m$^2 \cdot$g$^{-1}$) | Pore volume (cm$^3 \cdot$g$^{-1}$) | Average pore size (nm) |
|---|---|---|---|---|---|---|
| Example 2 | 70 | 15 | 2.8 | 487.0 | 0.33 | 2.7 |
| Example 3-1 | 93 | 9.0 | 2.6 | 208.0 | 0.10 | 3.2 |
| Example 3-2 | 98 | 14.0 | 3.0 | 0.0 | 0.00 | 0.0 |
| Example 3-3 | 94 | 18.0 | 2.5 | 141.0 | 0.12 | 3.5 |

EXAMPLE 4: Core-shell sub-micron/microcapsules in microcapsules with 10% C1-TES and 90% TEOS and with the presence of 50 wt % payload loading in different compositions (all-trans-retinol mixture oils).

Figure 3:
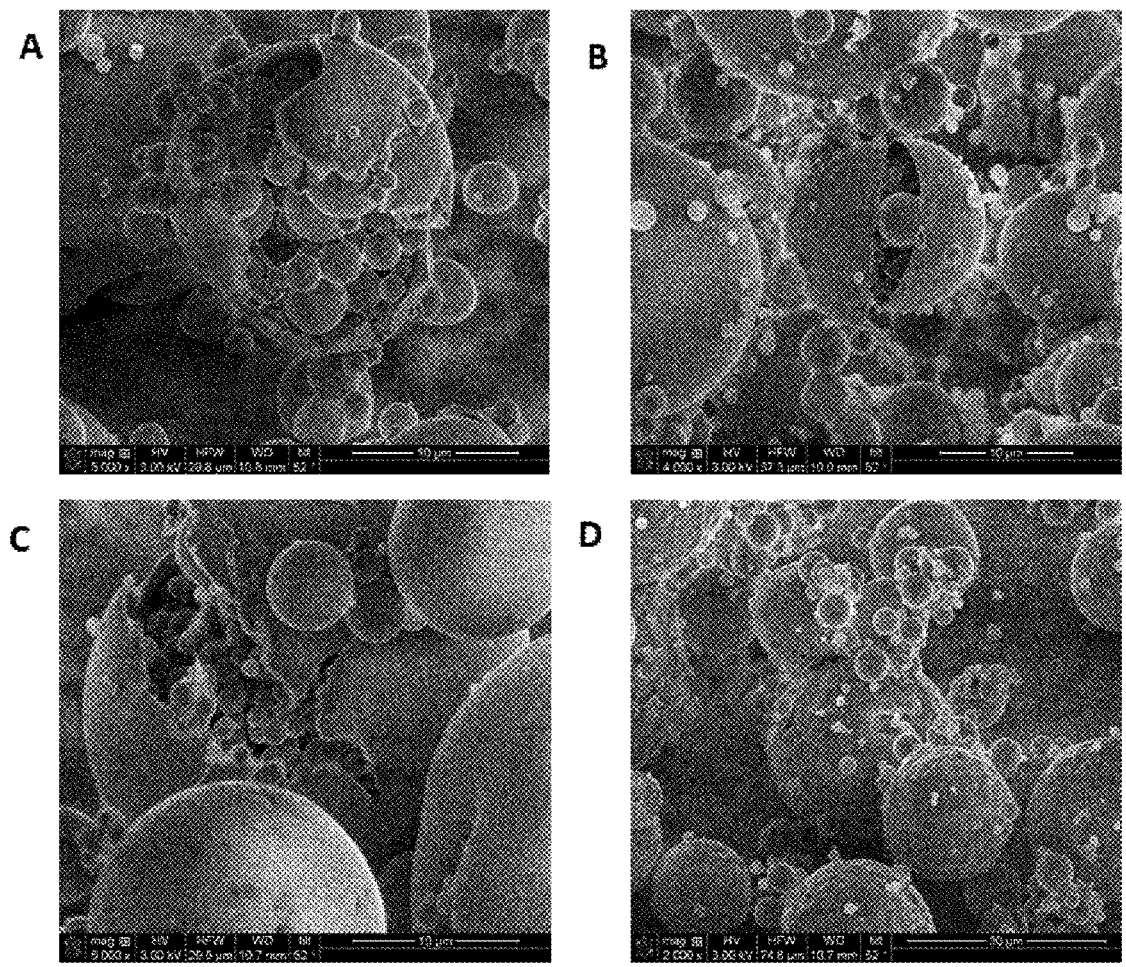
FIG. 3. SEM images of the examples of core-shell sub-micron/microcapsules in microcapsules with presence of payload in different compositions. A) Example 4-1 (scale bar=10 μm), B) Example 4-2 (scale bar=10 μm) and C) Example 4-3 (scale bar=10 μm). D) Example 4-4 (scale bar=30 μm).

EXAMPLE 4-1: Core-shell sub-micron/microcapsules in microcapsules with 50 wt % payload loading (9 g mixture containing 0.75 g of all-trans-retinol, 1.5 g of tocopherols mixture and 12.75 g of caprylic capric oil triglyceride, respectively 5, 10, and 85 wt % composition) were prepared using the general procedure. The main characteristics of the obtained core-shell sub-micron/microcapsules in microcapsules are summarised in FIG. 3 and Table 3.

EXAMPLE 4-2: Core-shell sub-micron/microcapsules in microcapsules with 50 wt % payload loading (15 g mixture containing 1.50 g of all-trans-retinol, 3.0 g of tocopherols mixture and 10.5 g of caprylic capric oil triglyceride, respectively 10, 20, and 70 wt % composition). See Example 1.2. The main characteristics of the obtained core-shell sub-micron/microcapsules in microcapsules are summarised in FIG. 3 and Table 3.

EXAMPLE 4-3: Core-shell sub-micron/microcapsules in microcapsules with 50 wt % payload loading (15 g mixture containing 2.25 g of all-trans-retinol, 4.50 g of tocopherols mixture and 8.25 g of caprylic capric oil triglyceride, respectively 15, 30, and 55 wt % composition) were prepared using the general procedure. The main characteristics of the obtained core-shell sub-micron/microcapsules in microcapsules are summarised in FIG. 3 and Table 3.

EXAMPLE 4-4: Core-shell sub-micron/microcapsules in microcapsules with 50 wt % payload loading (15 g mixture containing 3.00 g of all-trans-retinol, 6.00 g of tocopherols mixture and 6.00 g of caprylic capric oil triglyceride, respectively 20, 40, and 40 wt % composition) were prepared using the general procedure. The main characteristics of the obtained core-shell sub-micron/microcapsules in microcapsules are summarised in FIG. 3 and Table 3.

Thus, obtained core-shell sub-micron/microcapsules in microcapsules contain around 2.5 to around 10 wt % of retinol active based on the total mass of the product excluding the water content.

EXAMPLE 5: Core-shell sub-micron/microcapsules in microcapsules with 10% C1-TES and 90% TEOS and with the presence of 50 wt % payload loading (the all-trans-retinol active was dissolved in corn oil).

Figure 4:
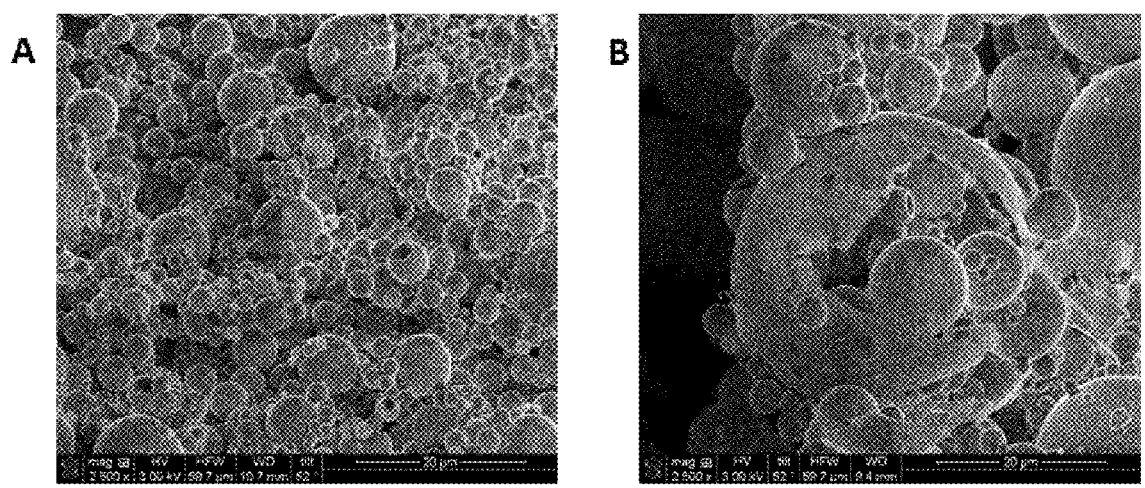
FIG. 4. SEM images of the examples of core-shell sub-micron/microcapsules in microcapsules with all-trans-retinol active dissolved in corn oil: A) Example 5-1 (scale bar=20 μm), B) Example 5-2 (scale bar=20 μm).

EXAMPLE 5-1: Core-shell sub-micron/microcapsules in microcapsules with 50 wt % payload loading (15 g mixture containing 2.25 g of all-trans-retinol and 12.75 g of corn oil, respectively 15 and 85 wt % composition) were prepared using the general procedure. The main characteristics of the obtained core-shell sub-micron/microcapsules in microcapsules are summarised in FIG. 4 and Table 4.

EXAMPLE 5-2: Core-shell sub-micron/microcapsules in microcapsules with 50 wt % payload (15 g mixture containing 1.50 g of all-trans-retinol, 3.0 g of tocopherols mixture and 10.5 g of corn oil, respectively 10, 20, and 70 wt % composition) were prepared using the general procedure. The main characteristics of the obtained core-shell sub-micron/microcapsules in microcapsules are summarised in FIG. 4 and Table 4.

Thus, obtained core-shell sub-micron/microcapsules in microcapsules contain around 7.5 wt % (Example 5-1) and around 5 wt % (Example 5-2) of retinol active based on the total mass of the product excluding the water content.

TABLE 4

Size and porosity data of examples of core-shell sub-micron/microcapsules in microcapsules with retinol active dissolved in corn oil:

| Examples | Yield Retinol (%) | Particle size d50 (μm) | d90/d10 | Porosity Surface area (m$^2 \cdot$g$^{-1}$) | Pore volume (cm$^3 \cdot$g$^{-1}$) |
|---|---|---|---|---|---|
| Example 5-1 | 80 | 19.0 | 3.8 | 0.0 | 0.00 |
| Example 5-2 | 75 | 17.0 | 7.4 | 0.0 | 0.00 |

EXAMPLE 6: Core-shell sub-micron/microcapsules in microcapsules with 10% of different monoalkyl-trialkoxysi-

TABLE 3

Size and porosity data of examples of core-shell sub-micron/microcapsules in microcapsules with presence of 50 wt % payload in different compositions:

| Examples | Yield Retinol (%) | Particle size d50 (μm) | d90/d10 | N$_2$ isotherm analysis Surface area (m$^2 \cdot$g$^{-1}$) | Pore volume (cm$^3 \cdot$g$^{-1}$) | Average pore size (nm) |
|---|---|---|---|---|---|---|
| Example 4-1 | 73 | 13.0 | 6.5 | 2.0 | 0.00 | 0.0 |
| Example 4-2 | 98 | 14.0 | 3.0 | 0.0 | 0.00 | 0.0 |
| Example 4-3 | 93 | 16.0 | 4.1 | 23.0 | 0.30 | 5.4 |
| Example 4-4 | 74 | 16.0 | 4.1 | 361.0 | 0.37 | 4.2 | lanes and 90% TEOS and with the presence of 50 wt % payload (all-trans-retinol mixture oils) loading (15 g mixture containing 1.50 g of all-trans-retinol, 3.0 g of tocopherols mixture and 10.5 g of caprylic capric oil, respectively 10, 20, and 70 wt % composition).

Figure 5:
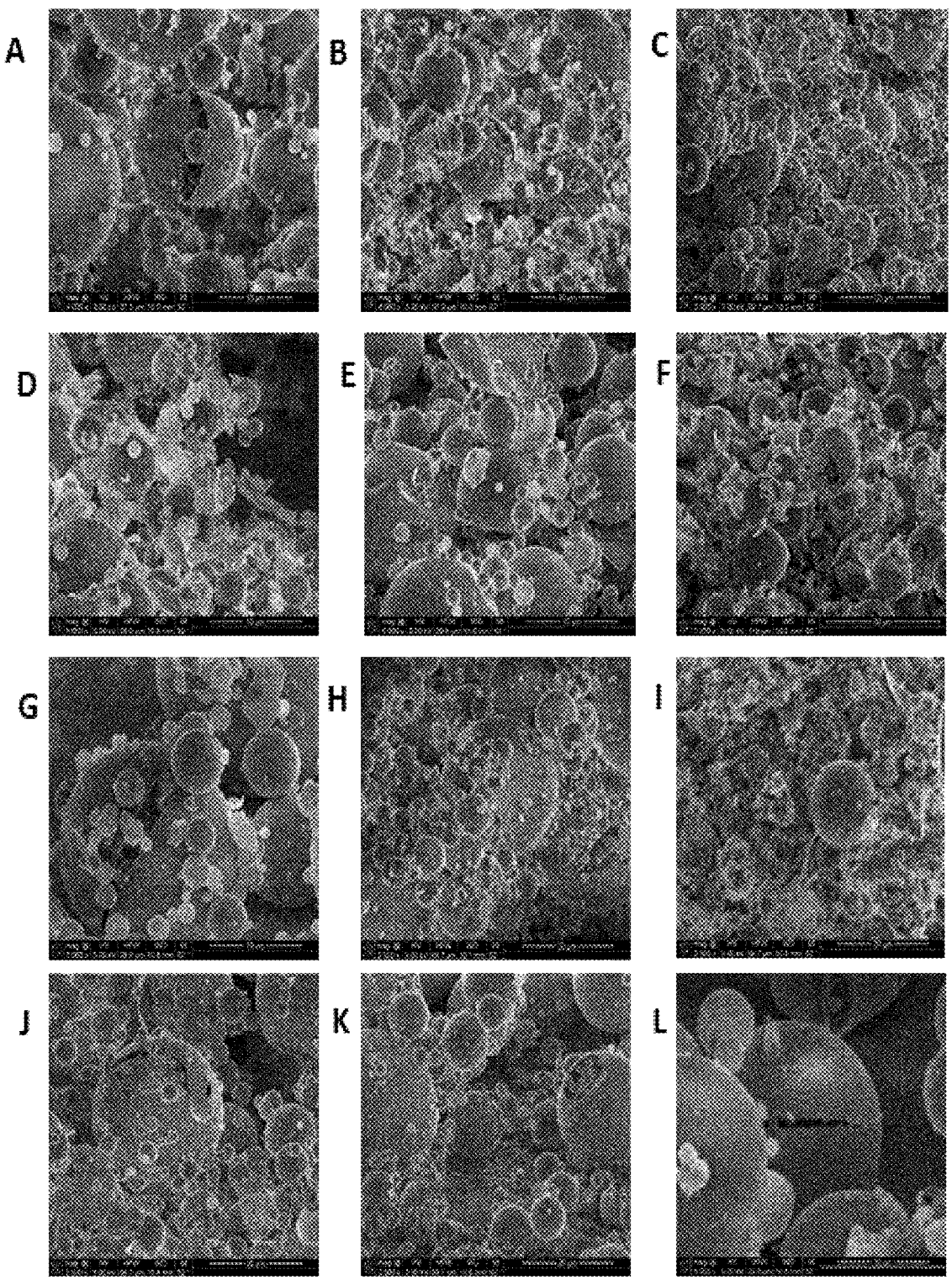
FIG. 5. SEM images of the examples of core-shell sub-micron/microcapsules in microcapsules obtained with different monoalkyl-trialkoxysilanes and TEOS. A) Example 6-1 (scale bar=10 μm), B) Example 6-2 (scale bar=10 μm), C) Example 6-3 (scale bar=20 μm) D) Example 6-4 (scale bar=10 μm). E) Example 6-5 (scale bar=10 μm), F) Example 6-6 (scale bar=10 μm), G) Example 6-7 (scale bar=50 μm), H) Example 6-8 (scale bar=10 μm), I) Example 6-9 (scale bar=20 μm). J) Example 7 (scale bar=20 μm). K) Example 8 (scale bar=20 μm). L) Example 9 (scale bar=10 μm).

EXAMPLE 6-1: Core-shell sub-micron/microcapsules in microcapsules containing 10% C1-TES and 90% TEOS. See Example 1-2. The main characteristics of the obtained core-shell sub-micron/microcapsules in microcapsules are summarised in FIG. 5 and Table 5.

EXAMPLE 6-2: Core-shell sub-micron/microcapsules in microcapsules containing 10% C2-DES and 90% TEOS were prepared using the general procedure. The main characteristics of the obtained core-shell sub-micron/microcapsules in microcapsules are summarised in FIG. 5 and Table 5.

EXAMPLE 6-3: Core-shell sub-micron/microcapsules in microcapsules containing 10% C18-TES fully hydrolysed (3.3 $H_2O$ molar eq) in acidic conditions with 0.05 N HCl and 90% TEOS partially hydrolysed (1.1 $H_2O$ molar eq) in acidic conditions with 0.01 N HCl were prepared using the general procedure. The main characteristics of the obtained core-shell sub-micron/microcapsules in microcapsules are summarised in FIG. 5 and Table 5.

EXAMPLE 6-4: Core-shell sub-micron/microcapsules in microcapsules containing 10% SH-TMS (3-mercaptopropyl trimethoxysilane) and 90% TEOS were prepared using the general procedure. The main characteristics of the obtained core-shell sub-micron/microcapsules in microcapsules are summarised in FIG. 5 and Table 5.

EXAMPLE 6-5: Core-shell sub-micron/microcapsules in microcapsules containing 10% Gp-TMS ((3-glycidyloxypropyl)trimethoxysilane) and 90% TEOS were prepared using the general procedure. The main characteristics of the obtained core-shell sub-micron/microcapsules in microcapsules are summarised in FIG. 5 and Table 5.

EXAMPLE 6-6: Core-shell sub-micron/microcapsules in microcapsules containing 10% PEG-TMS (2-[methoxy (polyethyleneoxy)6,9-propyl]trimethoxysilane) and 90% TEOS were prepared using the general procedure. The main characteristics of the obtained core-shell sub-micron/microcapsules in microcapsules are summarised in FIG. 5 and Table 5.

EXAMPLE 6-7: Core-shell sub-micron/microcapsules in microcapsules containing 10% Vy-TES (vynyltriethoxysilane) and 90% TEOS were prepared using the general procedure. The main characteristics of the obtained core-shell sub-micron/microcapsules in microcapsules are summarised in FIG. 5 and Table 5.

EXAMPLE 6-8: Core-shell sub-micron/microcapsules in microcapsules containing 10% Ph-TES (phenyltriethoxysilane) and 90% TEOS were prepared using the general procedure. The main characteristics of the obtained core-shell sub-micron/microcapsules in microcapsules are summarised in FIG. 5 and Table 5.

EXAMPLE 6-9: Core-shell sub-micron/microcapsules in microcapsules containing 10% TMAPS (3-(trimethoxysilyl) propyl-N,N,N-trimethylammonium chloride) fully hydrolysed (3.3 $H_2O$ molar eq) in acidic conditions with 0.05 N HCl and 90% TEOS partially hydrolysed (1.1 $H_2O$ molar eq) in acidic conditions with 0.01 N HCl and with the presence of 50 wt % payload loading (15 g mixture containing 1.50 g of all-trans-retinol, 0.3 g of hesperetin and 13.2 g of caprylic capric oil triglyceride, respectively 10, 2, and 88 wt % composition) were prepared using the general procedure. The main characteristics of the obtained core-shell sub-micron/microcapsules in microcapsules are summarised in FIG. 5 and Table 5.

EXAMPLE 7: Core-shell sub-micron/microcapsules in microcapsules with 10% dialkyl-dialkoxysilane and 90% TEOS in the presence of 50 wt % payload (all-trans-retinol mixture oils) loading.

Core-shell sub-micron/microcapsules in microcapsules containing 10% C2-DES (dimethydiethoxysilane) and 90% TEOS and 50 wt % payload loading (15 g mixture containing 1.50 g of all-trans-retinol, 3.0 g of tocopherols mixture and 10.5 g of caprylic capric oil triglyceride, respectively 10, 20, and 70 wt % composition) were prepared using the general procedure. The main characteristics of the obtained core-shell sub-micron/microcapsules in microcapsules are summarised in FIG. 5 and Table 5.

EXAMPLE 8: Core-shell sub-micron/microcapsules in microcapsules with 10% trialkyl-alkoxysilane and 90% TEOS and with the presence of 50 wt % payload (all-trans-retinol mixture oil) loading.

Core-shell sub-micron/microcapsules in microcapsules containing 10% C3-MS (trimethylmethoxysilane) and 90% TEOS and 50 wt % payload loading (15 g mixture containing 1.50 g of all-trans-retinol, 3.0 g of tocopherols mixture and 10.5 g of caprylic capric oil triglyceride, respectively 10, 20, and 70 wt % composition) were prepared using the general procedure. The main characteristics of the obtained core-shell sub-micron/microcapsules in microcapsules are summarised in FIG. 5 and Table 5.

EXAMPLE 9: Core-shell sub-micron/microcapsules in microcapsules with 5% BTEE (1,2-bis(triethoxysilyl)ethane) and 95% TEOS and with the presence of 50 wt % payload (all-trans-retinol mixture oils) loading.

Core-shell sub-micron/microcapsules in microcapsules containing 5% BTEE (bistriethoxysilylethane) trialkylalkoxysilane) fully hydrolysed (3.3 $H_2O$ molar eq) in acidic conditions with 0.019 N HCl and 95% TEOS partially hydrolysed (1.1 $H_2O$ molar eq) with HCl 0.01 N and 50 wt % payload loading (15 g mixture containing 1.50 g of all-trans-retinol, 3.0 g of tocopherols mixture and 10.5 g of caprylic capric oil, respectively 10, 20, and 70 wt % composition) were prepared using the general procedure. The main characteristics of the obtained core-shell sub-micron/microcapsules in microcapsules are summarised in FIG. 5 and Table 5.

TABLE 5

Size and porosity data of examples of core-shell sub-micron/microcapsules in microcapsules obtained with different monoalkyl-trialkoxysilanes and TEOS.

| | Particle size | | Porosity | | |
|---|---|---|---|---|---|
| Examples | d50 (μm) | d90/d10 | Surface area ($m^2 \cdot g^{-1}$) | Pore volume ($cm^3 \cdot g^{-1}$) | Average pore size (nm) |
| Example 6-1 | 14 | 3.0 | 0.0 | 0.0 | — |
| Example 6-2 | 14 | 2.9 | 6.0 | 0.0 | — |
| Example 6-3 | 16 | 14.9 | 4.0 | 0.0 | — |
| Example 6-4 | 10 | 4.5 | 371 | 0.27 | 2.9 |
| Example 6-5 | 7 | 8.5 | 385 | 0.55 | 5.8 |
| Example 6-6 | 14 | 2.9 | 198 | 0.17 | 3.3 |
| Example 6-7 | 13 | 3.1 | 288 | 0.22 | 3.0 |
| Example 6-8 | 13 | 5.5 | 331 | 0.20 | 2.5 |

TABLE 5-continued

Size and porosity data of examples of core-shell sub-micron/microcapsules in microcapsules obtained with different monoalkyl-trialkoxysilanes and TEOS.

| Examples | Particle size | | Porosity | | |
|---|---|---|---|---|---|
| | d50 (μm) | d90/d10 | Surface area ($m^2 \cdot g^{-1}$) | Pore volume ($cm^3 \cdot g^{-1}$) | Average pore size (nm) |
| Example 6-9 | 12 | 9.5 | 200 | 0.58 | 9.4 |
| Example 7 | 10 | 6.9 | 93 | 0.1 | 3.4 |
| Example 8 | 11 | 6.1 | 340 | 0.26 | 3.1 |
| Example 9 | 15 | 6.5 | 276 | 0.28 | 6.3 |

EXAMPLE 10: Core-shell sub-micron/microcapsules in microcapsules with different molar ratio of C1-TES and C8-TES and TEOS and with the presence of 50 wt % payload (all-trans-retinol mixture oils) loading: 15 g mixture containing 1.50 g of all-trans-retinol, 3.0 g of tocopherols mixture and 10.5 g of caprylic capric oil, respectively 10, 20, and 70 wt % composition.

Figure 6:
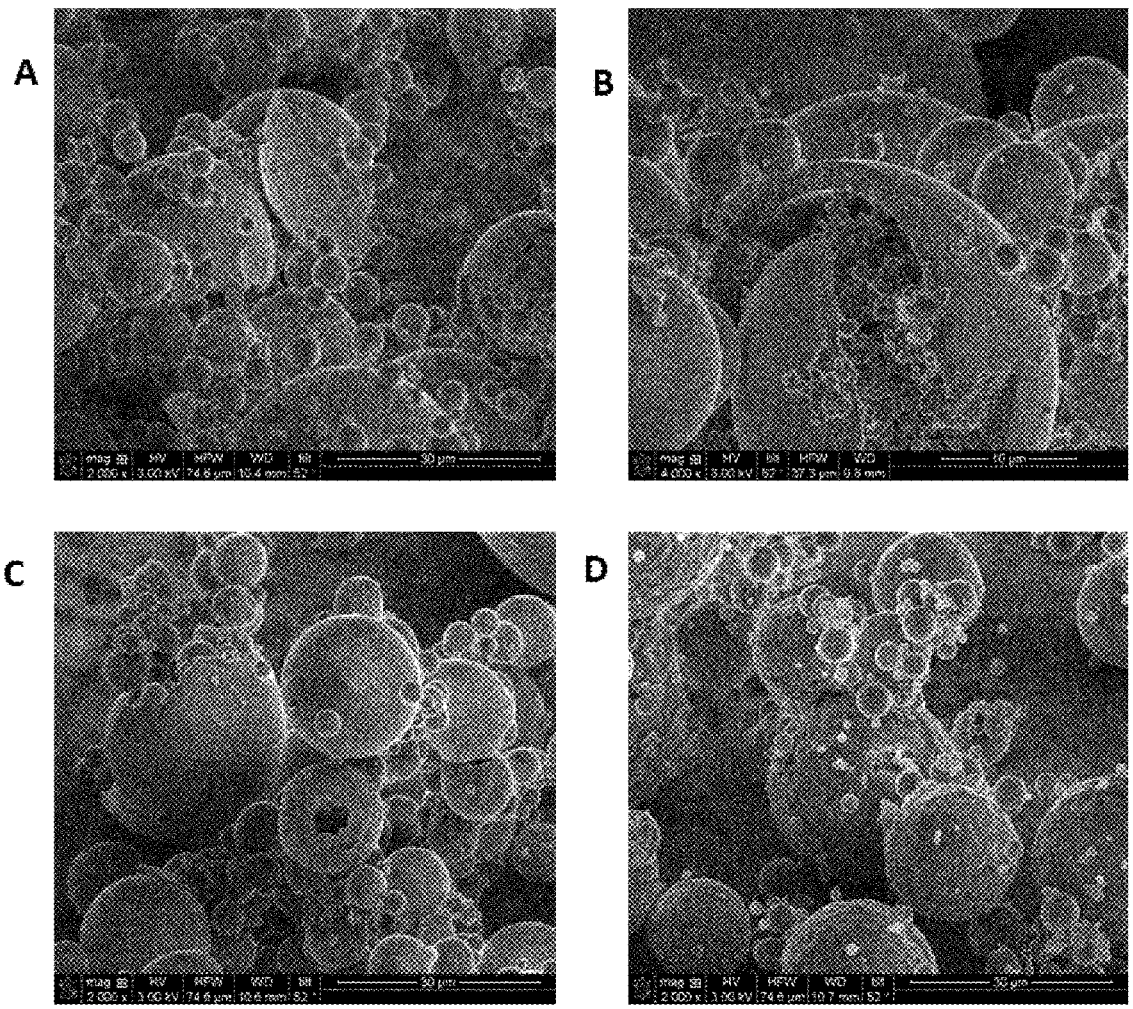
FIG. 6. SEM images of the examples of core-shell sub-micron/microcapsules in microcapsules with different silica precursors compositions and with presence of 50 wt % loading of all-trans-retinol mixture. A) Example 10-1 (scale bar=10 μm), B) Example 10-2 (scale bar=30 μm) and C) Example 10-3 (scale bar=30 μm). D) Example 10-4 (scale bar=100 μm).

EXAMPLE 10-1: Core-shell sub-micron/microcapsules in microcapsules containing 10% C1-TES fully hydrolysed (3.3 H$_2$O molar eq) with 0.01 N HCl, 5% C8-TES fully hydrolysed (3.3 H$_2$O molar eq) with 0.05 N HCl and 85% TEOS partially hydrolysed (1.1 H$_2$O molar eq) with HCl 0.01 N were prepared using the general procedure. The main characteristics of the obtained core-shell sub-micron/microcapsules in microcapsules are summarised in FIG. 6 and Table 6.

EXAMPLE 10-2: Core-shell sub-micron/microcapsules in microcapsules containing 15% C1-TES fully hydrolysed (3.3 H$_2$O molar eq) with 0.01 N HCl, 5% C8-TES fully hydrolysed (3.3 H$_2$O molar eq) with 0.05 N HCl and 80% TEOS partially hydrolysed (1.1 H$_2$O molar eq) with HCl 0.01 N were prepared using the general procedure. The main characteristics of the obtained core-shell sub-micron/microcapsules in microcapsules are summarised in FIG. 6 and Table 6.

EXAMPLE 10-3: Core-shell sub-micron/microcapsules in microcapsules containing 22.5% C1-TES fully hydrolysed (3.3 H$_2$O molar eq) with 0.01 N HCl, 5% C8-TES fully hydrolysed (3.3 H$_2$O molar eq) with 0.05 N HCl and 72.5% TEOS partially hydrolysed (1.1 H$_2$O molar eq) with HCl 0.01 N were prepared using the general procedure. The main characteristics of the obtained core-shell sub-micron/microcapsules in microcapsules are summarised in FIG. 6 and Table 6.

EXAMPLE 10-4: Core-shell sub-micron/microcapsules in microcapsules containing 22.5% C1-TES fully hydrolysed (3.3 H$_2$O molar eq) with 0.01 N HCl, 7.5% C8-TES fully hydrolysed (3.3 H$_2$O molar eq) with 0.05 N HCl and 70% TEOS partially hydrolysed (1.1 H$_2$O molar eq) with HCl 0.01 N were prepared using the general procedure. The main characteristics of the obtained core-shell sub-micron/microcapsules in microcapsules are summarised in FIG. 6 and Table 6.

Thus, obtained core-shell sub-micron/microcapsules in microcapsules contain around 5 wt % all-trans-retinol active based on the total mass of the product excluding the water content.

TABLE 6

Size and porosity data of examples of core-shell sub-micron/microcapsules in microcapsules with different silica precursors compositions:

| Examples | Yield Retinol (%) | Particle size | | N$_2$ isotherm analysis | | |
|---|---|---|---|---|---|---|
| | | d50 (μm) | d90/d10 | Surface area ($m^2 \cdot g^{-1}$) | Pore volume ($cm^3 \cdot g^{-1}$) | Average pore size (nm) |
| Example 10-1 | 90 | 5.0 | 8.2 | 557 | 0.33 | 2.4 |
| Example 10-2 | 90 | 14.0 | 8.3 | 447 | 0.30 | 2.7 |
| Example 10-3 | 95 | 19.0 | 11.0 | 372 | 0.25 | 2.7 |
| Example 10-4 | 97 | 13.0 | 11.4 | 423 | 0.34 | 3.2 |

EXAMPLE 11: Core-shell sub-micron/microcapsules in microcapsules with C1-TES and TEOS in a molar ratio of 10%/90% and with the presence of 50 wt % payload (all-trans-retinol mixture oil) loading. The active was stabilised by different antioxidants.

Figure 7:
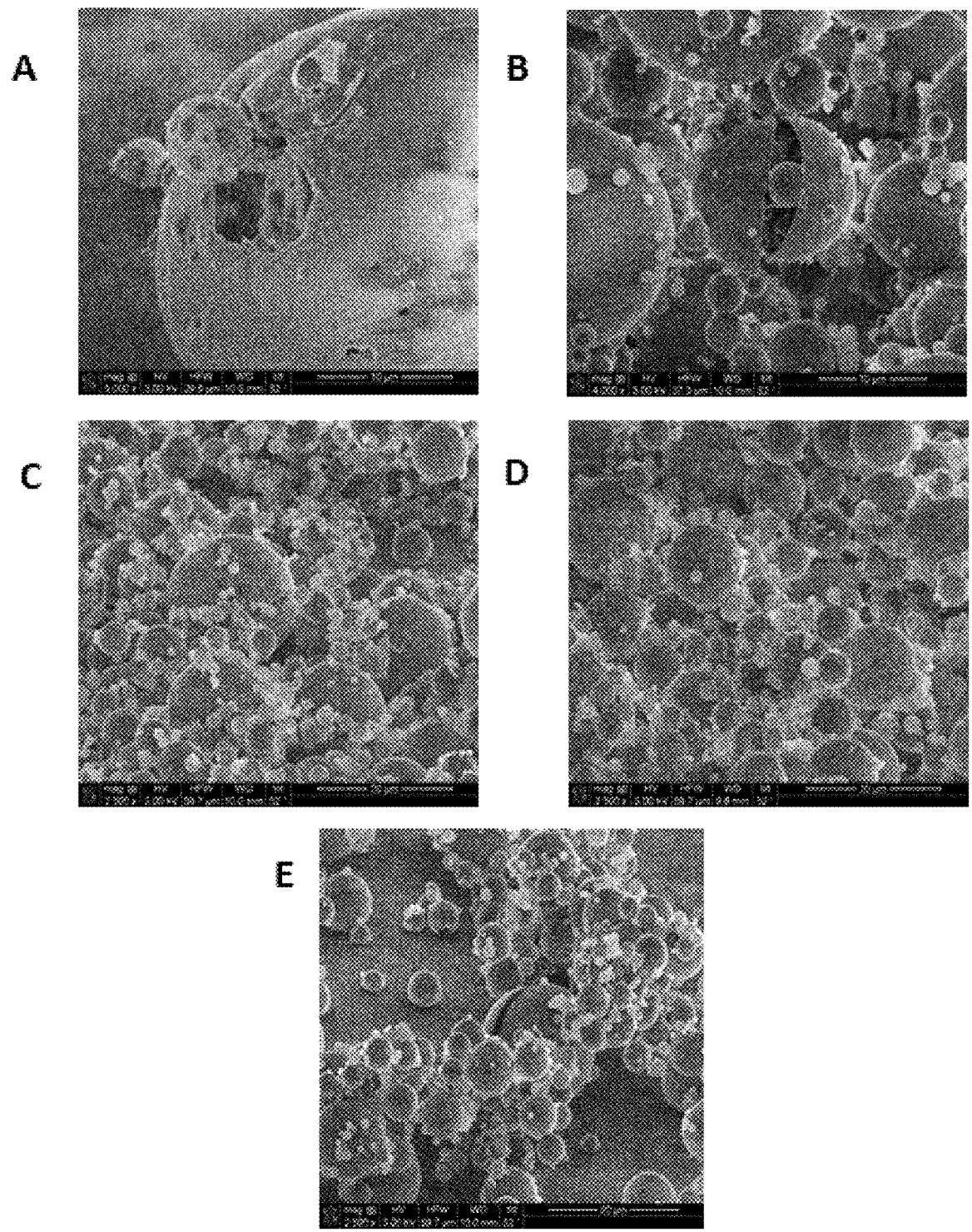
FIG. 7. SEM images of the examples of core-shell sub-micron/microcapsules in microcapsules containing different retinol mixture compositions. A) Example 11-1 (scale bar=10 μm), B) Example 11-2 (scale bar=10 μm) and C) Example 11-3 (scale bar=20 μm). D) Example 11-4 (scale bar=20 μm), E) Example 11-5 (scale bar=20 μm).

EXAMPLE 11-1: Core-shell sub-micron/microcapsules in microcapsules containing C1-TES and TEOS in a molar ratio of 10%/90% and 50 wt % payload loading (15 g mixture containing 1.50 g of all-trans-retinol and 13.5 g of caprylic capric oil, respectively, 10 and 90 wt % composition) were prepared using the general procedure. The main characteristics of the obtained core-shell sub-micron/microcapsules in microcapsules are summarised in FIG. 7 and Table 7.

EXAMPLE 11-2: Core-shell sub-micron/microcapsules in microcapsules containing 10% C1-TES and 90% TEOS and 50 wt % payload loading (15 g mixture containing 1.50 g of all-trans-retinol, 3.0 g of tocopherols mixture and 10.5 g of caprylic capric oil, respectively 10, 20, and 70 wt % composition) were prepared. See Experiment 1.2. The main characteristics of the obtained core-shell sub-micron/microcapsules in microcapsules are summarised in FIG. 7 and Table 7.

EXAMPLE 11-3: Core-shell sub-micron/microcapsules in microcapsules containing 10% C1-TES and 90% TEOS and 50 wt % payload loading (15 g mixture containing 1.50 g of all-trans-retinol, 0.3 g of hesperetin and 13.2 g of caprylic capric oil, respectively 10, 2, and 88 wt % compositions) were prepared using the general procedure. The main characteristics of the obtained core-shell sub-micron/microcapsules in microcapsules are summarised in FIG. 7 and Table 7.

EXAMPLE 11-4: Core-shell sub-micron/microcapsules in microcapsules containing 10% C1-TES and 90% TEOS and 50 wt % payload loading (15 g mixture containing 1.50 g of all-trans-retinol, 0.3 g of coenzyme Q10 and 13.2 g of caprylic capric oil triglyceride, respectively 10, 2, and 88 wt % composition) were prepared using the general procedure. The main characteristics of the obtained core-shell sub-micron/microcapsules in microcapsules are summarised in FIG. 7 and Table 7.

EXAMPLE 11-5: Core-shell sub-micron/microcapsules in microcapsules containing 10% C1-TES and 90% TEOS and 50 wt % payload loading (15 g mixture containing 1.50 g of all-trans-retinol, 0.3 g of BHT and 13.2 g of caprylic capric oil, respectively 10, 2, and 88 wt % composition) were prepared using the general procedure. The main characteristics of the obtained core-shell sub-micron/microcapsules in microcapsules are summarised in FIG. 7 and Table 7.

Thus, obtained core-shell sub-micron/microcapsules in microcapsules contain around 5 wt % all-trans-retinol based on the total mass of the product excluding the water content.

TABLE 7

Size and porosity data of examples of core-shell sub-micron/microcapsules in microcapsules with all-trans-retinol protected by different antioxidants:

| | Particle size | | $N_2$ isotherm analysis | | |
|---|---|---|---|---|---|
| Examples | d50 (μm) | d90/d10 | Surface area ($m^2 \cdot g^{-1}$) | Pore volume ($cm^3 \cdot g^{-1}$) | Average pore size (nm) |
| Example 11-1 | 11 | 3.1 | 496.0 | 0.30 | 2.4 |
| Example 11-2 | 14.0 | 3.0 | 0.0 | 0.0 | 0.0 |
| Example 11-3 | 12 | 3.3 | 181.0 | 0.15 | 3.3 |
| Example 11-4 | 11 | 2.8 | 326.3 | 0.22 | 2.7 |
| Example 11-5 | 11 | 2.5 | 366.0 | 0.25 | 2.7 |

Example 12: Core-shell sub-micron/microcapsules in microcapsules with 10% C1-TES and 90% TEOS and with 50 wt % payload (retinol mixture oils) loading containing different sources of retinol.

Figure 8:
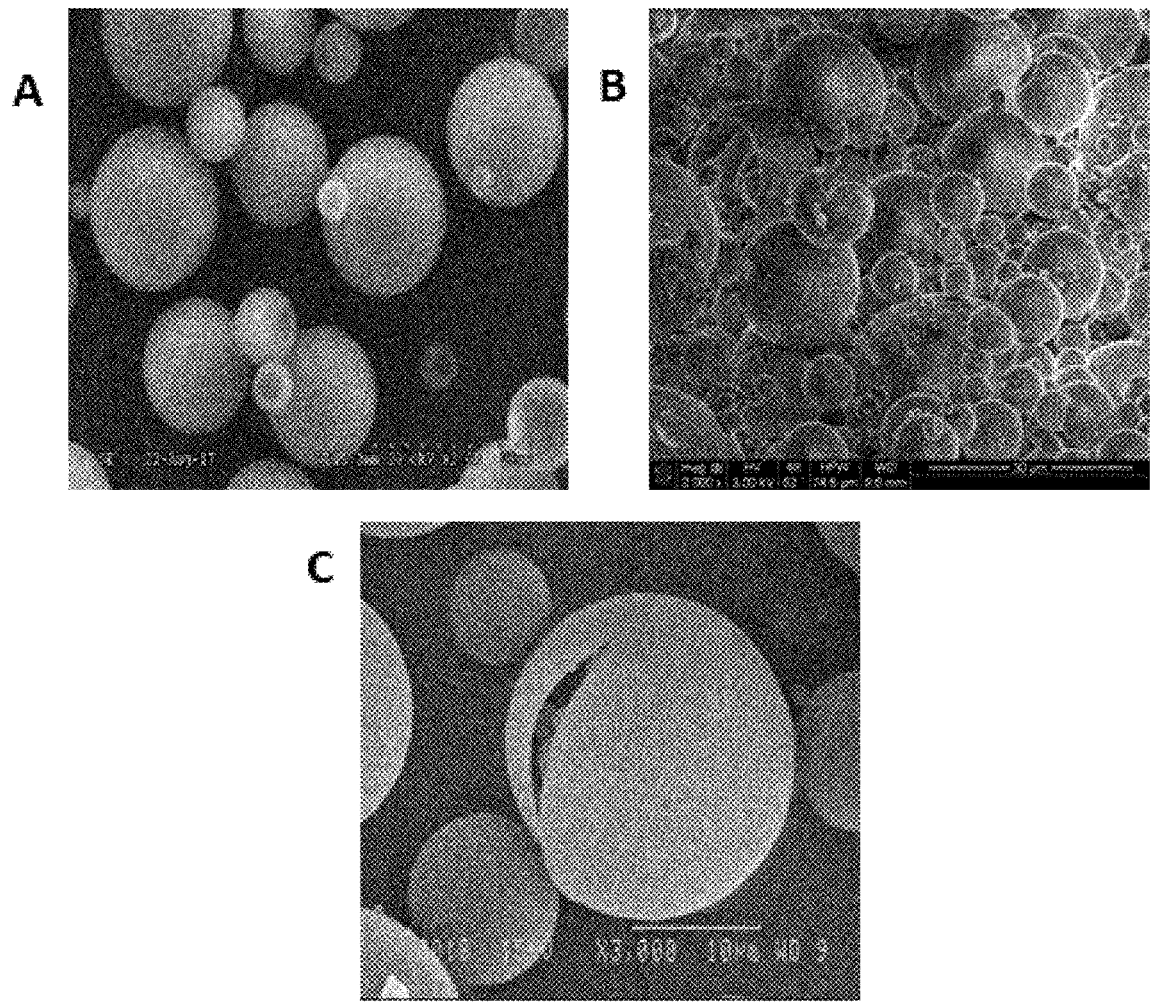
FIG. 8. SEM images of the examples of core-shell sub-micron/microcapsules in microcapsules containing different sources of retinol. A/B) Example 12-1 (scale bar=20/30 μm), C) Example 12-2 (scale bar=10 μm)

EXAMPLE 12-1: Core-shell sub-micron/microcapsules in microcapsules containing 10% C1-TES and 90% TEOS and 50 wt % payload (retinyl acetate mixture oil) loading (15 g mixture containing 2.25 g of retinyl acetate and 12.75 g of corn oil, respectively 15 and 85 wt % composition) were prepared using the general procedure. The main characteristics of the obtained core-shell sub-micron/microcapsules in microcapsules are summarised in FIG. 8 and Table 8.

EXAMPLE 12-2: Core-shell sub-micron/microcapsules in microcapsules containing 10% C1-TES and 90% TEOS and 50 wt % payload loading (15 g retinol 15D de BASF containing 2.25 g of all-trans retinol, 0.3 g of BHT and 12.45 g of caprylic capric oil, respectively 15, 2, and 83 wt % composition) were prepared using the general procedure. The main characteristics of the obtained core-shell sub-micron/microcapsules in microcapsules are summarised in FIG. 8 and Table 8.

Thus, obtained core-shell sub-micron/microcapsules in microcapsules contain around 7.5 wt % all-trans-retinol relative to the total mass of the product, excluding the water content.

TABLE 8

Size and porosity data of examples of core-shell sub-micron/microcapsules in microcapsules containing different sources of retinol.

| | Yield | Particle size | | $N_2$ isotherm analysis | | |
|---|---|---|---|---|---|---|
| Examples | Retinol (%) | d50 (μm) | d90/d10 | Surface area ($m^2 \cdot g^{-1}$) | Pore volume ($cm^3 \cdot g^{-1}$) | Average pore size (nm) |
| Example 12-1 | 85% | 7 | 7.0 | 0.0 | 0.0 | 7 |
| Example 12-2 | 84% | 6 | 7.5 | 0.0 | 0.0 | 6 |

Example 13: Core-shell sub-micron/microcapsules in microcapsules with 10% C1-TES and 90% TEOS and with the presence of different payloads. In the payload the active is dissolved in triglyceride oils. The active can be pure oil or an essential oil, a perfume or a fragrance.

Figure 9:
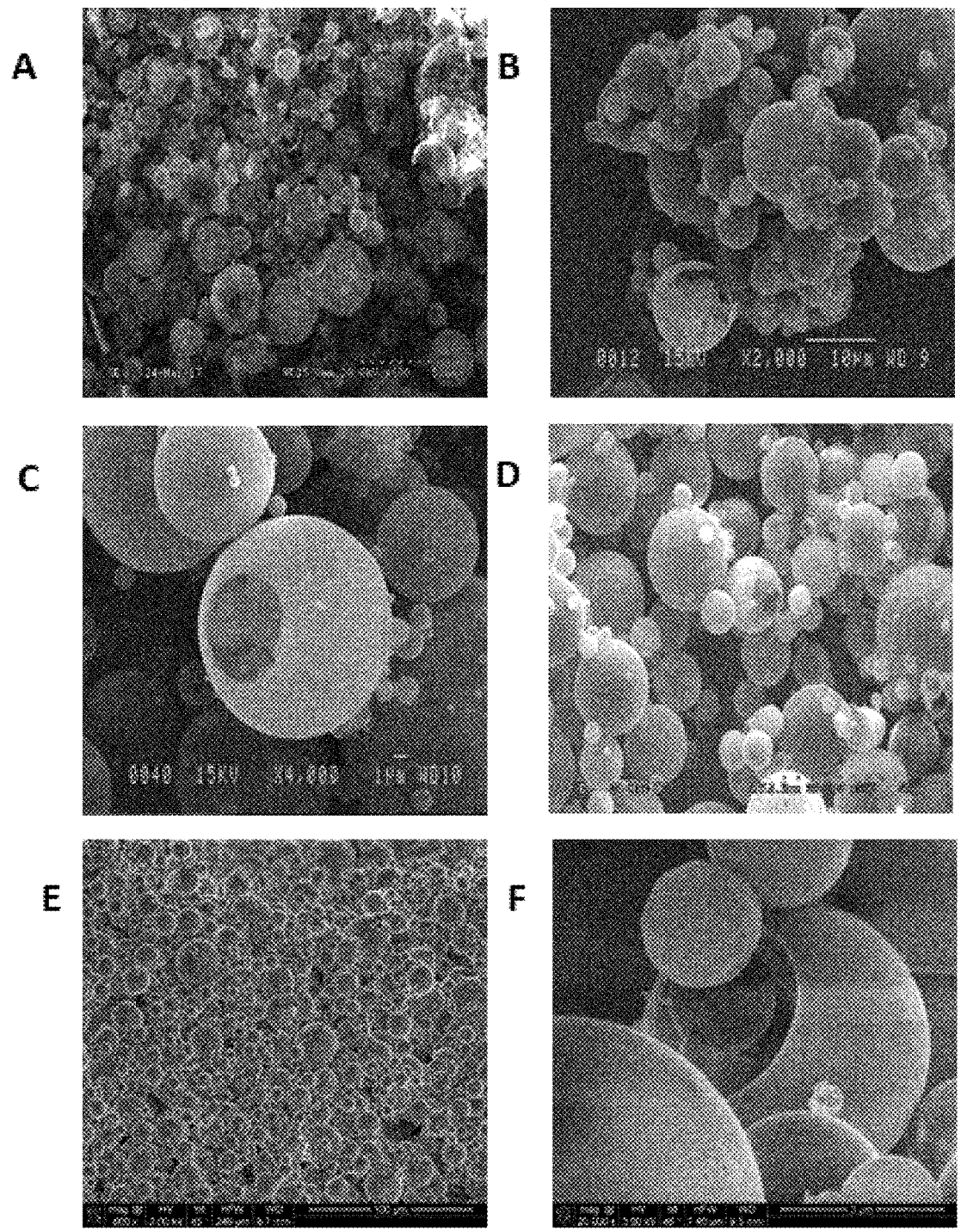
FIG. 9. SEM images of the examples of core-shell sub-micron/microcapsules in microcapsules with other actives dissolved in triglyceride oils. A) Example 13-1 (scale bar=20 μm), B) Example 13-2 (scale bar=10 μm). C) Example 13-3 (scale bar=1 μm), D) Example 13-4 (scale bar=50 μm). E) Example 13-5 (scale bar=100 μm). F) Example 13-6 (scale bar=20 μm). G) Example 13-7 (scale bar=3 μm).

EXAMPLE 13-1: Core-shell sub-micron/microcapsules in microcapsules containing 50 wt % payload loading (15 g of pure caprylic capric oil) were prepared using the general procedure. For this active the inert conditions are not necessary. The main characteristics of the obtained core-shell sub-micron/microcapsules in microcapsules are summarised in FIG. 9 and Table 9.

EXAMPLE 13-2: Core-shell sub-micron/microcapsules in microcapsules containing 50 wt % payload loading (15 g mixture: 2.25 g of black spruce and 12.75 g of caprylic capric oil, respectively 15 and 85 wt % composition) were prepared using the general procedure. For this active the inert conditions are not necessary. The main characteristics of the obtained core-shell sub-micron/microcapsules in microcapsules are summarised in FIG. 9 and Table 9.

EXAMPLE 13-3: Core-shell sub-micron/microcapsules in microcapsules containing 10% C1-TES and 90% TEOS and 50 wt % payload loading (15 g mixture: 2.25 g of alpha-pinene and 12.75 g of caprylic capric oil, respectively 15 and 85 wt % composition) were prepared using the general procedure. For this active the inert conditions are not necessary. The main characteristics of the obtained core-shell sub-micron/microcapsules in microcapsules are summarised in FIG. 9 and Table 9.

EXAMPLE 13-4: Core-shell sub-micron/microcapsules in microcapsules containing 10% C1-TES and 90% TEOS and 50 wt % active loading (15 g mixture: 2.25 g of alpha-pinene and 12.75 g of sunflower oil, respectively 15 and 85 wt % composition) were prepared using the general procedure. For this active the inert conditions are not necessary. The main characteristics of the obtained core-shell sub-micron/microcapsules in microcapsules are summarised in FIG. 9 and Table 9.

EXAMPLE 13-5: Core-shell sub-micron/microcapsules in microcapsules containing 10% C1-TES and 90% TEOS and 50 wt % active loading (15 g mixture: 2.25 g of bornyl acetate and 12.75 g of caprylic capric oil, respectively 15 and 85 wt % composition) were prepared using the general procedure. For this active the inert conditions are not necessary. The main characteristics of the obtained core-shell sub-micron/microcapsules in microcapsules are summarised in FIG. 9 and Table 9.

EXAMPLE 13-6: Core-shell sub-micron/microcapsules in microcapsules containing 10% C1-TES and 90% TEOS and 50 wt % payload loading (15 g mixture: 2.25 g of menthol and 12.75 g of caprylic capric oil, respectively 15 and 85 wt % composition) were prepared using the general procedure. For this active the inert conditions are not necessary. The main characteristics of the obtained core-shell sub-micron/microcapsules in microcapsules are summarised in FIG. 9 and Table 9.

Thus, obtained microcapsules contain around 7.5% of active relative to the total mass of the product excluding the water content.

TABLE 9

Size and porosity data of examples of core-shell sub-micron/microcapsules in microcapsules with other actives dissolved in triglyceride oils.

Figure 10:
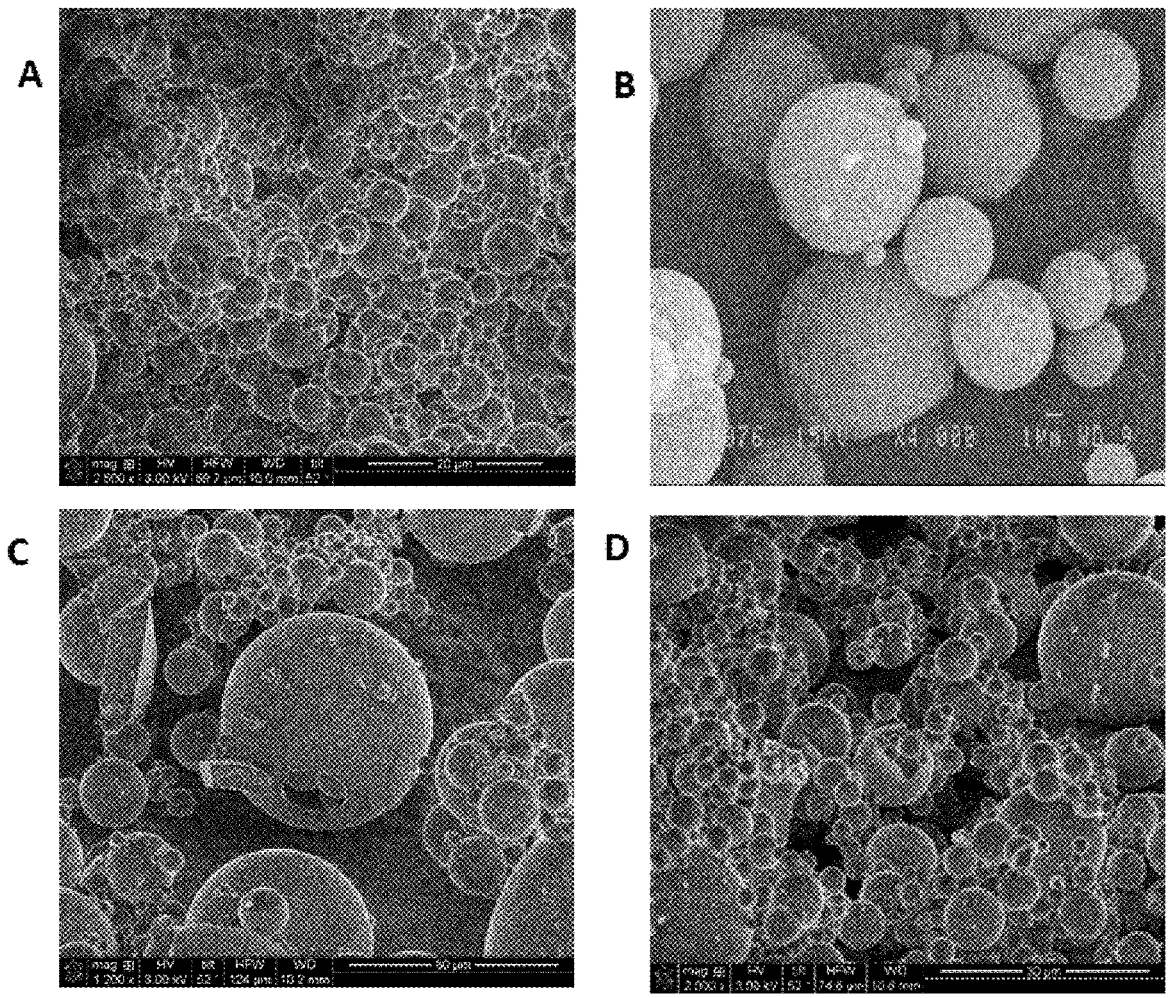
FIG. 10. SEM images of the examples of core-shell sub-micron/microcapsules in microcapsules with different pure actives. A) Example 14-1 (scale bar=20 μm), B) Example 14-1 (scale bar=1 μm), C) Example 14-2 (scale bar=50 μm), D) Example 14-3 (scale bar=30 μm).

| Examples | Particle size | | Porosity | |
|---|---|---|---|---|
| | d50 (µm) | d90/d10 | Surface area ($m^2 \cdot g^{-1}$) | Pore volume ($cm^3 \cdot g^{-1}$) |
| Example 13-1 | 17 | 0.0 | 0.0 | 0.0 |
| Example 13-2 | 10 | 7.6 | 2.0 | 0.0 |
| Example 13-3 | 11 | 10.4 | 0.0 | 0.0 |
| Example 13-4 | 14 | 7.5 | 0.0 | 0.0 |
| Example 13-5 | 14 | 9.7 | 5.0 | 0.0 |
| Example 13-6 | 14 | 9.0 | 0.0 | 0.0 | istics of the obtained core-shell sub-micron/microcapsules in microcapsules are summarised in FIG. 10 and Table 10.

EXAMPLE 14-3: Core-shell sub-micron/microcapsules in microcapsules containing 22.5% C1-TES fully hydrolysed (3.3 $H_2O$ molar eq) with 0.01 N HCl, 7.5% C8-TES fully hydrolysed (3.3 $H_2O$ molar eq) with 0.05 N HCl and 70% TEOS partially hydrolysed (1.1 $H_2O$ molar eq) with HCl 0.01 N and 50 wt % payload loading (15 g of black spruce) were prepared using the general procedure. For this active the inert conditions are not necessary. The main characteristics of the obtained core-shell sub-micron/microcapsules in microcapsules are summarised in FIG. 10 and Table 10.

EXAMPLE 14-4: Core-shell sub-micron/microcapsules in microcapsules containing 22.5% C1-TES and 7.5% C8-TES and 70% TEOS and 50 wt % payload loading (16.5 g, pure grapefruit seed extract) were prepared by using the same procedure as described in Example 14-3. The main characteristics of the obtained core-shell sub-micron/microcapsules in microcapsules are summarised in FIG. 10 and Table 10.

Thus, obtained capsules contain around 50 wt % of active based on the total mass of the product excluding the water content.

TABLE 10

Size and porosity data of examples of core-shell sub-micron/microcapsules in microcapsules with different pure actives.

| Examples | Yield active (%) | Particle size | | $N_2$ isotherm analysis | | |
|---|---|---|---|---|---|---|
| | | d50 (µm) | d90/d10 | Surface area ($m^2 \cdot g^{-1}$) | Pore volume ($cm^3 \cdot g^{-1}$) | Average pore size (nm) |
| Example 14-1 | 96 | 7 | 2.6 | 0.0 | 0.0 | 0.0 |
| Example 14-2 | 95 | 11 | 3.9 | 572.0 | 2.46 | 17.2 |
| Example 14-3 | 83 | 12 | 7.6 | 802.0 | 0.84 | 4.2 |
| Example 14-4 | 90 | 9 | 7.1 | 693.9 | 0.98 | 5.7 |

Example 14: Core-shell sub-micron/microcapsules in microcapsules with different payloads containing pure actives. The active can be an essential oil, a perfume or a fragrance.

EXAMPLE 14-1: Core-shell sub-micron/microcapsules in microcapsules containing 100% C1-TES and 50 wt % payload loading (15 g of pure geraniol) were prepared using the general procedure. For this active the inert conditions are not necessary. The main characteristics of the obtained core-shell sub-micron/microcapsules in microcapsules are summarised in FIG. 10 and Table 10.

EXAMPLE 14-2: Core-shell sub-micron/microcapsules in microcapsules containing 10% C1-TES and 90% TEOS and 50 wt % payload loading (15 g of pure black spruce) were prepared using the general procedure. For this active the inert conditions are not necessary. The main character- Examples of Core-Shell Sub-Micron/Microcapsules EXAMPLE 15: Core-shell sub-micron/microcapsules with 10% C1-TES and 90% TEOS and with presence of 50 wt % of different payloads. In the payload the active was dissolved in mineral oil.

Figure 11:
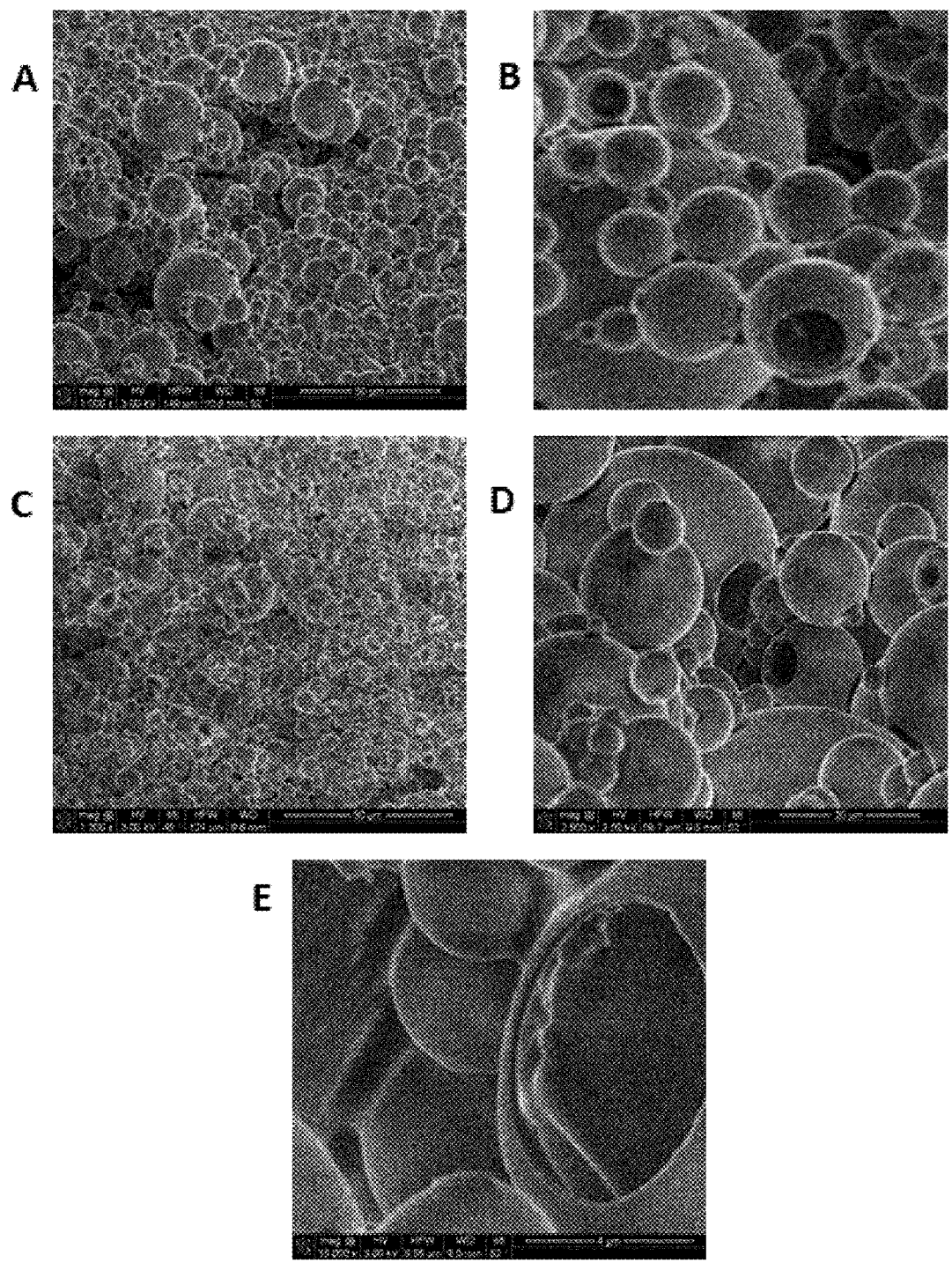
FIG. 11. SEM images of the examples of core-shell sub-micron/microcapsules with different payloads (the actives were dissolved in mineral oil): A-B) Example 15-1 (scale bar=50 μm), C) Example 15-2 (scale bar=50 μm), D/E) Example 16 (scale bar=20/50 μm).

EXAMPLE 15-1: Core-shell sub-micron/microcapsules containing 10% C1-TES and 90% TEOS and with the presence of 50 wt % payload (all-trans-retinol mixture oils) loading (15 g mixture containing 1.5 g of all-trans retinol, 3.0 g tocopherols mixtures, and 10.5 g of mineral oil, respectively 10, 20, and 70 wt % composition) were prepared using the general procedure. The main characteristics of the obtained core-shell sub-micron/microcapsules are summarised in FIG. 11 and Table 11.

Thus, obtained core-shell microcapsules contain around 5 wt % of all-trans-retinol active based on the total mass of the product excluding the water content.

EXAMPLE 15-2: Core-shell sub-micron/microcapsules containing 10% C1-TES and 90% TEOS and with the presence of 50 wt % payload (bornyl acetate mixture oils) loading (15 g mixture: 2.25 g of bornyl acetate and 12.75 g of mineral oil, respectively 15 and 85 wt % composition) were prepared using the general procedure. For this active the inert conditions are not necessary. The main characteristics of the obtained core-shell sub-micron/microcapsules are summarised in FIG. 11 and Table 11.

Thus, obtained core-shell microcapsules contain around 7.22 wt % (96% yields) of bornyl acetate active based on the total mass of the product excluding the water content.

EXAMPLE 16: Core-shell sub-micron/microcapsules with 10% C1-TES and 90% TEOS and with the presence of 70% payload (all-trans-retinol mixture oils) loading. The active was dissolved in mineral oil.

Core-shell sub-micron/microcapsules containing 10% C1-TES and 90% TEOS and with the presence of 70 wt % payload loading (34 g mixture containing 3.40 g of all-trans retinol, 6.80 g tocopherols mixtures, and 23.80 g of mineral oil, respectively 10, 20, and 70 wt % composition) were prepared using the general procedure. The main characteristics of the obtained core-shell sub-micron/microcapsules are summarised in FIG. 11 and Table 11.

Figure 12:
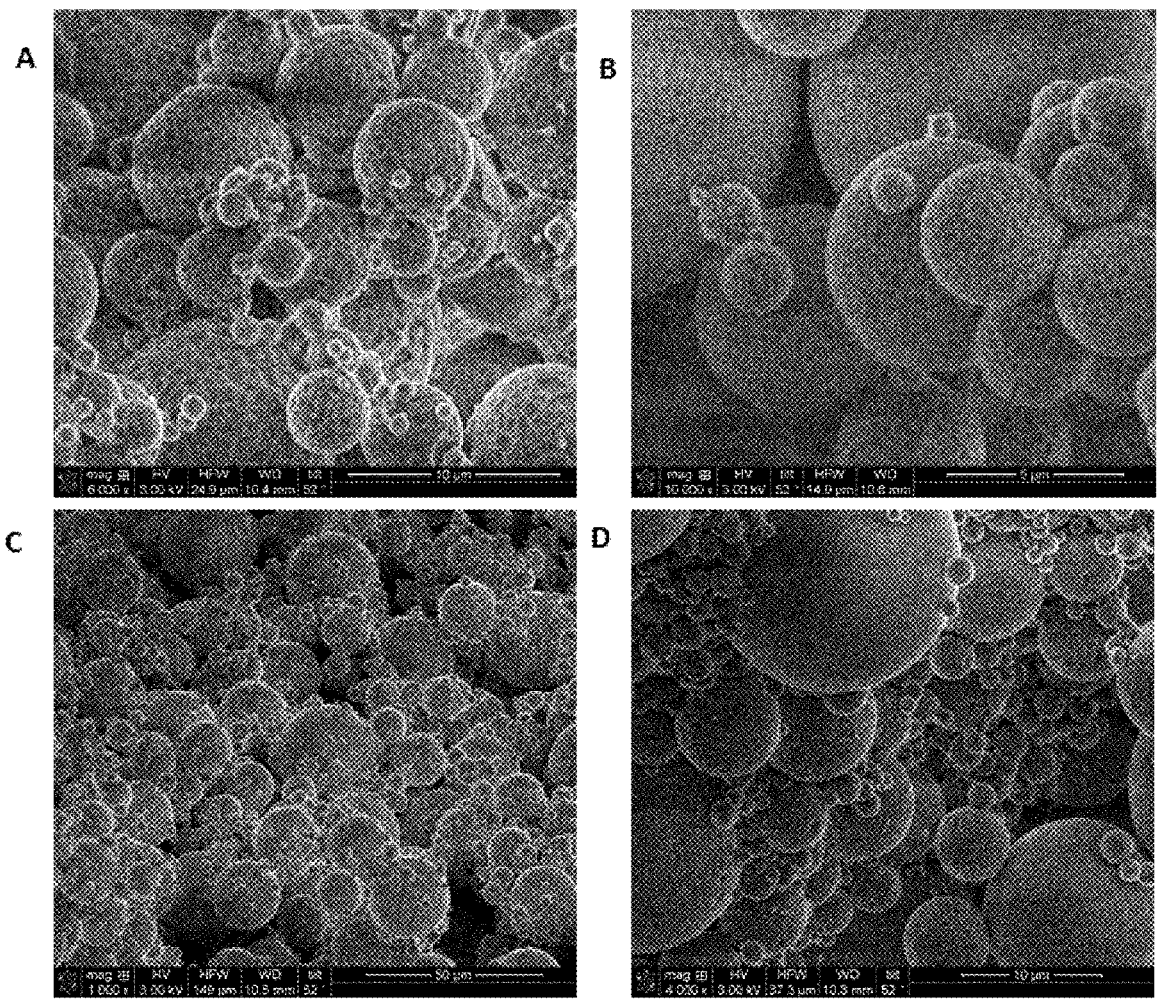
FIG. 12. SEM images of the examples of porous solid sub-micron/microsphere with different silica precursor compositions. A) Example 17-1 (scale bar=10 μm), B) Example 17-(scale bar=5 μm) and C) Example 17-3 (scale bar=10 μm). C) Example 17-4 (scale bar=50 μm).

Thus, obtained core-shell microcapsules contain around 7.5 wt % of all-trans-retinol active based on the total mass of the product excluding the water content.

dure. The main characteristics of the obtained porous solid sub-micron/microspheres are summarised in FIG. 12 and Table 12.

EXAMPLE 17-3: Porous solid sub-micron/microspheres containing 2.5% C18-TES fully hydrolysed (3.3 $H_2O$ molar eq) with 0.05 N HCl, 20% C1-TES fully hydrolysed (3.3 $H_2O$ molar eq) with 0.01 N HCl, and 77.5% TEOS partially hydrolysed (1.1 $H_2O$ molar eq) with 0.01 N HCl and 50 wt % payload loading were prepared using the general procedure. The main characteristics of the obtained porous solid sub-micron/microspheres are summarised in FIG. 12 and Table 12.

EXAMPLE 17-4: Porous solid sub-micron/microspheres containing 5% C18-TES fully hydrolysed (3.3 $H_2O$ molar eq) with 0.05 N HCl, 10% C1-TES fully hydrolysed (3.3 $H_2O$ molar eq) with 0.01 N HCl, and 85% TEOS partially hydrolysed (1.1 $H_2O$ molar eq) with 0.01 N HCl and 50 wt % payload loading were prepared using the general procedure. The main characteristics of the obtained porous solid sub-micron/microspheres are summarised in FIG. 12 and Table 12.

Thus, obtained porous solid sub-micron/microsphere contain around 5 wt % of all-trans-retinol active based on the total mass of the product excluding the water content.

TABLE 11

Size and porosity data of examples of core-shell sub-micron/microcapsules with different payloads (the actives were dissolved in mineral oil).

| Examples | Yield active (%) | Particle size d50 (μm) | d90/d10 | $N_2$ isotherm analysis Surface area ($m^2 \cdot g^{-1}$) | Pore volume ($cm^3 \cdot g^{-1}$) | Average pore size (nm) |
|---|---|---|---|---|---|---|
| Example 15-1 | 83 | 18 | 3.9 | 7.0 | 0.0 | 0.0 |
| Example 15-2 | 98 | 12 | 4.2 | 0.0 | 0.0 | 0.0 |
| Example 16 | 96 | 26 | 3.5 | 428.0 | 0.29 | 2.6 |

Examples of Porous Microspheres

EXAMPLE 17: Porous solid sub-micron/microspheres with different silica precursor compositions and with the presence of wt % payload (all-trans-retinol mixture oils) loading: 15 g mixture containing 1.50 g of all-trans-retinol, 3.0 g of tocopherols mixture and 10.5 g of caprylic capric oil triglyceride, respectively, 10, 20, and 70 wt % composition).

EXAMPLE 17-1: Porous solid sub-micron/microspheres containing 10% C8-TES fully hydrolysed (3.3 $H_2O$ molar eq) with 0.05 N HCl and 90% TEOS partially hydrolysed (1.1 $H_2O$ molar eq) with HCl 0.01 N and 50 wt % payload loading were prepared using the general procedure. The main characteristics of the obtained porous solid sub-micron/microspheres are summarised in FIG. 12 and Table 12.

EXAMPLE 17-2: Porous solid sub-micron/microspheres containing 2.5% C18-TES fully hydrolysed (3.3 $H_2O$ molar eq) with 0.05 N HCl, 10% C1-TES fully hydrolysed (3.3 $H_2O$ molar eq) with 0.01 N HCl, and 87.25% TEOS partially hydrolysed (1.1 $H_2O$ molar eq) with 0.01 N HCl and 50 wt % payload loading were prepared using the general proce-

TABLE 12

Size and porosity data of examples of porous solid sub-micron/microsphere with different silica precursor compositions:

| Examples | Particle size d50 (μm) | d90/d10 | $N_2$ isotherm analysis Surface area ($m^2 \cdot g^{-1}$) | Pore volume ($cm^3 \cdot g^{-1}$) | Average pore size (nm) |
|---|---|---|---|---|---|
| Example 17-1 | 7.0 | 4.3 | 615 | 0.78 | 5.1 |
| Example 17-2 | 8.0 | 6.5 | 507 | 1.18 | 9.3 |
| Example 17-3 | 16.0 | 6.4 | 585 | 1.21 | 8.3 |
| Example 17-4 | 8.0 | 11.5 | 199 | 0.21 | 4.2 |

EXAMPLE 18: Porous solid sub-micron/microspheres with 2.5% C18-TES and 10% C1-TES and 87.5% TEOS (see Example 17-2 for hydrolysis conditions) and with the presence of 50 wt % payload (all-trans-retinol mixture oils) loading. The all-trans-retinol active was stabilised by different antioxidants.

Figure 13:
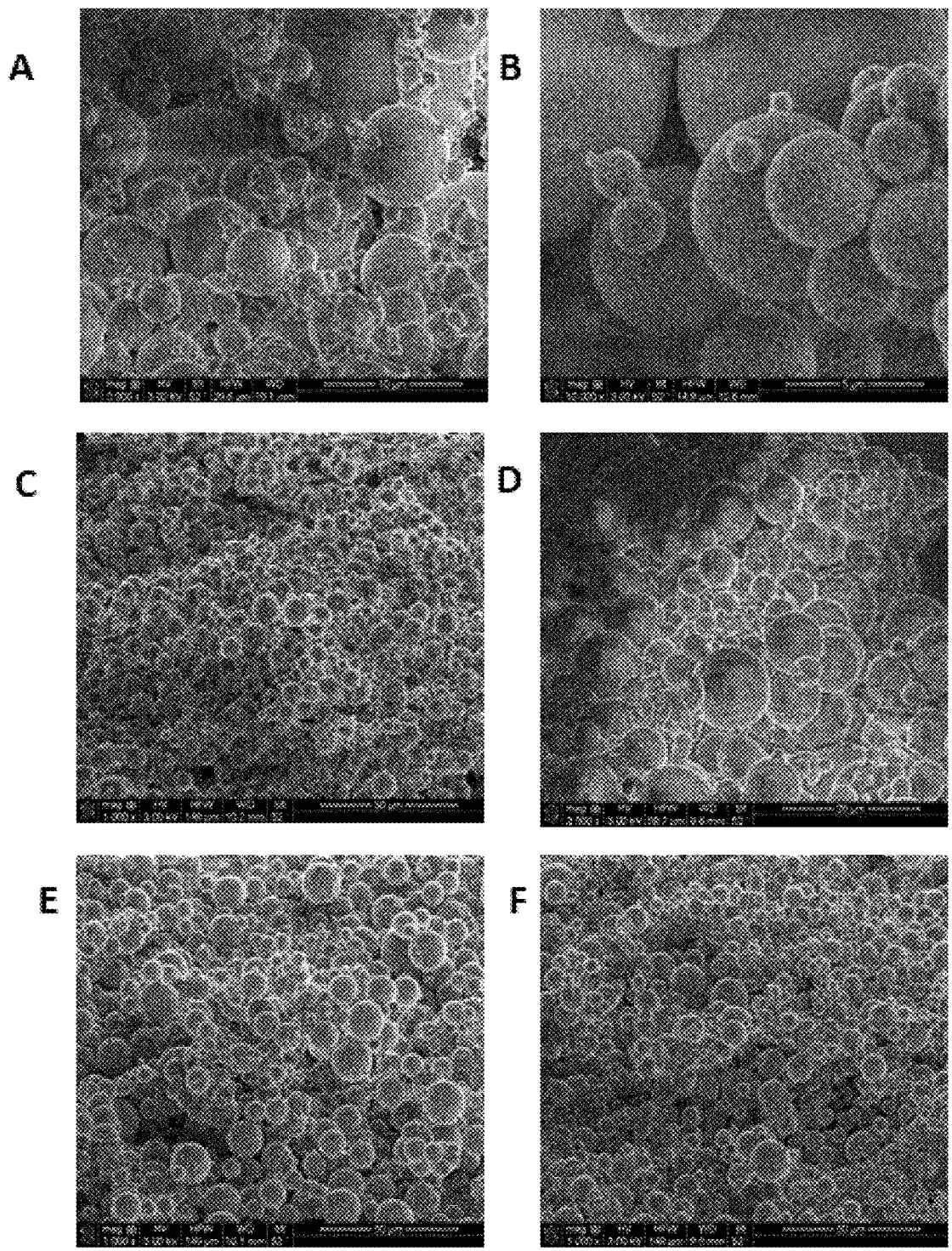
FIG. 13. SEM images of examples of porous solid sub-micron/microsphere with 2.5% C18-TES, 10% C1-TES and 87.5% TEOS compositions and with presence of 50 wt % payload loading. The retinol active was stabilised by different antioxidants. A) Example 18-1 (scale bar=10 µm), B) Example 18-2 (scale bar=5 µm), C) Example 18-3 (scale bar=50 µm), D) Example 18-4 (scale bar=20 µm), E) Example 18-5 (scale bar=50 µm), F) Example 18-6 (scale bar=50 µm).

EXAMPLE 18-1: Porous solid sub-micron/microspheres containing 2.5% C18-TES and 10% C1-TES and 87.5% TEOS and 50 wt % payload loading (15 g mixture containing 1.50 g of all-trans-retinol, 3.0 g of alpha-tocopherol, and 10.5 g of caprylic capric oil, respectively 10, 20, and 70 wt % composition) were prepared using the general procedure. The main characteristics of the obtained porous solid sub-micron/microspheres are summarised in FIG. 13 and Table 13.

EXAMPLE 18-2: Porous solid sub-micron/microspheres containing 2.5% C18-TES and 10% C1-TES and 87.5% TEOS and 50 wt % payload loading (15 g mixture containing 1.50 g of all-trans-retinol, 3.0 g of tocopherols mixture, and 10.5 g of caprylic capric oil, respectively 10, 20, and 70 wt % composition) were prepared. See Example 17-2. The main characteristics of the obtained porous solid sub-micron/microspheres are summarised in FIG. 13 and Table 13.

EXAMPLE 18-3: Porous solid sub-micron/microspheres containing 2.5% C18-TES and 10% C1-TES and 87.5% TEOS and 50 wt % payload loading (15 g mixture containing 1.50 g of all-trans-retinol, 3.0 g of tocopherols mixture, 0.3 g of Coenzyme Q10 and 10.2 g of caprylic capric oil, respectively 10, 20, 2, and 68 wt % composition) were prepared using the general procedure. The main characteristics of the obtained porous solid sub-micron/microspheres are summarised in FIG. 13 and Table 13.

EXAMPLE 18-4: Porous solid sub-micron/microspheres containing 2.5% C18-TES and 10% C1-TES and 87.5% TEOS and 50 wt % payload loading (15 g mixture containing 1.50 g of all-trans-retinol, 3.0 g of tocopherols mixture, 0.3 g of hesperetin and 10.2 g of caprylic capric oil triglyceride, respectively 10, 20, 2, and 68 wt % composition) were prepared using the general procedure. The main characteristics of the obtained porous solid sub-micron/microspheres are summarised in FIG. 13 and Table 13.

EXAMPLE 18-5: Porous solid sub-micron/microspheres containing 2.5% C18-TES and 10% C1-TES and 87.5% TEOS (see Example 17-2 for hydrolysis conditions) and 50 wt % payload loading (15 g mixture containing 1.50 g of all-trans-retinol, 3.0 g of tocopherols mixture, 0.3 g of ascorbyl palmitate and 10.2 g of caprylic capric oil, respectively 10, 20, 2, and 68 wt % composition) were prepared using the general procedure. The main characteristics of the obtained porous solid sub-micron/microspheres are summarised in FIG. 13 and Table 13.

EXAMPLE 18-6: Porous solid sub-micron/microspheres containing 2.5% C18-TES and 10% C1-TES and 87.5% TEOS and 50 wt % payload loading (15 g mixture containing 1.50 g of all-trans-retinol, 6.75 g of Tocoblend AT, 6.75 g of caprylic capric oil, respectively 10, 45, 45 wt % composition) were prepared using the general procedure. The main characteristics of the obtained porous solid sub-micron/microspheres are summarised in FIG. 13 and Table 13.

Thus, obtained porous solid sub-micron/microsphere contain around 5 wt % of all-trans-retinol active based on the total mass of the product excluding the water content.

TABLE 13

Size and porosity data of examples of porous solid sub-micron/microspheres with 2.5% C18-TES, 10% C1-TES and 87,5% TEOS compositions and with presence of 50 wt % payload loading. The retinol active was stabilised by different antioxidants:

| | Particle size | | $N_2$ isotherm analysis | | |
| | | | Surface | Pore | Average |
| Examples | d50 (µm) | d90/d10 | area ($m^2 \cdot g^{-1}$) | volume ($cm^3 \cdot g^{-1}$) | pore size (nm) |
| --- | --- | --- | --- | --- | --- |
| Example 18-1 | 13.3 | 5.7 | 513 | 1.41 | 11.0 |
| Example 18-2 | 8.0 | 2.6 | 569 | 1.53 | 10.8 |
| Example 18-3 | 7.0 | 2.8 | 546 | 1.16 | 8.5 |
| Example 18-4 | 4.0 | 2.75 | 566 | 1.17 | 82.5 |
| Example 18-5 | 7.0 | 6.0 | 534 | 0.92 | 6.9 |
| Example 18-6 | 11.0 | 8.00 | 585 | 1.20 | 8.2 |

EXAMPLE 19: Porous solid sub-micron/microspheres containing 2.5% C18-TES and 10% C1-TES and 87.5% TEOS composition (see Example 17-2 for hydrolysis conditions) and different wt % payload loading in different compositions (payload: all-trans-retinol mixture oils).

Figure 14:
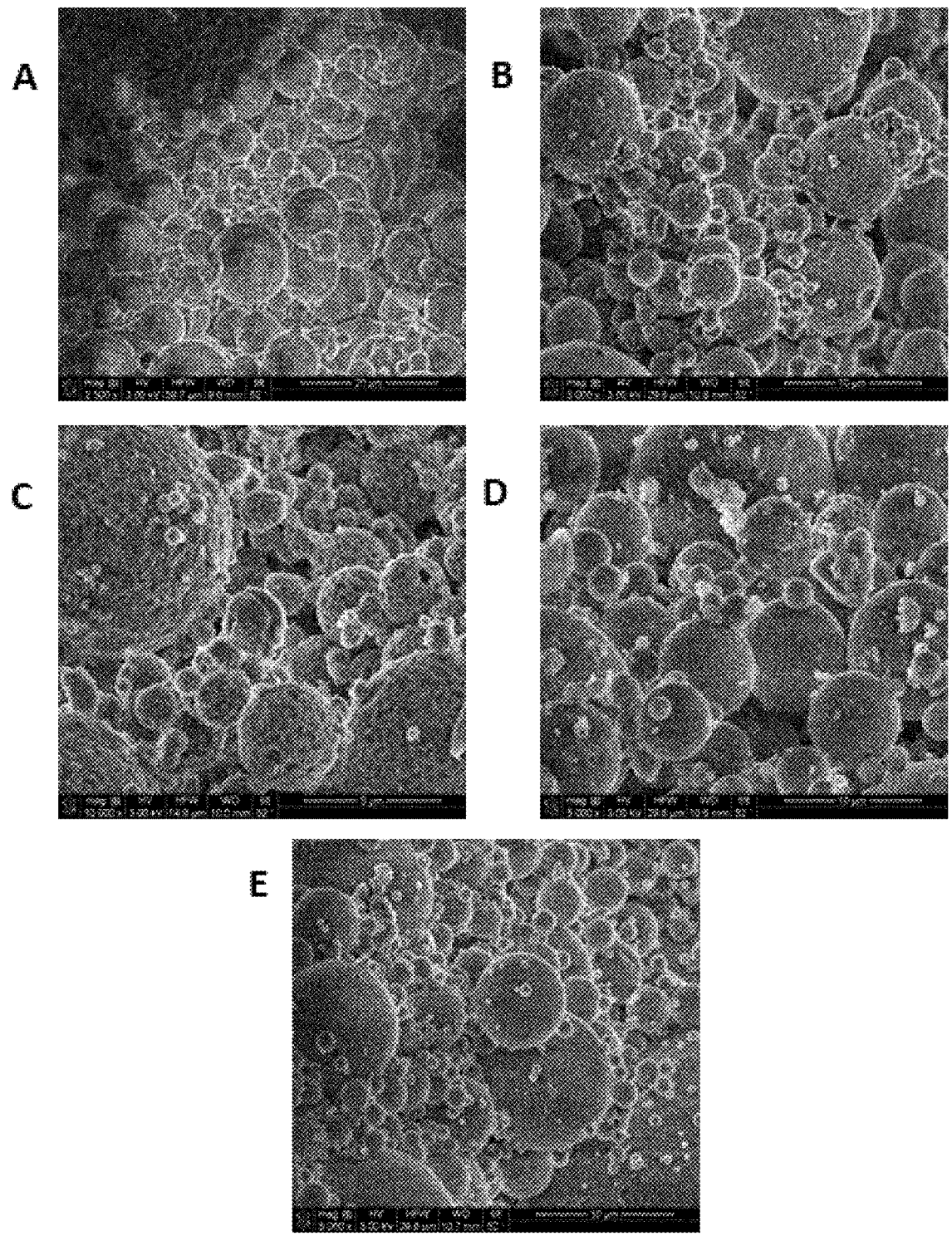
FIG. 14. SEM images of the examples of porous solid sub-micron/microsphere with 2.5% C18-TES, 10% C1-TES and 87.5% TEOS compositions and with presence of different wt % payload loading in different compositions: A) Example 19-1 (scale bar=20 µm), B) Example 19-2 (scale bar=10 µm), C) Example 19-3 (scale bar=5 µm), D) Example 19-4 (scale bar=10 µm), C) Example 19-5 (scale bar=10 µm).

EXAMPLE 19-1: Porous solid sub-micron/microspheres containing 50 wt % payload loading (15 g mixture containing 1.5 g of all-trans-retinol, 3.0 g of tocopherols mixture, 0.3 g of hesperetin and 10.2 g of caprylic capric oil, respectively 10, 20, 2, and 68 wt % composition) were prepared. See example 18-4. The main characteristics of the obtained porous solid sub-micron/microspheres are summarised in FIG. 14 and Table 14.

EXAMPLE 19-2: Porous solid sub-micron/microspheres containing 50 wt % payload loading (15 g mixture containing 2.25 g of all-trans-retinol, 4.5 g of tocopherols mixture, 0.45 g of hesperetin and 7.8 g of caprylic capric oil, respectively 15, 30, 3, and 52 wt % composition) were prepared using the general procedure. The main characteristics of the obtained porous solid sub-micron/microspheres are summarised in FIG. 14 and Table 14.

EXAMPLE 19-3: Porous solid sub-micron/microspheres containing 50 wt % payload loading (15 g mixture containing 3 g of all-trans-retinol, 6.0 g of tocopherols mixture, 0.6 g of hesperetin and 5.4 g of caprylic capric oil, respectively 20, 40, 4, and 36 wt % composition) were prepared using the general procedure. The main characteristics of the obtained porous solid sub-micron/microspheres are summarised in FIG. 14 and Table 14.

EXAMPLE 19-4: Porous solid sub-micron/microspheres containing and 50 wt % payload loading (15 g mixture containing 3.0 g of all-trans-retinol, 3.0 g of tocopherols mixture, 0.6 g of hesperetin and 8.4 g of caprylic capric oil, respectively 20, 20, 4.0, and 56 wt % composition) were prepared using the general procedure. The main characteristics of the obtained porous solid sub-micron/microspheres are summarised in FIG. 14 and Table 14.

EXAMPLE 19-5: Porous solid sub-micron/microspheres containing 60 wt % payload loading (23 g mixture containing 3.8 g of all-trans-retinol, 7.6 g of tocopherols mixture, 0.76 g of hesperetin and 10.9 g of caprylic capric oil, respectively 16.5, 33, 3.3, and 47.2 wt % composition) were prepared using the general procedure. The main characteristics of the obtained porous solid sub-micron/microspheres are summarised in FIG. 14 and Table 14.

Thus, obtained porous solid sub-micron/microspheres contain from 4.5 wt % to 10 wt % of all-trans-retinol active based on the total mass of the product excluding the water content.

TABLE 14

Porous solid sub-micron/microspheres with 2.5% C18-TES, 10% C1-TES and 87.5% TEOS compositions and with different wt % payload loading in different compositions (payload: all-trans-retinol mixture oils):

| Examples | Retinol loading (wt %) | Particle size | | $N_2$ isotherm analysis | | |
|---|---|---|---|---|---|---|
| | | d50 (μm) | d90/d10 | Surface area ($m^2 \cdot g^{-1}$) | Pore volume ($cm^3 \cdot g^{-1}$) | Average pore size (nm) |
| Example 19-1 | 4.9 | 7.0 | 2.75 | 566 | 1.16 | 8.2 |
| Example 19-2 | 7.3 | 6.5 | 5.6 | 486 | 0.64 | 5.3 |
| Example 19-3 | 10.0 | 10.0 | 9.6 | 497 | 0.56 | 4.5 |
| Example 19-4 | 9.7 | 21.0 | 25.0 | 537 | 1.01 | 7.5 |
| Example 19-5 | 7.2 | 12.0 | 3.5 | 538 | 1.50 | 11.2 |

EXAMPLE 20: Porous solid sub-micron/microspheres with various silica precursors compositions and with presence of different payloads. If the payload is not air sensitive, the atmosphere-controlled synthesis and storage under argon are not necessary.

Figure 15:
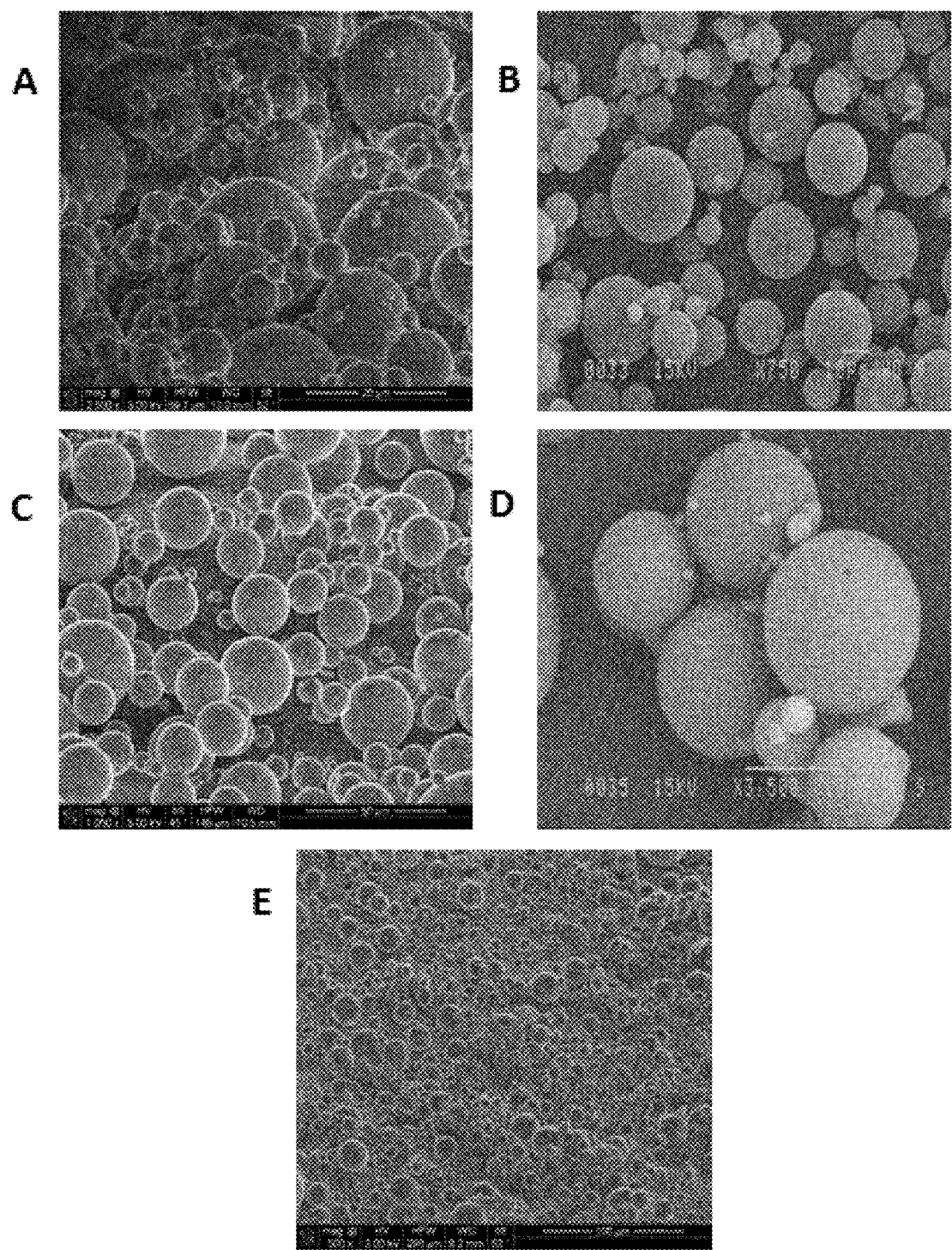
FIG. 15. SEM images of the examples of various organo-silica precursors compositions and with presence of different payloads. A) Example 20-1 (scale bar=20 µm), B) Example 20-1 (scale bar=10 µm), C) Example 20-2 (scale bar=10 µm) and D) Example 20-3 (scale bar=10 µm), E) Example 20-4 (scale bar=100 µm).

EXAMPLE 20-1: Porous solid sub-micron/microspheres containing 100% TEOS partially hydrolysed (1.1 $H_2O$ molar eq) in acidic conditions using 0.01 N HCl solution and 50 wt % payload loading (15 g of pure geraniol) were prepared using the general procedure. The main characteristics of the obtained porous solid sub-micron/microspheres are summarised in FIG. 15 and Table 15.

EXAMPLE 20-2: Porous solid sub-micron/microspheres containing 30% C1-TES and 70% TEOS and 70 wt % payload (pure black spruce essential oil) loading were prepared using the general procedure, excepted: for speed agitation of the emulsion process (3000 rpm), for the amount of dispersing phase that is two times less (164 g of water), and for the condensation agent quantity used (4 g of concentrated $NH_4OH$). The main characteristics of the obtained porous solid sub-micron/microspheres are summarised in FIG. 15 and Table 15.

EXAMPLE 20-3: Porous solid sub-micron/microspheres containing 30% C1-TES and 70% TEOS and 70 wt % payload (pure menthol) loading were prepared using the general procedure, excepted: for speed agitation of the emulsion process (3000 rpm), for the amount of dispersing phase that is two times less (164 g of water), and for the condensation agent quantity used (4 g of concentrated $NH_4OH$). The main characteristics of the obtained porous solid sub-micron/microspheres are summarised in FIG. 15 and Table 15.

EXAMPLE 20-4: Porous solid sub-micron/microspheres containing 50% C1-TES and 50% TEOS, with the presence of 50 wt % payload (pure black spruce essential oil) loading were prepared using the general procedure, excepted: for speed agitation of the emulsion process (3000 rpm), for the amount of dispersing phase that is two times less (164 g of water), and for the condensation agent quantity used (4 g of concentrated $NH_4OH$). The main characteristics of the obtained porous solid sub-micron/microspheres are summarised in FIG. 15 and Table 15.

EXAMPLE 20-5 Porous solid sub-micron/microspheres containing 7.5% C8-TES and 22.5% C1-TES and 70% TEOS and 20 wt % payload loading (pure gray pine essential oil) were prepared using the general procedure, excepted: for speed agitation of the emulsion process (3500 rpm), for the amount of dispersing phase that is two times less (164 g of water), and for the condensation agent used, NaOH (1 M), 5.5 g. The main characteristics of the obtained porous solid sub-micron/microspheres are summarised in FIG. 15 and Table 15.

TABLE 15

Size and porosity data of examples of various organosilica precursors compositions and with presence of different payloads:

| Examples | Payload loading (wt %) | Particle size | | $N_2$ isotherm analysis | | |
|---|---|---|---|---|---|---|
| | | d50 (μm) | d90/d10 | Surface area ($m^2 \cdot g^{-1}$) | Pore volume ($cm^3 \cdot g^{-1}$) | Average pore size (nm) |
| Example 20-1 | 50 | 11.0 | 4.0 | 472 | 1.87 | 15.8 |
| Example 20-2 | 70 | 23.4 | 3.8 | 747 | 2.33 | 12.4 |
| Example 20-3 | 70 | 25.8 | 8.7 | 812 | 1.40 | 5.7 |
| Example 20-4 | 50 | 10.0 | 5.4 | 370 | 0.25 | 2.7 |
| Example 20-5 | 20 | 3.0 | 13.3 | 473 | 0.34 | 2.9 |

EXAMPLE 21: Leak tests in oil-water mixture were developed to valid the potential of the invention as retinol protection and control release for cosmetic applications. The oil-water mixture was composed of 15.0 g of HPLC $H_2O$ and 25.0 g of capric caprylic oil. Leak test was developed as follow: 250 mg of material (containing retinol) was suspend in the oil-water mixture and stirred (180 rpm). The mixture was protected from light during the procedure. After some define amount of time, the stirring was stopped. Then, 5.0 g of caprylic capric oil was placed in a 25 mL volumetric flask and HPLC THF was used to complete the flask. The resulting mixture was analysed by HPLC to quantify the retinol concentration and to deduct the leaked quantify of retinol from the material.

Figure 16:
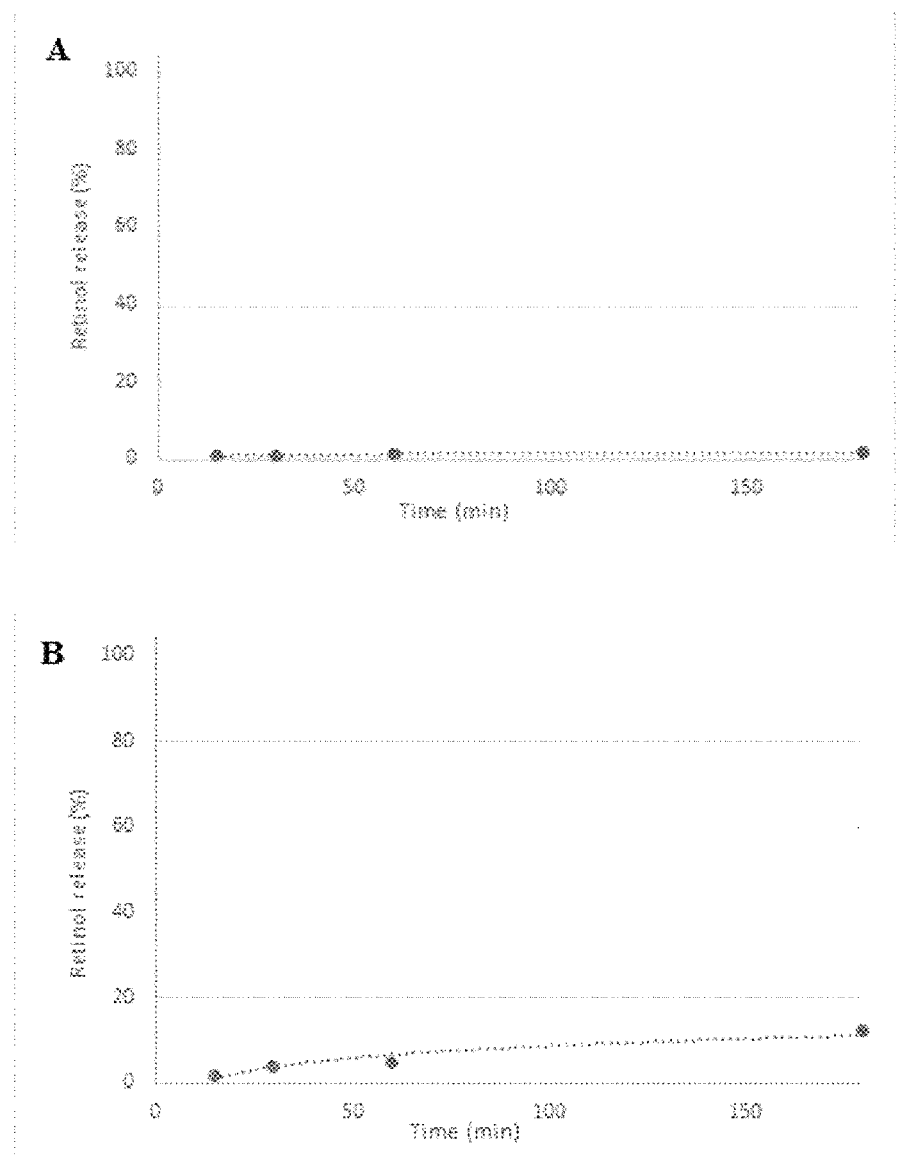
FIG. 16. A) Leak tests of core-shell sub-micron/microcapsules in microcapsules from Example 21-1; B) Leak tests of core-shell sub-micron/microcapsules in microcapsules from Example 21-2.

EXAMPLE 21-1: Leak test was done with core-shell sub-micron/microcapsules. Material from Example 1-2. Data are summarised in the FIG. 16(A).

EXAMPLE 21-2: Leak test was done with core-shell sub-micron/microcapsules. Material from Example 15-1. Data are summarised in the FIG. 16(B).

EXAMPLE 21. Conclusion: The leak tests show the potential of the invention for the use of retinol in cosmetic cream. The quantity of all-trans-retinol leaded in the oil-water mixture was very small.

EXAMPLE 22: Examples of the all-trans-retinol release performances achieved with the developed porous sub-micron/microspheres.

Release tests were performed to proof the ability of the developed sub-micron/microspheres to ensure the release of all-trans-retinol for cosmetic applications. The retinol release efficiency was performed in simulated sebum media composed of 33% squalene and 77% oleic acid. This media was used to mimic in vivo environment (i.e. skin environment). For this, 300 mg of sub-micron/microspheres were soaked in simulated sebum media at room temperature. At time points, 0.5 g release medium (i.e. simulated sebum) was removed and replaced with fresh medium (0.5 mL). The percentage of retinol released was evaluated by HPLC as described in this patent.

Figure 17:
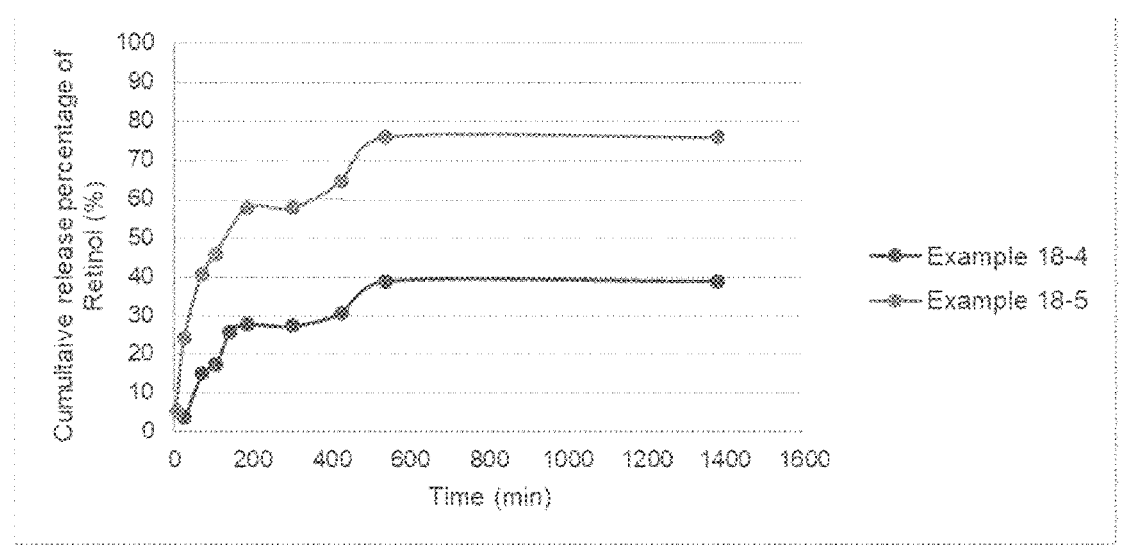
FIG. 17. All-trans-retinol release profiles from the developed sub-micron/microspheres in simulated sebum media (33% squalene+77% oleic acid).

As shown in FIG. 17, the obtained release kinetics demonstrate the promising potential of our technology and the developed sub-micron/microspheres for cosmetic uses. Indeed, a progressive all-trans-retinol release was observed for 9 hours and reaches a maximum cumulative release of about 75% for product obtained in Example 18-5 (hydrophobic sub-micron/microspheres) and 38% for product obtained in Example 18-(hydrophilic sub-micron/microspheres). Thus, the all-trans-retinol release can be controlled by adjusting the polarity (i.e. hydrophobicity/hydrophilicity) of the porous sub-micron/microspheres. Interactions between the payloads/actives and the surface have a major impact on the kinetics release. External surface of the spheres can play the role of a diffusion barrier which significantly affects the active release rate. The barrier can be the consequence of a repulsive interaction from the external layer (in our case hydrophilic/hydrophobic repulsion).

Figure 18:
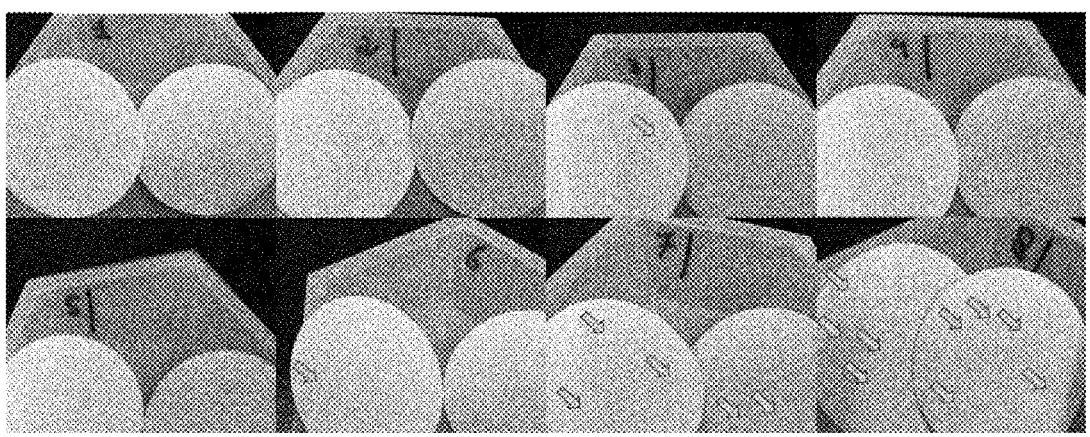
FIG. 18. Oil release from 75 mg of microcapsules from Example 1-2 for different mechanical pressures during 3 min. Tests 1 to 8, respectively 0, 3.3, 5.5, 7.8, 11.1, 38.6, 87.4, 308.4 g·cm$^{-2}$.

EXAMPLE 23: As shown in FIG. 18, the oil releases tests from non-porous microcapsules were also carry out using 75 mg of material from Example 1-2 and different weights were applied on it. The materials were placed between two pieces of filter paper and a cylindrical support was used as weight dispenser. The surface of the cylindrical support who applies the weight was 4.9 cm2. The weight was let in static place for 3 min. Until a 38.6 g·cm$^{-2}$ pressure was applied, the filter paper remained dry. After a pressure of 87.4 g·cm$^{-2}$ or more was applied, the filter paper was covered with yellow sticky oily material.

Sample Characterization

EXAMPLE 24: $^{29}$Si solid NMR. Solid state NMR spectra are recorded on a Bruker Avance spectrometer (Milton, ON) at a Silicon frequency of 79.5 MHz. Samples are spun at 8 kHz at magic angle at room temperature in a 4 mm ZrO rotor. A Hahn echo sequence synchronized with the spinning speed is used while applying a TPPM15 composite pulse decoupling during acquisition. 2400 acquisitions are recorded with a recycling delay of 30 seconds. The results are shown in Table 16.

$^{29}$Si solid NMR spectra allow to identify the number of bonds Si—O—X (X=C, Si, OH) which surround silicon atoms in the organosiloxane materials. The characteristic peaks of the TEOS, observed from about −90 ppm to about −110 ppm, were assigned to the structural units: Si(OSi)$_2$(OH)$_2$ (Q$_2$), Si(OSi)$_3$(OH) (Q$_3$), and Si(OSi)$_4$ (Q$_4$). In the first case silicon atom forms two bridging bonds, in the second case-tree bridging bonds, and in third-case-four bridges ones. The characteristic peaks of the organic modifiers, observed from about −40 ppm to about −70 ppm, were assigned to the structural units: RSiOSi(OH)$_2$ (T$_1$), RSi(OSi)$_2$(OH) (T$_2$), and RSi(OSi)$_3$ (T$_3$). In the first case silicon atom forms one bridging bonds, in the second case-two bridging bonds, and in third-case-tree bridges ones.

TABLE 16

$^{29}$Si solide NMR spectra.

| Examples | T$_n$ (ppm) | | | | Q$_n$ (ppm) | | | |
|---|---|---|---|---|---|---|---|---|
| | T$_1$ | T$_2$ | T$_3$ | T$_3$/T$_2$ | Q$_2$ | Q$_3$ | Q$_4$ | Q$_4$/Q$_3$; Q$_4$/Q$_2$ |
| Literature[1,2] | −46 | −56 | −66 | | −90 | −102 | −110 | |
| Example 1-2 | — | −54 | −63 | 1.3 | −91 | 100 | 109 | 1.0; 4.6 |
| Example 1-4 | — | −58 | −63 | 1.4 | −92 | 101 | 111 | 1.1; 4.8 |
| Example 6-2 | — | −59 | −65 | 1.33 | −91 | 101 | 111 | 1.0; 5.7 |
| Example 10-4 | — | −59 | −65 | 1.3 | −92 | 101 | 111 | 1.3; 8.3 |
| Example 17-4 | — | −59 | −65 | 3.2 | −92 | 101 | 110 | 1.4; 8.8 |

[1] Q. Cai, Z.-S. Luo, W.-Q. Pang, Y.-W. Fan, X.-H. Chan, and F. Z. Cui, *Chemistry of Materials*, 2001, 13, p. 258-263.
[2] Z. Olejniczak, M. Łęczka, K. Cholewa-Kowalska, K. Wojtach, M. Rokita, and W. Mozgawa, *Journal of Molecular Structure*, 2005, 744-747, 465-471.

Figure 19:
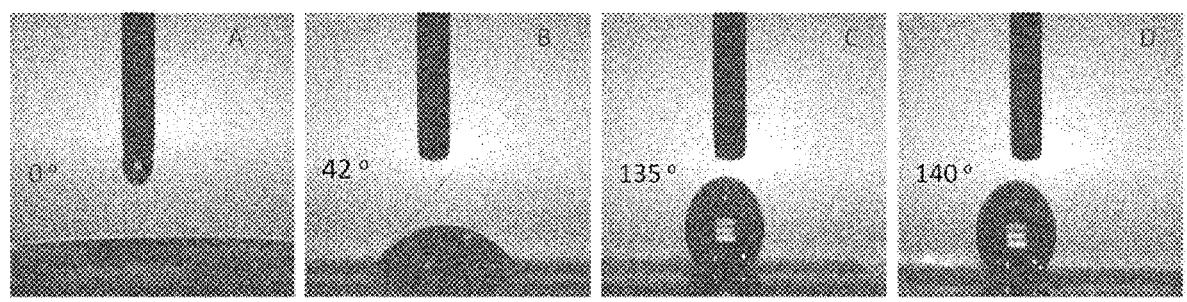
FIG. 19. Contact angle pictures. A) Example 20-1, B) Example 18-4, C) Example 18-5, and D) Example 14-1.
Figure 20:
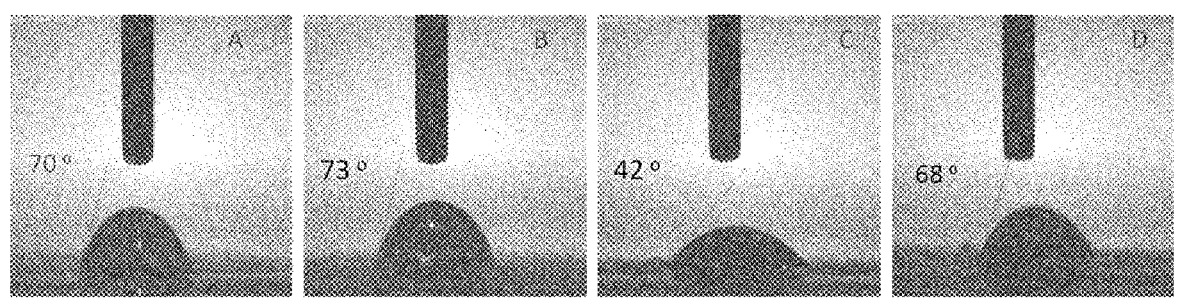
FIG. 20. Contact angle pictures. A) Example 1-2, B) Example 6-2, C) Example 18-4, and D) Example 19-4.

EXAMPLE 25: Physicochemical analysis of the external surface of the spheroidal particles:

EXAMPLE 25-1: Contact angle. A few milligrams of spheroidal microspheres are deposited on one side of a Micro-Tec D12 double sided non-conductive adhesive, which is fixed on to a Microscope glass slide. The sample layer is smoothed as much as possible. The contact angle is then characterized with VCA 2500 XE system. The results are shown in FIG. 19 and FIG. 20.

EXAMPLE 25-2: XPS analysis. XPS analysis shown the presence of 3 elements: Si, C and O. This confirms the presence of the functional groups of the silica precursors on the outer surface, in maximum depth of 5 nm, of the spheroidal particles. The obtained data (Table 17) revealed that spheroidal particles with hydrophobic external surface, having a high contact angle >100°, are characterized by higher carbon-to-silicon ratio (C/Si≥1.00; Example 14-1 and Example 18-5), compared to carbon-to-silicon ratio of spheroidal particles with hydrophilic external surface (C/Si<1.00; Example 1-2, Example 6-2 and Example 18-4). In addition, the higher the content of carbon in the silica precursors is, the higher the carbon-to-silicon ratio (C/Si) is (e.g. Example 1-2 (10% C1-TES) vs Example 6-2 (20% C2-DES)). Furthermore, XPS data revealed that the composition and the nature of the payload are critical parameters to control the self-organisation/orientation of the functional groups of the silica precursors, tailoring thus the polarity of the obtained spheroidal particles. Indeed, for example for particles obtained with 10% C1-TES-2.5% C18-87.5% TEOS (Example 18-4 and Example 18-5), the carbon-to-silicon ratio in Example 18-5 (C/Si=1.40) is significantly higher to that in Example 18-4 (C/Si=0.77). This suggests that the alkyl chains are more oriented/localized in the external surface for Example 18-5 but are more oriented/localized in the inner surface for Example 18-4. This is in good agreement with the water-dispersibility behavior of particles and the results obtained by contact angle, confirming that in the case of Example 18-5, the obtained spheroidal particles have a hydrophobic external surface; but in the case of Example 18-4, the obtained spheroidal particles have a hydrophilic external surface.

TABLE 17

XPS analysis

| Example | % C | % Si | % O | C/Si |
|---|---|---|---|---|
| Example 1-2 | 10 | 27.6 | 62.4 | 0.36 |
| Example 6-2 | 19.4 | 22.5 | 58.1 | 0.86 |
| Example 14-1 | 31.7 | 24.9 | 43.4 | 1.27 |
| Example 18-4 | 17.1 | 22.3 | 60.6 | 0.77 |
| Example 18-5 | 29.9 | 21.3 | 48.8 | 1.40 |

EXAMPLE 26: Particles size distribution. To measure the particle size distribution, silica microparticles (about 50 mg) are dispersed in methanol or in water (about 5 mL) in ultrasonic bath for 5 minutes to obtain a well dispersed solution, which is then added into the sonicated bath of Malvern Mastersizer 2000 (Hydro 2000S, Model AWA2001) till the obstruction of the signal is about 5 to 8%. The obtained data (Table 18) revealed that spheroidal particles with hydrophobic external surface, having a high contact angle >100° and characterized by a high carbon-to-silicon ratio (C/Si≥1.00; are not water dispersibles (Example 14-1 and Example 18-5).

TABLE 18

Particle size distribution (Malvern Mastersizer analysis)

| | MeOH | | Water | |
|---|---|---|---|---|
| Examples | D50 | D90/D10 | D50 | D90/D10 |
| Example 1-2 | 10 | 9.5 | 5.0 | 12.0 |
| Example 6-2 | 14 | 2.9 | 3.0 | 10.0 |
| Example 14-1 | 7 | 2.6 | No dispersibility | |
| Example 18-4 | 4 | 2.8 | 10.5 | 6.5 |
| Example 18-5 | 7 | 6.0 | No dispersibility | |
| Example 19-4 | 21 | 25.0 | 6.8 | 2.0 |
| Example 20-1 | 11 | 3.7 | 11.7 | 3.1 |

EXAMPLE 27: Specific surface area (BET) and porosity. The surface area and porosity of the silica microspheres were characterized with Micrometrics TriStar™ 3000 V4.01 and Micrometrics TriStar™ 3020 V3.02 at 77 K. The collected data were analyzed using the standard Brunauer-Emmett-Teller (BET) to get the surface area. The pore size data were obtained from the maxima of the pore size distribution curve calculated by Barrett-Joyner-Halenda (BJH) method using the desorption branch of the isotherm.

The non-porous particles were characterized with Autosorb Quantachrome® ASiQwin™ Instruments iQ2 v3.01 at 77 K. The collected data were analyzed using the multi-point Micropore BET iQ2 (Brunauer-Emmett-Teller) to get the surface area. The pore size was obtained from the maxima of the pore size distribution curve calculated by non local density functional theory (NLDFT). NLDFT method using the desorption branch of the isotherm. The pore volume data were obtained from NLDFT method cumulative pore volumes.

EXAMPLE 28-1 All-trans-retinol quantification in spheroidal microparticles. Silica particles containing all-trans-retinol (about 250 mg) obtained as described in the general procedure were suspended in 20 mL of a solution composed of tetrahydrofuran with 1000 ppm of isoeugenol. The mixture was ground using T-25 Ultra-Turrax at 10000 RPM for 20 minutes. The mixture was protected from light during the procedure. The resulting mixture was filtered through a 0.22 μm filter before HPLC analysis.

Retinol quantification is determined in this solution, using HPLC technique (Agilent 1100 equipped with a quaternary solvent delivery system (G1311A), vacuum degasser unit (G1322A), UV photodiode array detector (G1314A), standard autosampler (G1313A) and thermostatic column compartment (G1316A)). The column used in HPLC is a Silia-Chrom DtC18 column of 4.6×150 mm i.d., 3 μm, 150 Å. The mobile phase MPA consisted of water and mobile phase MPB consisted of Acetonitrile both containing 0.1% Formic Acid. Starting gradient condition: 40% MPA and 60% MPB linear gradient to 100% MPB on 5 minutes then hold at 100% MPB for 7 minutes. Flow rate was set to 1 ml/min, column temperature 35° C. and the detector at 325 and 300 nm. Retinol retention time=8.81 min. Isoeugenol (used as standard) retention time=3.87 min. Pure retinol from Sigma Aldrich was purchased for calibration curves.

EXAMPLE 28-2: Actives quantification in spheroidal microparticles others than retinol. Silica particles containing actives (about 250 mg) obtained as described in the general procedure were suspended in 20 mL of a solution composed of ethanol with 1000 ppm of isoeugenol. The mixture is ground using T-25 Ultra-Turrax at 10000 RPM for 20 minutes. The mixture was protected from light during the procedure. The resulting mixture was filtered through a 0.22 μm filter before GC-FID analysis.

The GC-FID analyses were performed using a Clarus 400 GC-FID System equipped with Rtx®-5 30 m capillary column (comprised of CrossBond 5% dimethylpolysiloxane, 0.53 mm inner diameter and 1.0 μm film thickness). The analyses were carried out in split mode, using hydrogen as carrier gas (pressure 10 psi). The injection temperature was 280° C. and the FID detector was set at 280° C. The column was maintained at an initial temperature of 50° C. for 2 min, then ramped to 200° C. at 25° C./min heating rate, and maintained to 200° C. for 4 min. The identification of the compounds was based on comparison of their retention times with those of authentic samples.

EXAMPLE 29: Scanning Electron Microscopy (SEM): SEM images of the spheroidal microparticles are recorded with FEI Quanta-3D-FEG at 3.0 kV without coating or with JEOL 840-A at 15 kV with gold coating.

EXAMPLE 30: Water Quantification in Silica Particles (Karl Fisher): The water percentage is estimated by using titrator Compact V20s from Mettler Toledo.

The invention claimed is:
1. A process of preparation of spheroidal organosiloxane particle consisting of:
  1) separately hydrolyzing two or more mono(silane) compounds in a hydrolytic media to provide two or more pre-hydrolyzed silica precursors and combining all the pre-hydrolyzed silica precursors into one container, wherein the mono(silane) compound contains one silicon atom of formula $R_{4-x}Si(L)_x$ or a dipodal silane compound containing two silicon atoms of formula $(L)_3Si—R'—Si(L)_3$, wherein:

R is an organic residue selected from alkyl, alkenyl, alkynyl, alicyclic, aryl, and alkyl-aryl groups, wherein each of said residues is optionally and independently substituted by one or more halogen atoms, glycidyloxy-, —OH, —SH, polyethylene glycol (PEG), —N(R$_a$)$_2$, —N$^+$(R$_a$)$_3$;

L is a halogen or an acetoxide —O—C(O)R$_a$, or alkoxide —OR$_a$ group;

R' is an organic residue linking the two silane units of a dipodal silane compound, wherein said organic residue is selected from alkyl, alkenyl, alkynyl, alicyclic, aryl, and alkyl-aryl groups, wherein each of said residues is optionally and independently substituted by a halogen atom, —OH, —SH, —N(R$_a$)$_2$, —N+(R$_a$)$_3$;

R$_a$ is hydrogen, alkyl, alkenyl, alkynyl, alicyclic, aryl or alkyl-aryl; and x is an integer of 1 to 4;

2) pre-condensing said one or more pre-hydrolyzed silica precursors of step 1) by removing a portion of or all volatile solvents from the hydrolytic media to provide a pre-condensed silica precursor mixture;

3) adding a liposoluble payload to the mixture of step 2) to provide a dispersed phase;

4) emulsifying, in absence of a surfactant, the dispersed phase of the step 3) in an aqueous continuous phase to provide an oil-in-water emulsion; and 5) adding a condensation catalyst to the emulsion of step 4) to obtain said spheroidal organosiloxane particle.

2. The process of claim 1, wherein said liposoluble payload is a cosmetic, cosmeceutical, dermatological, pharmaceutical, perfume, or flavoring ingredient.

3. The process of claim 1, wherein said liposoluble payload is a mixture of a cosmetic, cosmeceutical, pharmaceutical, dermatological, perfume, or flavoring ingredient together with a triglyceride.

4. The process of claim 1, wherein said liposoluble payload is a mixture of all-trans-retinol, a triglyceride and a non-toxic antioxidant.

5. The process of claim 1, wherein said liposoluble payload is a mixture of all-trans-retinol and one or more unsaponifiable saturated compounds comprising alkanes, iso-alkanes, or cycloalkanes.

6. The process of claim 1, wherein said liposoluble payload is a cannabinoid, a mixture of cannabinoids or extract of Cannabaceae biomass.

7. The process of claim 6, wherein said liposoluble payload cannabinoid comprises at least one of tetrahydrocannabinol, cannabidiol, cannabigerol, iso-tetrahydrocannabinol, and cannabinol.

8. The process of claim 1, wherein said liposoluble payload of said step 3) is added in a solid form.

9. The process of claim 1, wherein said liposoluble payload of said step 3) is added in a liquid form.

10. A spheroidal organosiloxane particle obtained by the process of claim 1 consisting of an organosiloxane network, wherein said particle is uncalcined, amorphous, surfactant-free, and is a sub-micron to micron size particle containing a liposoluble payload consisting of one or more actives, and either:

(i) wherein said spheroidal organosiloxane particle is a microcapsule of micron size having a core/shell structure;

wherein said spheroidal organosiloxane microcapsule is non-porous as assessed by pore volume, pore diameter, and specific surface area as measured by $N_2$ physisorption;

wherein said core of said spheroidal organosiloxane microcapsule comprises one or more sub-micron to micron size internal spheroidal sub-micron/microcapsules, wherein said internal spheroidal sub-micron/microcapsules have a size smaller than said spheroidal particle; and wherein at least one of said spheroidal microcapsule and internal spheroidal sub-micron/microcapsules comprise the liposoluble payload; or (ii) wherein said spheroidal organosiloxane particle is a microcapsule of micron size having a core/shell structure;

wherein said spheroidal organosiloxane microcapsule is porous as assessed by pore volume, pore diameter, and specific surface area as measured by $N_2$ physisorption;

wherein said core of said spheroidal organosiloxane microcapsule comprises one or more sub-micron to micron size internal spheroidal sub-micron/microcapsules, wherein said internal spheroidal sub-micron/microcapsules have a size smaller than said spheroidal particle; and wherein at least one of said spheroidal microcapsule and internal spheroidal sub-micron/microcapsules comprise the liposoluble payload.

11. The spheroidal organosiloxane particle of claim 10, wherein said one or more actives comprise all-trans-retinol, cannabinoid or a mixture thereof in a triglyceride and a non-toxic antioxidant.

* * * * *